(12) United States Patent
Dondero et al.

(10) Patent No.: US 8,703,929 B2
(45) Date of Patent: Apr. 22, 2014

(54) COMPOSITIONS COMPRISING SIRNA AND PLASMIDS

(75) Inventors: Richard S. Dondero, Riverdale, NJ (US); John E. Thompson, Waterloo (CA); Catherine A. Taylor, Waterloo (CA)

(73) Assignee: Senesco Technologies, Inc., New Brunswick, NJ (US)

( * ) Notice: Subject to any disclaimer, the term of this patent is extended or adjusted under 35 U.S.C. 154(b) by 0 days.

(21) Appl. No.: 12/400,742

(22) Filed: Mar. 9, 2009

(65) Prior Publication Data

US 2010/0004314 A1 Jan. 7, 2010

Related U.S. Application Data

(60) Provisional application No. 61/034,830, filed on Mar. 7, 2008.

(51) Int. Cl.
*C07H 21/00* (2006.01)
*C07H 21/02* (2006.01)

(52) U.S. Cl.
USPC ........................................ 536/24.5; 536/23.1

(58) Field of Classification Search
None
See application file for complete search history.

(56) References Cited

U.S. PATENT DOCUMENTS

| | | | |
|---|---|---|---|
| 5,849,587 | A | 12/1998 | Hanauske-Abel et al. |
| 6,033,910 | A | 3/2000 | Monia et al. |
| 6,448,040 | B1 | 9/2002 | Young et al. |
| 6,468,983 | B2 | 10/2002 | Silverman et al. |
| 7,381,708 | B2 | 6/2008 | Taylor et al. |
| 2003/0077262 | A1 | 4/2003 | Franzoso et al. |
| 2003/0225022 | A1 | 12/2003 | Taylor et al. |
| 2004/0023850 | A1* | 2/2004 | Wolff et al. ........................ 514/2 |
| 2006/0287265 | A1* | 12/2006 | Thompson et al. ............. 514/44 |
| 2007/0154457 | A1* | 7/2007 | Thompson et al. ........... 424/93.2 |

FOREIGN PATENT DOCUMENTS

| | | |
|---|---|---|
| WO | 94/15596 | 7/1994 |
| WO | 96/25492 | 8/1996 |
| WO | 96/41639 | 12/1996 |
| WO | 99/01551 | 1/1999 |
| WO | 01/02592 | 1/2001 |
| WO | 01/10906 | 2/2001 |
| WO | 03/010286 | 2/2003 |
| WO | 2004/078940 | 9/2004 |
| WO | 2004/113528 | 12/2004 |
| WO | 2005/007853 | 1/2005 |

OTHER PUBLICATIONS

Gordon, et al. (2003) Somatic Hypermutation of the B Cell Receptor Genes B29 (IGB, CD79B) and MB1 (AGG, CD79A). PNAS, v.100(7):4126-31.*

Shim, et al. (2009) Acid-Responsive Linear Po9lethylenimine for Efficient, Specific, and Biocompatible siRNA Delivery. Bioconjugate Chemistry, v.20:488-99.*
Cano, et al. (2008) Mutational Analyses of Human EIF5A-1: Identifcation of Amino Acid Residues Critical for Hypusine Modification and EIF5A Activity. FEBS Journal, v.275(1):44-58.*
Park, et al. (1993) Is Hypusine Essential for Eukaryotic Cell Proliferation? TIBS, v.18(12):475-9.*
Gordon et al. "Eukaryotic Initiation Factor 4D, the Hypusine-containing Protein, Is Conserved among Eukaryotes". (1987a) J. Biol. Chem., 262, 16585-16589.
Park et al. "Hypusine: its post-translational formation in eukaryotic initiation factor 5A and its potential role in cellular regulation". (1993) Biofactors, 4, 95-104.
Schnier et al. "Translation Initiation Factor 5A and Its Hypusine Modification Are Essential for Cell Viability in the Yeast *Saccharomyces cerevisiae*". (1991) Mol. Cell. Biol., 11, 3105-3114.
Sasaki et al. "Deoxyhupusine synthase gene is essential for cell viability in the yeast *Saccharomyces cerevisiae*". (1996) FEBS Lett., 384, 151-154.
Park et al. (1998) J. Biol. Chem., 273. 1677-1683.
Kang et al. (1993), "Effect of initiation factor eIF-5A depletion on cell proliferation and protein synthesis," in Tuite, M. (ed.), Protein Synthesis and Targeting in Yeast, NATO Series H.
Xu & Chen (2001) "Hypusine Is Required for a Sequence-specific Interaction of Eukaryotic Initiation Factor 5A with Postsystematic Evolution of Ligands by Exponential Enrichment RNA". J. Biol. Chem., 276, 2555-2561.
Chauhan et al. "Multiple Myeloma Cell Adhesion-Induced Interleukin-6 Expression in Bone Marrow Stromal Cells Involves Activation of NF-kB" (1996) Blood 87, 1104.
Hideshima et al. "The role of tumor necrosis factor alpha in the pathophysiology of human multiple myeloma: therapeutic applications". (2001) Oncogene 20,4519.
Hideshima et al. "NF-kB as a Therapeutic Target in Multiple Myeloma". (2002) JBC 277, 16639.
Malone et al. 2006. B29 gene silencing in pituitary cells is regulated by its 3' enhancer. J. Mol. Biol. 362: 173-183.
Komatsu et al. 2002. Novel regulatory regions found downstream of the rat B29/lg-b gene. Eur. J. Biochem. 269 : 1227-1236.
Chay KO, Park SS, Mushinski JF (2002). Linkage of caspase-mediated degradation of paxillin to apoptosis in Ba/F3 murine pro-B lymphocytes. J Biol Chem. 277, 14521-14529.
Fischer U, Janicke RU, Schulze-Osthoff K (2003). Many cuts to ruin: a comprehensive update of caspase substrates. Cell Death and Differentiation 10, 76-100.

(Continued)

*Primary Examiner* — Jennifer McDonald
(74) *Attorney, Agent, or Firm* — Morgan Lewis & Bockius LLP

(57) ABSTRACT

The present invention relates to the combinatorial use of an siRNA targeted against an endogenous gene to knock out or knock down expression of the endogenous gene in a host and a delivery of a polynucleotide encoding the gene in a delivery vehicle/expression vector to the host to provide expression in the host of the protein encoded by the polynucleotide.

7 Claims, 42 Drawing Sheets

(56) References Cited

OTHER PUBLICATIONS

Kim, S. C., Sprung, R., Chen, Y., Xu, Y., Ball, H., Pei, J., Cheng, T., Kho, Y., Xiao, H., Xiao, L., Grishin, N. V., White, M., Yang, X. J., and Zhao, Y. (2006) Substrate and Functional Diversity of Lysine Acetylation Revealed by a Proteomics Survey, Mol Cell 23, 607-618.
Shirai et al. (2008). Global analysis of gel mobility of proteins and its use in target identification J. Biol. Chem. 283, 10745-10752.
Bevec Dorian et al: "Molecular Characterization of a cDNA encoding functional human deoxyhypusine synthase and chromosomal mapping of the corresponding gene locus", FEBS Letters, vol. 378, No. 2, 1996, pp. 195-198, XP002400480, ISSN: 0014-5793.
Chen, K.Y. et al, "RNA Interference Analysis of the Function of Hypusine-Containing Eukaryotic Initiation Factor 5A in C. elegans," FASEB Journal (Federation of American Societies for Experimental Biology), Mar. 20, 2002, p. A162, vol. 16, No. 4, XP008033807, ISSN: 0892-6638, Bethesda, US.
Crooke, S. (2004) Progress in Antisense Technology. Annu. Rev. Med. v 44: 61-95.
Database EMBL (online) Jul. 7, 2000 "hv36b09.x1 NCI_CGAP_Lu24 *Homo sapiens* cDNA clone Image: 3175481 3 prime similar to SW: DHYS_Human P49366 Deoxyhypusine Synthase:, mRNA sequence." retrieved from EBI accession No. EM_EST:BE218247.
Database EMBL: (online) Dec. 14, 1999, uo59b11.y1 NCI_CGAP_Mam1 *Mus Musculus* cDNA clone, Inage: 2646813 5 prime similar to gb: M23419 Initiation factor 5A (Human); mRNA sequence, retrieved from EBI accession No. EM_PRO: AW229460.
Hazeki, et al. (2009) Role of Phosphoinositide 3-Kinase in Innate Immunity. Biol. Pham. Bull., v. 30(9): 1617-1623.
Jen et al. "Supression of Gene Expression by Targeted Disruption of Messenger RNA: Available Options and Current Strategies" (Stem Cells 2000, vol. 18, p. 307-319).
Kalota, et al: Progress in the Development of nucleic Acid Therapeutics. Handbook of Experimental Pharmacology, V. 176, pp. 173-196 (2006).
Opalinska et al. "Nucleic-Acid Therapeutics: Basic Principles and Recent Applications" (Nature Reviews Drug Discovery, 2002, vol. 1, p. 503-514.
Smit-McBride, et al. Sequence Determination and cDNA Cloning of Eukaryotic Initiation Factor 4D, the Hypusine-containing Protein, J. Biol. Chem. v 264(3): 1578-1583. (1989).
Taylor, et al., Antisense Oligonucleotides: a Systematic high-Throughput Approach to Target Validation and Gene Functions Determination, Drug Discovery Today, v. 4: 562-567 (1999).
Vickers, et al. (2003) Efficient Reduction of Target RNAs by Small Interfering RNA and RNASE H-Dependent Antisense Agents. J. Biol. Chem., v. 278(9): 7108-18.
Eck et al, Goodman & Giiman's the Pharmacolotgical basis of Therapeutics, McGraw-Hill, New York, NY. pp. 77-101, 1995.
Hunt et al, "Hurdles and Hopes for Cancer Treatment". (Science, 297: 415-416, 2002).
Thomas et al, "Progress and Problems with the Use of Viral Vectors for Gene Therapy". (Nature, 4; 346-358, 2003).
Rubanyi et al. "The future of human gene therapy". (Molecular Aspects of Medine, 2001, 22, 113-142).
Vieyra et al, "Proapoptotic role of novel gene-expression factors" (Clin Transl Oncol, 9: 355-363, 2007).
Li et al, "A Novel eIF5A Complex Functions As a Regulator of p53 and p53-dependent Apoptosis". (JBC, 279: 49251-48258, 2004).
Taylor et al, p. 446; "Eukaryotic translation initiation factor 5A induces apoptosis in colon cancer cells and associates with the nucleus in response to tumour necrosis factor alpha signalling". Experimental Cell research 313: 437-449, (2007).
Voskoglou-Nomikos et al "Cinical Predictive Value of the in Vitro Cell Line, Human Xenograft, and Mouse Allograft Preclinical Cancer Models". (Clinical Cancer Research, 2003, 9, 4227-4239).
Kelland et al. ""Of mice and Men": values and liabilities of the athymic nude mouse model in anticancer drug development". (European Journal of Cancer, 2004, 40, 827-836).
Kerbel et al. Models of Anti-Cancer Therapy: Human Tumor Xenografts as Predictive Preclinical Models for Anticancer Drug Activity in Humans; Better Than Commonly Perceived—But They Can Be Improved (Cancer Biology & therapy 2:4 Suppl. 1, S134-139), 2003.
Soh et al. "Thyroid-stimulating hormone promotes the secretion of vascular endothelial growth factor in thyroid cancer cell lines". (Surgery, 129(6): 944-7, 1996).
Terman et al. "VEGF and Tumor Angiogenesis". Einstein Quart. J. Biol. and Med, 2001, 18: 59-66.
Nigro et al. "Mutations in the p53 gene occur in diverse human tumour types". Nature, 342: 705-708 (1989).
Hayashizaki etal., "Analysis of the Mouse Transcriptome Based on Functional Annotation of 60,770 Full-Length cDNAs," Nature, United Kingdom, vol. 420, No. 6915, pp. 563-573, ISSN: 0028-0836, XP002965277, Dec. 5, 2002.
Jin. Bao-Feng et al., "Proteomic analysis of ubiquitin-proteasome effects: insight into the future of eukaryotic initiation factor 5A," Oncogene, Jul. 31, 2003, pp. 4819-4830, vol. 22, No. 31, Nature Publishing Group, XP-002388453, ISSN: 0950-9232.
Annexes to Form PCT/ISA/206, Invitation to Pay Additional Fees, Communication Relating to the Results of the Partial International Search, PC11US20051044266, Aug. 11, 2006, comprised of the Annex first, continuation and 4th of 5 extra sheets and the Patent Family Annex, European Patent Office, International Searching Authority, Rijswijk, NL.
Tome M E et al: "Excess putrescine accumulation inhibits the formation of modified eukaryotic initiation factor 5A (eIF-5A) and induces apoptosis", Biochemical Journal, Portland Press, London, GB, vol. 328, pp. 847-854, 1997, ISSN: 0264-6021.
Database EMBL (Online) Dec. 14, 1999, "uo59b11.y1 NCI_CGAP_Mam1 *Mus musculus* cDNA clone, Image: 26468135' similar to gb:M23419 Initiation Factor 5A (Human);, mRNA sequence", retrieved from EBI accession No. EM_PRO:AW229460.
Database EMBL (Online) Dec. 11, 1995 "Human deoxyhypusine synthase mRNA, complete cds." retrieved from EBI accession No. EM_HUM:U40579.
Wolff Edith C et al: "Deoxyhypusine synthase from rat testis: Purification and characterization", Journal of Biological Chemistry, vol. 270, No. 15, 1995, pp. 8660-8666, XP002978937, ISSN: 0021-9258.
Joe Young AE et al: "Cloning and expression of human deoxyhypusine synthase cDNA: Structure-function studies with recombinant enzyme and mutant proteins", Journal of Biological Chemistry, vol. 270, No. 38, 1995. pp. 22386-22392, XP002400481, ISSN: 0021-9258.
Database EMBL (Online) Jul. 7, 2000 "hv36b09.x1 NCI_CGAP_Lu24 *Homo sapiens* cDNA clone Image:3175481 3' similar to SW:DHYS_Human P49366 Deoxyhypusine Synthase ;, mRNA sequence." retrieved from EBI accession No. EM_EST:BE218247.
Bartig et al. "The Unique Posttranslational Modification Leading to Deoxyhupusine or Hypusine is a General Feature of teh Archaebacterial Kingdom". (1990) System. Appl. Microbial., 13, 112-116.
Zhang Xuchen et al.: "Small Interfering RNA Targeting Heme Oxygenase-1 Enhances Ischema-Reperfusion-Induced Lung Apoptosis" Journal of Biological Chemistry, American Society of Biochemical Biologists, Birmingham, US, vol. 279, No. 11, March 12, 2004, pp. 10677-10684, XP002343181 ISSN: 0021-9258; Whole Document.
Ruhl M et al: "Eukaryotic Initiation Factor 5A Is a Cellular Target of the Human Immunodeficiency Virus Type 1 Rev Trans-Activation" Journal of Cell Biology, Rockefeller Univeristy Press, New York, US, US, vol. 123, No. 6, Dec. 1, 1993, pp. 1309-1320, XP0005751505 ISSN 0021-9525; The Whole Document.
Caraglia M et al: "The Role of Eukaryotic Initiation Factor 5A in the Control of Cell Proliferation and Apoptosis" Amino Acids, Springer Verlag, AU, vol. 20, No. 2, 2001, pp. 91-104, XP002291822, ISSN: 0939-4451; The Whole Document.
Zhang Xuchen et al.: "Small Interfering RNA Targeting Heme Oxygenase-1 Enhances Ischema-Reperfusion-Induced Lung Apoptosis" Journal of Biological Chemistry, American Society of Biochemical Biologists, Birmingham, US, vol. 279, No. 11, Mar. 12, 2003, pp. 10677-10684, XP002343181 ISSN: 0021-9258; Whole Document CI.

(56) References Cited

OTHER PUBLICATIONS

International Search Report of PCT/US20051025766, Mar. 10, 2006.
Heijstek et al. "Mouse Models of Colorectal Cancer and Liver Metastases". (Digestive Surgery 22: 16-25, 2005).
Herweijer et al. "Progress and Prospects: naked DNA gene transfer and therapy". (Gene Therapy, 10: 453-458, 2003).
Siuciak et al. "Behavioral and neurochemical characterization of mice deficient in teh phosphodiesterase-4B (PDE4B) enzyme". (Psychopharmacology 197: 115-126, 2008).
Linder et al, "Genetic Variables that Influence Phenotype". (ILAR Journal, 47(2): 132-40, 2006).
Ma et al Inhibition of Metastasis of Intraocular Melanomas by Adenovirus-Mediated Gene Transfer of Plasminogen Activator inhibitor Type 1 (PAI-1) in an Athymic Mouse Model:. (Blood, 90(7): 2738-46, 1997).
Caraglia et al. "Modulation of molecular mechanisms involved in protein synthesis machinery as a new tool for the control of cell proliferation". (EurJ Biochem. 267: 3919-3936 (2000).
Provost et al. (2002) Ribonuclease Activity and RNA Binding of Recombinant Human Dicer, EMBO J. 21(21): 5864-5874.
Tabara et al. (2002) The dsRNA Binding Protein RDE-4 Interacts with RDE-1, DCR-1 and a DexH-box Helicase to Direct RNAi in *C. elegans*, Cell 109(7):861-71.
Ketting et al. (2002) Dicer Functions in RNA Interference and in Synthesis of Small RNA Involved in Developmental Timing in *C. elegans*.
Martinez et al., Single-Stranded Antisense siRNAs Guide Target RNA Cleavage in RNAi, Cell 110(5):563, pp. 563-574; Sep. 6, 2002.
Hutvagner & Zamore (2002) A microRNA in a multiple-turnover RNAi enzyme complex, Science 297:2056.
Sharp, RNA interference—2001, Genes Dev. 2001, 15:485.
Bernstein, Caudy, Hammond, & Hannon (2001) Role for a bidentate ribonuclease in the initiation step of RNA interference, Nature 409:363.
Nykanen, Haley, & Zamore (2001), ATP requirements and small interfering RNA structure in the RNA interference pathway, Cell 107:309.
Elbashir, Lendeckel, & Tuschl (2001) RNA interference is mediated by 21- and 22-nucleotide RNAs, Genes Dev. 15:188.
Kisielow, M. et al. (2002), Isoform-specific knockdown and expression of adaptor protein ShcA using small interfering RNA, J. Biochem. 363:1-5.
Fire, A. et al. "Potent and specific genetic interference by double-stranded RNA in *Caenorhabditis elegans*". (1998) Nature 391:806-811.
Shirai et al. "Global Analysis of Gel Mobility of Proteins and Its Use in Target Identification". Journal of Biological Chemistry; vol. 283. No. 16. pp. 10745-10752; Apr. 18, 2008.

Luo, Dan, et al., "Synthetic DNA delivery systems". Nature Biotechnology, vol. 18, Jan. 2000, pp. 33-37.
Hortobagyi, Gabriel N., et al. "Cationic Liposome-Mediated E1A Gene Transfer to Human Breast and Ovarian Cancer Cells and Its Biologic Effects: A Phase I Clinical Trail", J. Clinical Oncology, vol. 19, Issue 14 (Jul. 2001):3422-3433.
Yu, Wei, et al. "Enhanced transfection efficiency of a systemically delivered tumor-targeting immunolipoplex by inclusion of a pH-sensitive histidylated oligolysine peptide". Nucleic Acids Research. 2004, 32(5);e48.
Marjoros, Istvan, J., et al, "PAMAM Dendrimer-Based Multifunctional Conjugate for Cancer Therapy: Synthesis, Characterization, and Functionality," Biomacromolecules, vol. 7, No. 2, 2006; 572-579.
Majoros, Istvan J., et al. "Poly(amidoamine) Dendrimer-Based Multifunctional Engineered Nanodevice for Cancer Therapy". J. Med. Chem, 2005, 48, 5892-5899.
Ohana et al., "Regulatory sequences of the H-19 gene in DNA based therapy of bladder cancer". 2004. Gene Ther Mol Bio 8:181-192.
Vemejoul et al., "Antitumor Effect of in Vivo Somatostatin Receptor Subtype 2 Gene Transfer in Primary and Metastatic Pancreatic Cancer Models". 2002. Cancer Research 62:6124-31.
Urbain-Klein et al., "RNAi-mediated gene-targeting through systemic application of polyethylenimine (PEI)-complexed siRNA in vivo". 2004. Gene therapy 23:1-6.
Grezelinski et al. "RNA Interference-Mediated Gene Silencing of Pleiotrophin Through Polyethylenimine-Complexed Small Interfering RNAs in Vivo Exerts Antitumoral Effects in Glioblastoma Xenografts" 2006. Human Gene Therapy 17:751-66.
Garzon et al. "Induction of gp 120-specific protective immune responses by genetic vaccination with linear polyethylenimine-plasmid complex". 2005. Vaccine 23:1384-92.
Lemkine et al. "Preferential Transfection fo Adult Mouse Neural Stem Cells and Theuir Immediate Progeny in Vivo with Polyethylebnimine". 2002. Mol. Cell. Neurosci. 19:165-174.
Liu & Tartakoff (1997) Supplement to Molecular Biology of the Cell, 8, 426a. Abstract No. 2476, 37th American Society for Cell Biology Annual Meeting.
Rosorius et al. "Nuclear pore localization and nucleocytoplasmic trasport eIF-5A: evdence for direct interaction wth the export receptor CRM1". (1999) J. Cell Science, 112, 2369-2380.
Park "The identification of an Eukaryotic Initiation Factor 4D Precursor in Spermidine-depleted Chinese Hamster Ovary Cells". (1988) J. Biol. Chem., 263, 7447-7449.
Schumann & Klink: "Archaebacterial Protein Contains Hypusine, a Unique Amino Acid Characteristic for Eukaryotic Translation Initiation Factor 4D". (1989) System. Appl. Microbiol., 11, 103-107.

* cited by examiner

Amino Acid Sequence of Human eIF5A1

```
                                                        Hypusination site
                              acetylation site K47 K50
         1                                              ↓
pHM6 - eIF5A1 # 2  MADDLDFETG DAGASATFPM QCSALRKNGF VVLKGRPCKI VEMSTSKTGK
         genbank  MADDLDFETG DAGASATFPM QCSALRKNGF VVLKGRPCKI VEMSTSKTGK
       Consensus  MADDLDFETG DAGASATFPM QCSALRKNGF VVLKGRPCKI VEMSTSKTGK
                                    UQ
                                PKC K67
        51                                                        100
      #  HGHAKVHLVG IDIFTGKKYE DICPSTHNMD VPNIKRNDFQ LIGIQDGYLS
         genbank  HGHAKVHLVG IDIFTGKKYE DICPSTHNMD VPNIKRNDFQ LIGIQDGYLS
       Consensus  HGHAKVHLVG IDIFTGKKYE DICPSTHNMD VPNIKRNDFQ LIGIQDGYLS 101                                                       150
      #  LLQDSGEVRE DLRLPEGDLG KEIEQKYDCG EEILITVLSA MTEEAAVAIK
         genbank  LLQDSGEVRE DLRLPEGDLG KEIEQKYDCG EEILITVLSA MTEEAAVAIK
       Consensus  LLQDSGEVRE DLRLPEGDLG KEIEQKYDCG EEILITVLSA MTEEAAVAIK 151
      #  AMAK
         genbank  AMAK
       Consensus  AMAK
```

PKC = putative protein kinase C phosphorylation site
UQ = putative ubiquitination site (K67)
K47 = confirmed acetylation site
K50 = confirmed hypusination site
pHM6-eIF5A1 # 2 = predicted amino acid sequence of human eIF5A1 in pHM6 vector
Genbank = amino acid sequence of human eIF5A1 (ACCESSION # NP_001961)

FIG. 1

Mutation of eIF5A1 at K50 and K67 increases accumulation of transfected protein.

Mutation of eIF5A1 at K50 and K67 increases accumulation of transfected protein.

Mutation of eIF5A1 at K47, K50 and K67 increases accumulation of transfected protein.

Pre-treatment with eIF5A1 siRNA #1 reduces expression of endogenous eIF5A1 but allows accumulation of RNAi-resistant eIF5A1$^{k50A}$ expressed by adenovirus Pre-treatment with eIF5A1 siRNA #1 prior to Adenovirus infection reduces expression of phosphorylated NF-kB in human multiple myeloma cells Pre-treatment with eIF5A1 siRNA #1 prior to Adenovirus infection reduces expression of phosphorylated NF-kB and ICAM-1 in human multiple myeloma cells siRNA-mediated suppression of eIF5A in human multiple myeloma Cells inhibits LPS-mediated induction of NFkB DNA-Binding Activity

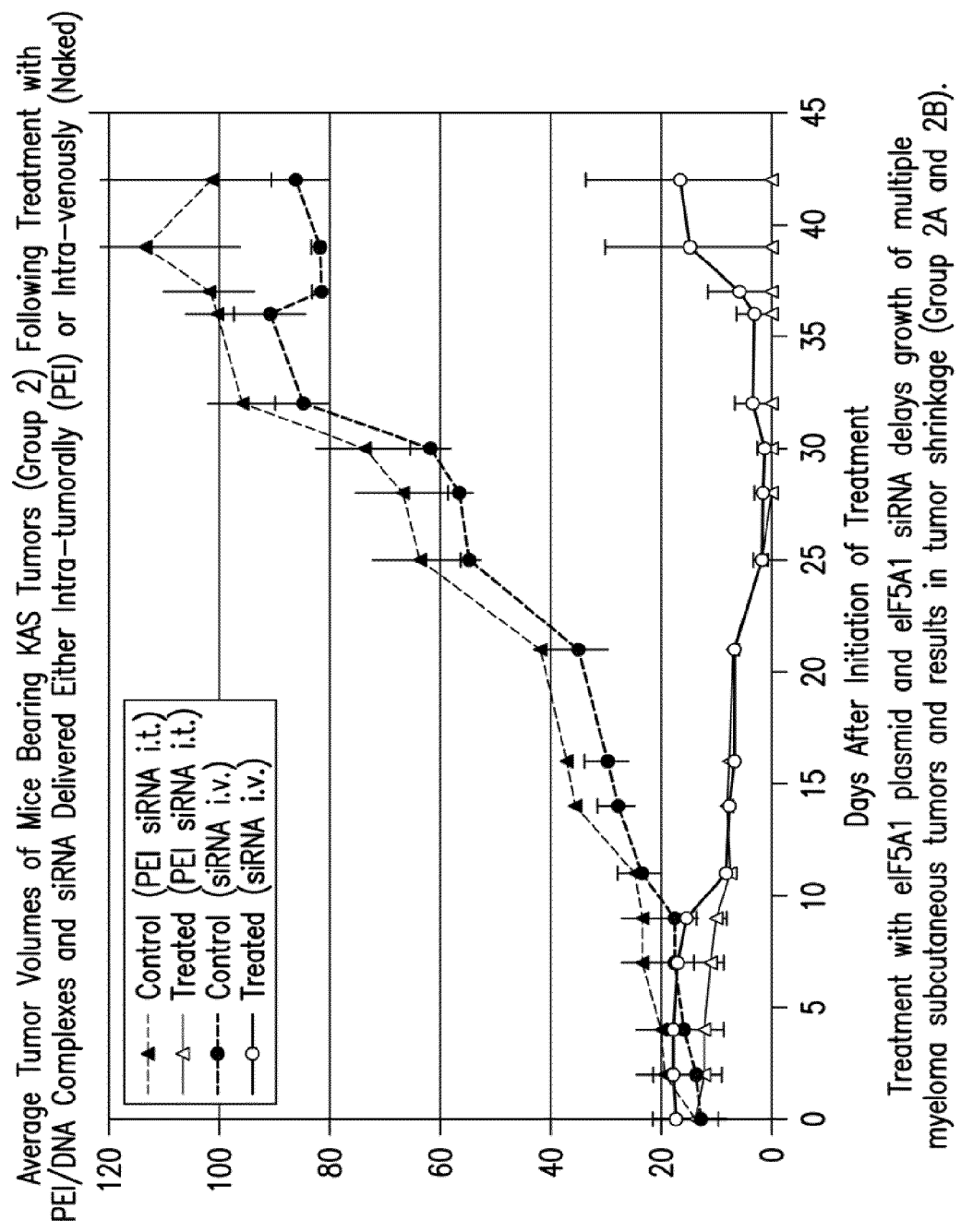

Group 2A - mouse G-6
Group 2A - mouse G-5
Group 2A - mouse G-4

Co-administration of eIF5A1 plasmid and eIF5A1 siRNA results in tumor shrinkage (Group 2A). No tumor growth was observed in any of the group 2A treated mice.

Administration of eIF5A1 siRNA intra-venously (i.v.) and PEI/eIF5A1$^{K50R}$ plasmid complexes intra-tumorally (i.t.) results in tumor shrinkage of multiple myeloma subcutaneous tumors (Group 2B). There was no evidence of tumor growth in one mouse of the treatment group (group 2B).

Co-administration of eIF5A1 plasmid and eIF5A1 siRNA delays growth of multiple myeloma subcutaneous tumors and results in tumor shrinkage (Group A).

Co-administration of eIF5A1 plasmid and eIF5A1 siRNA delays growth of multiple myeloma subcutaneous tumors and results in tumor shrinkage (Group A).

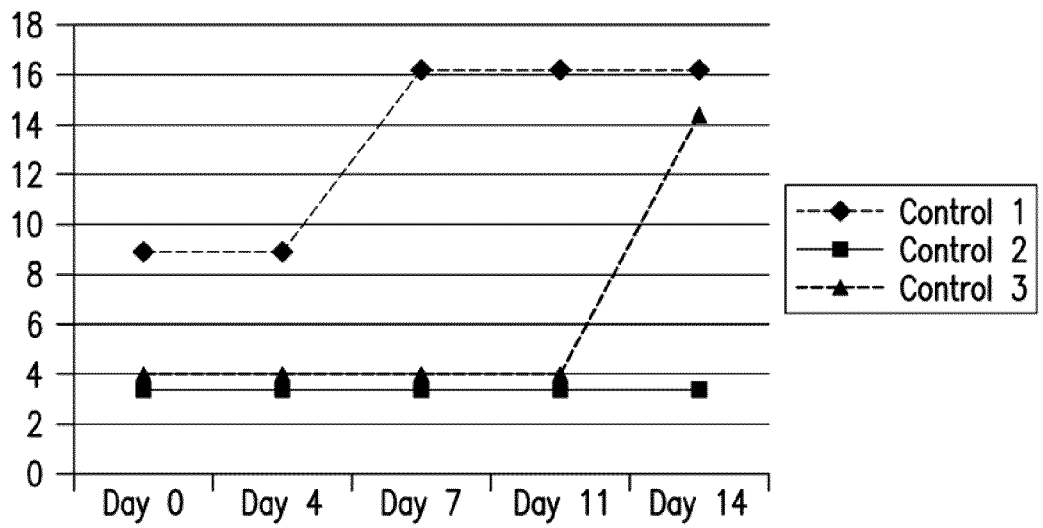

Administration of eIF5A1 siRNA intra-venously (i.v.) and PEI/eIF5A1$^{K50R}$ plasmid complexes intra-tumourally (i.t.) results in tumor shrinkage of multiple myeloma subcutaneous tumors (Group B).

FIG.18A

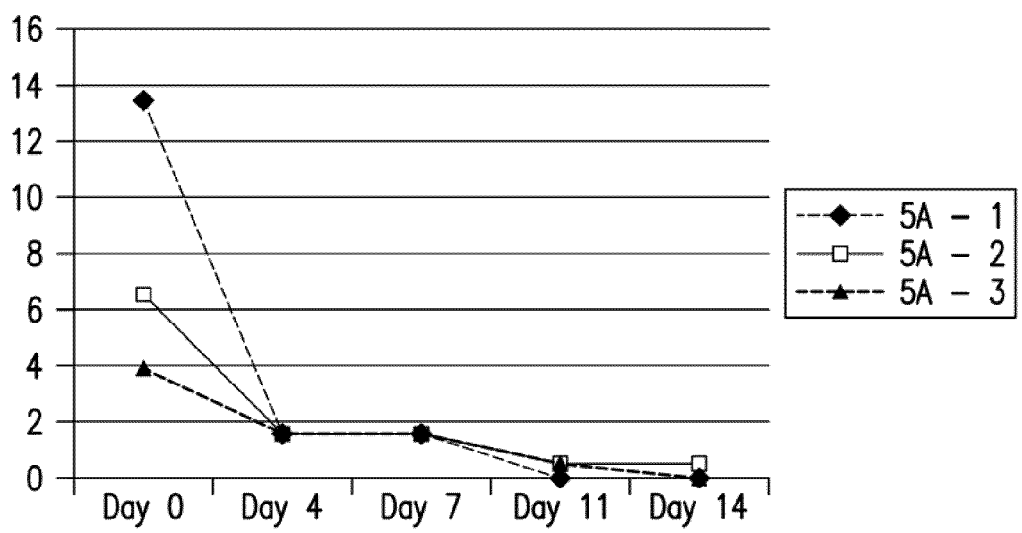

Administration of eIF5A1 siRNA intra-venously (i.v.) and PEI/eIF5A1$^{K50R}$ plasmid complexes intra-tumourally (i.t.) results in tumor shrinkage of multiple myeloma subcutaneous tumors (Group B).

FIG.18B

Co-administration of eIF5A1 siRNA increases anti-tumor effect of eIF5A1$^{K50R}$ plasmid, driven by either the EF1 or B29 promoter, on multiple myeloma subcutaneous tumors and results in reduced tumor burden (KAS-SQ-5).

eIF5A1 siRNA Synergistically Increases Apoptosis Induction Resulting from Infection with Ad-eIF5A in Lung Adenocarcinoma Cells Predicted Sequence of pExp5A (3371 bp)

Single-cutting Restriction Enzyme sites are highlighted
EcoRI = GAATTC; XhoI = CTCGAG; ClaI = ATCGAT ; SpeI = ACTAGT;
HindIII = AAGCTT; NcoI = CCATGG; NheI = GCTAGC;   MluI = ACGCGT

| Sequence | Region |
|---|---|
| TTAATTAAAATTATCTCTAAGGCATGTGAACTGGCTGTCTTGGTTTTCATCTGT<br>ACTTCATCTGCTACCTCTGTGACCTGAAACATATTTATAATTCCATTAAGCTGT<br>GCATATGATAGATTTATCATATGTATTTTCCTTAAAGGATTTTTGTAAGAACTA<br>ATTGAATTGATACCTGTAAAGTCTTTATCACACTACCCAATAAATAATAAATCT<br>CTTTGTTCAGCTCTCTGTTTCTATAAATATGTACAAGTTTTATTGTTTTTAGTG<br>GTAGTGATTTTATTCTCTTTCTATATATATACACACATGTGTGCATTCATAA<br>ATATATACAATTTTTATGAATAAAAAATTATTAGCAATCAATATTGAAAACCAC<br>TGATTTTTGTTTATGTGAGCAA | βGlo<br>MAR |
| ACAGCAGATTAAAAGGAATTCTCGAGTCATCG<br>ATACTAGTGCGACCGCCAAACCTTAGCGGCCCAGCTGACAAAAGCCTGCCCTCC<br>CCCAGGGTCCCCGGAGAGCTGGTGCCTCCCCTGGGTCCCAATTTGCATGGCAGG | B29<br>promoter |
| AAGGGGCCTGGTGAGGAAGAGGCGGGGAGGGGACAGGCTGCAGCCGGTGCAGTT | EM2K |
| ACACGTTTTCCTCCAAGGAGCCTCGGACGTTGTCAAGCTTCTGCCTTCTCCCTC | I 140 |
| CTGTGAGTTTGGTAAGTCACTGACTGTCTATGCCTGGGAAAGGGTGGGCAGGAG<br>ATGGGGCAGTGCAGGAAAAGTGGCACTATGAACCCTGCAGCCCTAGGAATGCAT<br>CTAGACAATTGTACTAACCTTCTTCTCTTTCCTCTCCTGACAG | EM2K |
| GTTGGTGTACA<br>GTAGCTTCCACCATGGCAGATGATTTGGACTTCGAGACAGGAGATGCAGGGGCC<br>TCAGCCACCTTCCCAATGCAGTGCTCAGCATTACGTAAGAATGGTTTTGTGGTG<br>CTCAAGGGCCGGCCATGTAAGATCGTCGAGATGTCTACTTCGAAGACTGGCAGG<br>CATGGCCATGCCAAGGTCCATCTGGTTGGTATTGATATTTTTACTGGGAAGAAA<br>TATGAAGATATCTGCCCGTCGACTCATAACATGGATGTCCCCAACATCAAAAGG<br>AATGATTTCCAGCTGATTGGCATCCAGGATGGGTACCTATCCCTGCTCCAGGAC<br>AGTGGGGAGGTACGAGAGGACCTTCGTCTGCCTGAGGGAGACCTTGGCAAGGAG<br>ATTGAGCAGAAGTATGACTGTGGAGAAGAGATCCTGATCACAGTGCTGTCCGCC<br>ATGACAGAGGAGGCAGCTGTTGCAATCAAGGCGATGGCAAAATAA | Zeocin<br>eIF5A1$^{K50R}$ |
| CTGGCTAGC<br>TGGCCAGACATGATAAGATACATTGATGAGTTTGGACAAACCACAACTAGAATG<br>CAGTGAAAAAAATGCTTTATTTGTGAAATTTGTGATGCTATTGCTTTATTTGTA<br>ACCATTATAAGCTGCAATAAACAAGTTAACAACAACAATTGCATTCATTTTATG<br>TTTCAGGTTCAGGGGGAGGTGTGGGAGGTTTTTTAAAGCAAGTAAAACCTCTAC | SV40<br>pAn |

FIG.23A

```
                                    B29
                                   DHS4.4
              SV40                 enhancer
              pAn
    ┌─────────────────────────────────────────────────────────┐
    │AAATGTGGTATG│GCGGCCGC│ACCACCCTGGGCCAGGCTGGGCCAAGCCAGGCGG │
    │CCCCTGTGTTTTCCCCAGTCTCTGGGCTGCTGGAGGGAACCAGGTTGTTTTGGC   │
    │ATCAGCCTCTACTGAGCCGGAGCCCTTCCTTTCCTGCTGCTTTGCATAGTGGCA   │
    │CTAATTCCGTCCTCCTACCTCCACCAGGGACCTAGGCAGCCGGGTAGATGGTGG   │
    │GAGGAGGCTTCACTTCTCCCCCAAGCAGGGTCTCCACCTGCTTGAGGCTGCCCT   │
    │GGGTTGGGGGAGGCCTTGGCTTTACCTAAAGACTTTTTAACACCTCT│ACGCGT│A│
    │ATTC│AGTCAATATGTTCACCCCAAAAAAGCTGTTTGTTAACTTG│CCAACCTCAT│
    │TCTAAAATGTATATAGAAGCCCAAAAGACAATAACAAAAATATTCTTGTAGAAC   │─ I 140
    │AAAATGGGAAAGAATGTTCCACTAAATATCAAGATTTAGAGCAAAGCATGAGAT   │
    │GTGTGGGGATAGACAGTGAGGCTGATAAAATAGAGTAGAGCTCAGAAACAGACC   │
    │CATTGATATATGTAAGTGACCTATGAAAAAAATATGGCATTTTACAATGGGAAA   │
    │ATGATGATCTTTTTCTTTTTTAGAAAAACAGGGAAATATATTTATATGTAAAAA   │
    │ATAAAAGGGAACCCATATGTCATACCATACACACAAAAAAATTCCAGTGAATTA   │
    │TAAGTCTAAATGGAGAAGGCAAAACTTTAAATCTTTTAGAAAATAATATAGAAG   │
    │CATGCCATCAAGACTTCAGTGTAGAGAAAAATTTCTTATGACTCAAAGTCCTAA   │ IFNβ
    │CCACAAAGAAAAGATTGTTAATTAGATTGCATGAATATTAAGACTTATTTTTAA   │ S/MAR
    │AATTAAAAACCATTAAGAAAAGTCAGGCCATAGAATGACAGAAAATATTTGCA    │
    │ACACCCCAGTAAAGAGAATTGTAATATGCAGATTATAAAAGAAGTCTTACAAA    │
    │TCAGTAAAAAATAAAACTAGACAAAAATTTGAACAGATGAAAGAGAAACTCTAA   │
    │ATAATCATTACACATGAGAAACTCAATCTCAGAAATCAGAGAACTATCATTGCA   │
I 140│TATACACTAAATTAGAGAAATATTAAAAGGCTAAGTAACATCTGTGGCTTAATT   │─EM2K
    │AAAACAGG│TAG│TTGACAATTAAACATTGGCATAGTATATCTGCATAGTATAATA│
    │CAACTCACTATAGGAGGGCCATC│ATGGCCAAGTTGACCAGTGCTGTCCCAGTGC │
    │TCACAGCCAGGGATGTGGCTGGAGCTGTTGAGTTCTGGACTGACAGGTTGGGGT   │
    │TCTCCAGAGATTTTGTGGAGGATGACTTTGCAGGTGTGGTCAGAGATGATGTCA   │ Zeocin
    │CCCTGTTCATCTCAGCAGTCCAGGACCAGGTGGTGCCTGACAACACCCTGGCTT   │
    │GGGTGTGGGTGAGAGGACTGGATGAGCTGTATGCTGAGTGGAGTGAGGTGGTCT   │
    │CCACCAACTTCAGGGATGCCAGTGGCCCTGCCATGACAGAGATTGGAGAGCAGC   │
    │CCTGGGGGAGAGAGTTTGCCCTGAGAGACCCAGCAGGCAACTGTGTGCACTTTG   │
    │TGGCAGAGGAGCAGGACTGA│GGATAACCTAGGAAACCTTAAAACCTTTAAAAGC │
    │CTTATATATTCTTTTTTTTCTTATAAAACTTAAAAACCTTAGAGGCTATTTAAGT │ R6K
    │TGCTGATTTATATTAATTTTATTGTTCAAACATGAGAGCTTAGTACATGAAACA  │ ori
    │TGAGAGCTTAGTACATTAGCCATGAGAGCTTAGTACATTAGCCATGAGGGTTTA  │
    │GTTCATTAAACATGAGAGCTTAGTACATTAAACATGAGAGCTTAGTACATACTA  │
    │TCAACAGGTTGAACTGCTGATC                                  │
    └─────────────────────────────────────────────────────────┘
```

FIG.23B

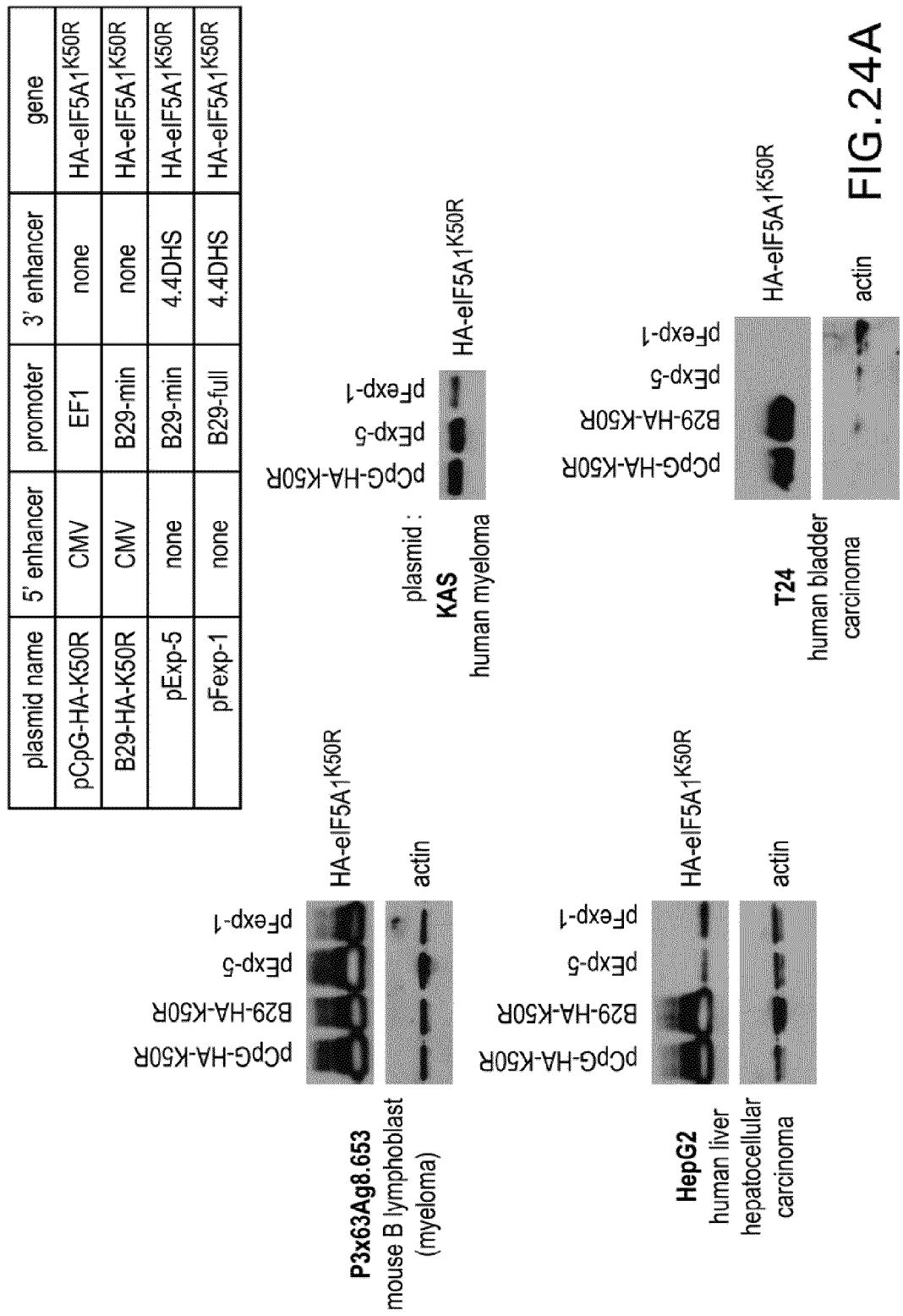

h5A1siRNA

Target sequence : 5' GCU GGA CUC CUC CUA CAC A (dTdT) 3' siRNA

5' GCU GGA CUC CUC CUA CAC A dTdT 3'
3' dTdT CGA CCU GAG GAG GAU GUGU 5'

FIG.25

Sequence of eIF5A1$^{k50R}$ cDNA

Nucleotide:

Start codon: <u>ATG</u>
Stop codon: <u>TAA</u>
HA-tag: <u>ATGTACCCATACGACGTCCCAGACTACGCT</u>

<u>AT</u>AGGGAGACCCAAGCTGGAGACC<u>ATGTACCCATACGACGTCCCAGACTACG
CT</u>GGAAGCTTA<u>ATG</u>GCAGATGATTTGGACTTCGAGACAGGAGATGCAGGGGC
CTCAGCCACCTTCCCAATGCAGTGCTCAGCATTACGTAAGAATGGTTTTGTG
GTGCTCAAGGGCCGGCCATGTAAGATCGTCGAGATGTCTACTTCGAAGACTG
GCAGGCATGGCCATGCCAAGGTCCATCTGGTTGGTATTGATATTTTTACTGG
GAAGAAATATGAAGATATCTGCCCGTCGACTCATAACATGGATGTCCCCAAC
ATCAAAAGGAATGATTTCCAGCTGATTGGCATCCAGGATGGGTACCTATCCC
TGCTCCAGGACAGTGGGGAGGTACGAGAGGACCTTCGTCTGCCTGAGGGAGA
CCTTGGCAAGGAGATTGAGCAGAAGTATGACTGTGGAGAAGAGATCCTGATC
ACAGTGCTGTCCGCCATGACAGAGGAGGCAGCTGTTGCAATCAAGGCCATGG
CAAAA<u>TAA</u>CTGGAATTC

Protein:
    HA
MYPYDVPDYAGSLMADDLDFETGDAGASATFPMQCSALRKNGFVVLKGRPCK
IVEMSTSKTGRHGHAKVHLVGIDIFTGKKYEDICPSTHNMDVPNIKRNDFQL
IGIQDGYLSLLQDSGEVREDLRLPEGDLGKEIEQKYDCGEEILITVLSAMTE
EAAVAIKAMAK

FIG.28

Alignment between human eIF5A1 and human eIF5A1^{k50R}

```
               1                                                              50
      eIF5A1   MADDLDFETG DAGASATFPM QCSALRKNGF VVLKGRPCKI VEMSTSKTGK
        K50R   MADDLDFETG DAGASATFPM QCSALRKNGF VVLKGRPCKI VEMSTSKTGR
   Consensus   MADDLDFETG DAGASATFPM QCSALRKNGF VVLKGRPCKI VEMSTSKTGr 51                                                             100
      eIF5A1   HGHAKVHLVG IDIFTGKKYE DICPSTHNMD VPNIKRNDFQ LIGIQDGYLS
        K50R   HGHAKVHLVG IDIFTGKKYE DICPSTHNMD VPNIKRNDFQ LIGIQDGYLS
   Consensus   HGHAKVHLVG IDIFTGKKYE DICPSTHNMD VPNIKRNDFQ LIGIQDGYLS 101                                                             150
      eIF5A1   LLQDSGEVRE DLRLPEGDLG KEIEQKYDCG EEILITVLSA MTEEAAVAIK
        K50R   LLQDSGEVRE DLRLPEGDLG KEIEQKYDCG EEILITVLSA MTEEAAVAIK
   Consensus   LLQDSGEVRE DLRLPEGDLG KEIEQKYDCG EEILITVLSA MTEEAAVAIK 151
      eIF5A1   AMAK
```

FIG.29

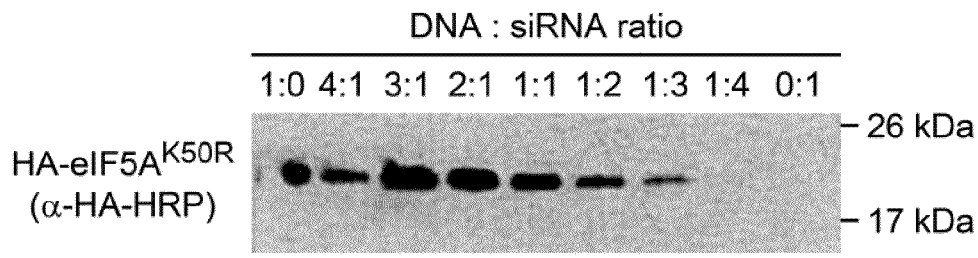

DNA : siRNA ratio

1:0  4:1  3:1  2:1  1:1  1:2  1:3  1:4  0:1

HA-eIF5A$^{K50R}$
(α-HA-HRP)

— 26 kDa
— 17 kDa

PEI Nanoparticles (N/P = 6)
1:0 = 3 µg B29-HA-eIF5A$^{K50R}$
4:1 = 2.4 µg B29-HA-eIF5A$^{K50R}$ + 0.6 µg h5A1
3:1 = 2.25 µg B29-HA-eIF5A$^{K50R}$ + 0.75 µg h5A1
2:1 = 2 µg B29-HA-eIF5A$^{K50R}$ + 1 µg h5A1
1:1 = 1.5 µg B29-HA-eIF5A$^{K50R}$ + 1.5 µg h5A1
1:2 = 1 µg B29-HA-eIF5A$^{K50R}$ + 2 µg h5A1
1:3 = 0.75 µg B29-HA-eIF5A$^{K50R}$ + 2.25 µg h5A1
1:4 = 0.6 µg B29-HA-eIF5A$^{K50R}$ + 2.4 µg h5A1
0:1 = 3 µg h5A1

B29-HA-eIF5A$^{K50R}$ : plasmid DNA B-cell specific promoter/enhancer (B29) in pCpG vector (same vector as pExp5A) expressing HA-tagged eIF5A$^{K50R}$ h5A1 : siRNA targeting human eIF5A (GLP-grade)

PEI : GLP-grade

Effect of DNA:siRNA ratio on HA-eIF5A$^{K50R}$ Expression

FIG.30

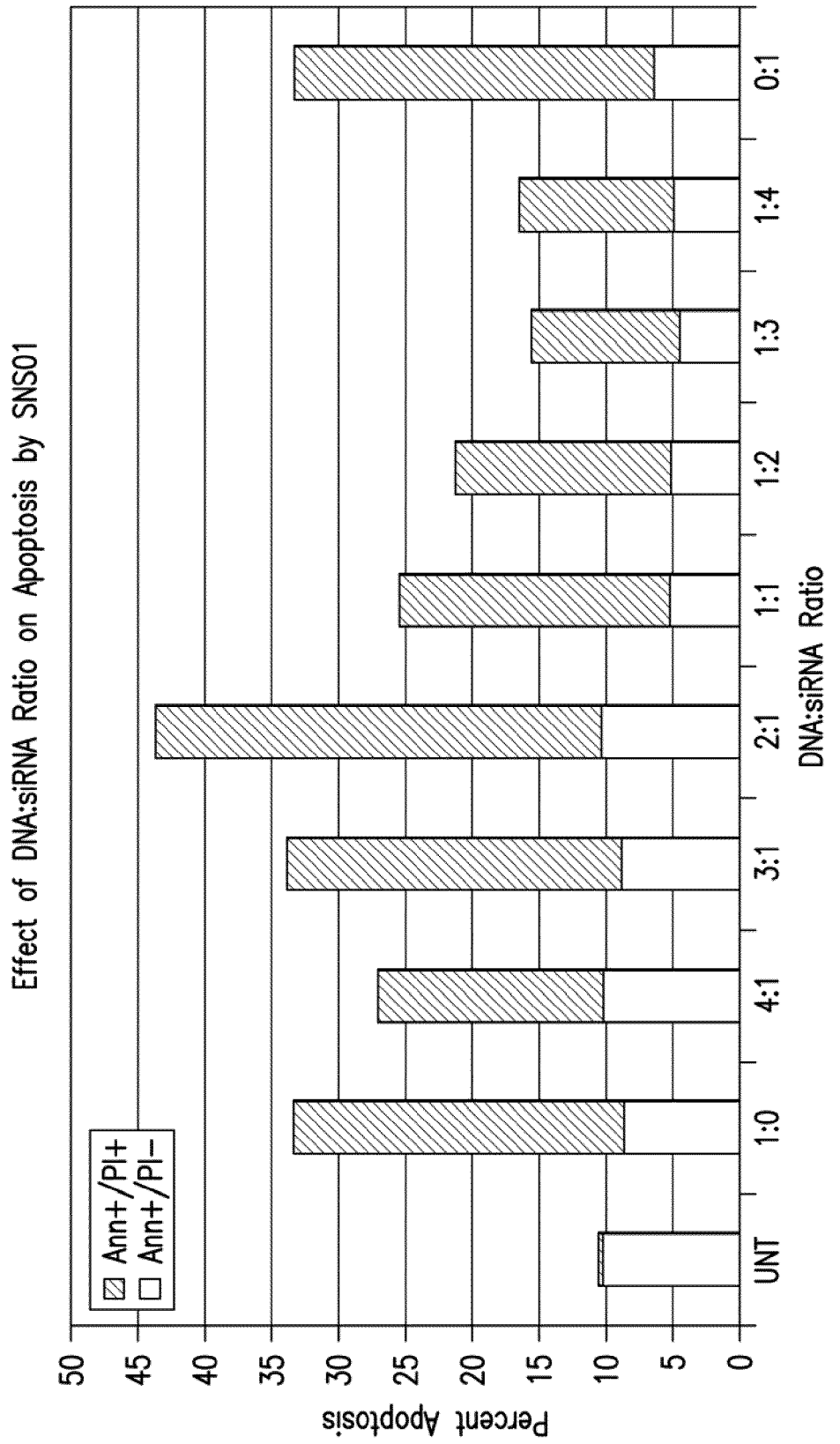

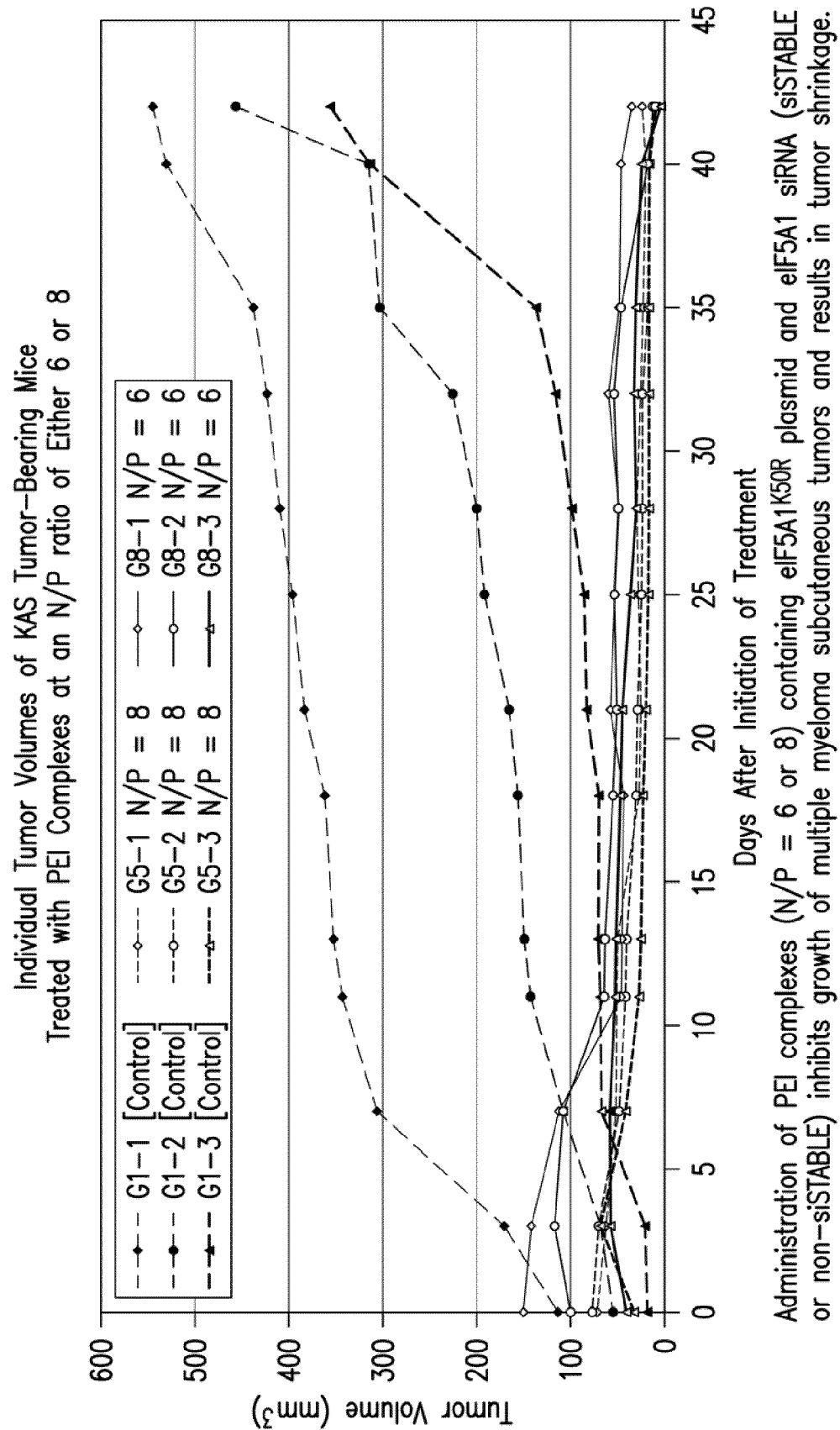

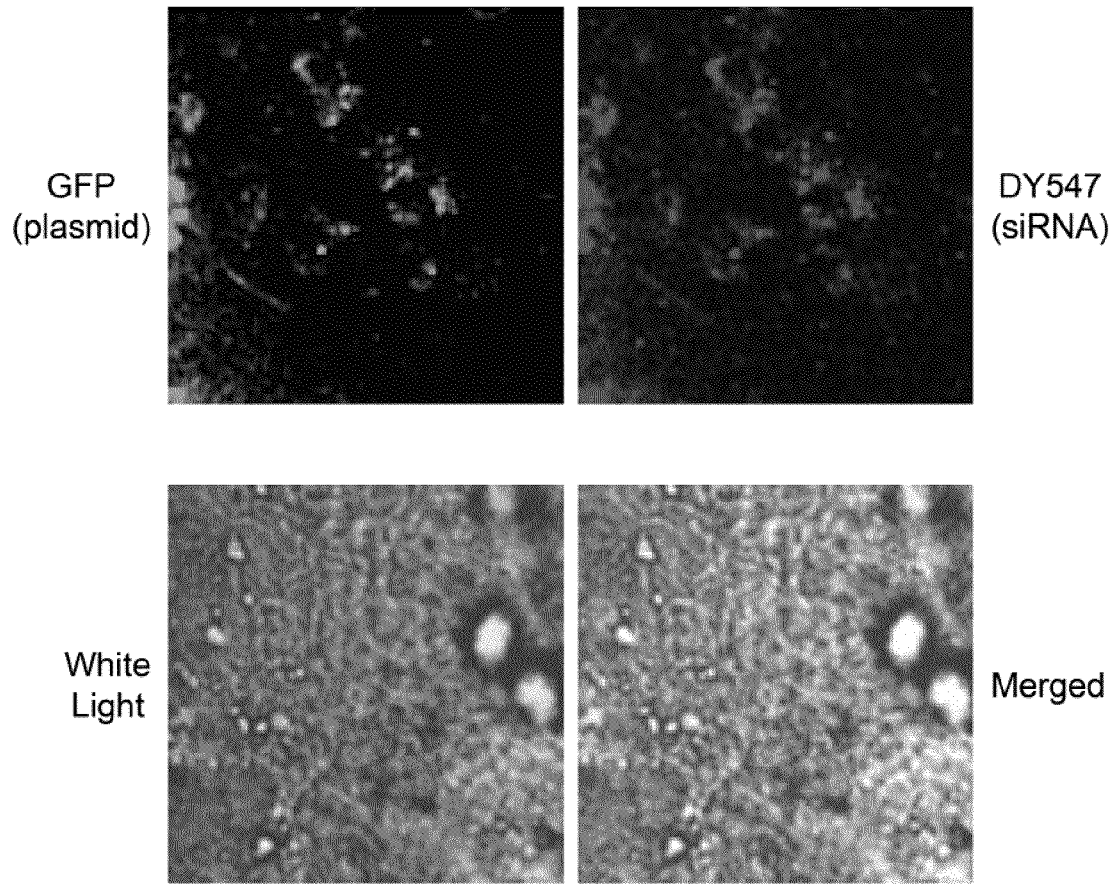

Tumour section 48 hours after injection with nanoparticles containing pExp-GFP (GFP under control of B-cell-specific promoter) and DY547-siRNA (fluorescently-labelled siRNA). Co-localized expression of GFP and DY547 is observed in tumour section following confocal microscopy indicating that the nanoparticles are being effectively taken up by tumour tissue and that nanoparticles are delivering plasmid and siRNA to the same cell.

FIG.33

COMPOSITIONS COMPRISING SIRNA AND PLASMIDS

This application claims priority to U.S. provisional application 61/034,830, which was filed on Mar. 8, 2008, and which is herein incorporated by reference in its entirety.

FIELD OF THE INVENTION

The present invention relates to the combinatorial use of siRNA targeted against a gene to knock down or knock out expression of the endogenous gene, and use of a polynucleotide encoding a exogenous gene to affect expression of that gene.

BACKGROUND OF THE INVENTION

Relatively recently, researchers observed that double stranded RNA ("dsRNA") could be used to inhibit protein expression. This ability to silence a gene has broad potential for treating human diseases, and many researchers and commercial entities are currently investing considerable resources in developing therapies based on this technology.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation.

It is generally considered that the major mechanism of RNA induced silencing (RNA interference, or RNAi) in mammalian cells is mRNA degradation. Initial attempts to use RNAi in mammalian cells focused on the use of long strands of dsRNA. However, these attempts to induce RNAi met with limited success, due in part to the induction of the interferon response, which results in a general, as opposed to a target-specific, inhibition of protein synthesis. Thus, long dsRNA is not a viable option for RNAi in mammalian systems.

More recently it has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) Ribonuclease Activity and RNA Binding of Recombinant Human Dicer, EMBO J. 21(21): 5864-5874; Tabara et al. (2002) The dsRNA Binding Protein RDE-4 Interacts with RDE-1, DCR-1 and a DexH-box Helicase to Direct RNAi in *C. elegans*, Cell 109(7):861-71; Ketting et al. (2002) Dicer Functions in RNA Interference and in Synthesis of Small RNA Involved in Developmental Timing in *C. elegans*; Martinez et al., Single-Stranded Antisense siRNAs Guide Target RNA Cleavage in RNAi, Cell 110(5):563; Hutvagner & Zamore (2002) A microRNA in a multiple-turnover RNAi enzyme complex, Science 297:2056.

From a mechanistic perspective, introduction of long double stranded RNA into plants and invertebrate cells is broken down into siRNA by a Type III endonuclease known as Dicer. Sharp, RNA interference—2001, Genes Dev. 2001, 15:485. Dicer, a ribonuclease-III-like enzyme, processes the dsRNA into 19-23 base pair short interfering RNAs with characteristic two base 3' overhangs. Bernstein, Caudy, Hammond, & Hannon (2001) Role for a bidentate ribonuclease in the initiation step of RNA interference, Nature 409:363. The siRNAs are then incorporated into an RNA-induced silencing complex (RISC) where one or more helicases unwind the siRNA duplex, enabling the complementary antisense strand to guide target recognition. Nykanen, Haley, & Zamore (2001) ATP requirements and small interfering RNA structure in the RNA interference pathway, Cell 107:309. Upon binding to the appropriate target mRNA, one or more endonucleases within the RISC cleaves the target to induce silencing. Elbashir, Lendeckel, & Tuschl (2001) RNA interference is mediated by 21- and 22-nucleotide RNAs, Genes Dev. 15:188, FIG. 1.

The interference effect can be long lasting and may be detectable after many cell divisions. Moreover, RNAi exhibits sequence specificity. Kisielow, M. et al. (2002) Isoform-specific knockdown and expression of adaptor protein ShcA using small interfering RNA, J. Biochem. 363:1-5. Thus, the RNAi machinery can specifically knock down one type of transcript, while not affecting closely related mRNA. These properties make siRNA a potentially valuable tool for inhibiting gene expression and studying gene function and drug target validation. Moreover, siRNAs are potentially useful as therapeutic agents against: (1) diseases that are caused by over-expression or misexpression of genes; and (2) diseases brought about by expression of genes that contain mutations.

Successful siRNA-dependent gene silencing depends on a number of factors. One of the most contentious issues in RNAi is the question of the necessity of siRNA design, i.e., considering the sequence of the siRNA used. Early work in *C. elegans* and plants circumvented the issue of design by introducing long dsRNA (see, for instance, Fire, A. et al. (1998) Nature 391:806-811). In this primitive organism, long dsRNA molecules are cleaved into siRNA by Dicer, thus generating a diverse population of duplexes that can potentially cover the entire transcript. While some fraction of these molecules are non-functional (i.e., induce little or no silencing) one or more have the potential to be highly functional, thereby silencing the gene of interest and alleviating the need for siRNA design. Unfortunately, due to the interferon response, this same approach is unavailable for mammalian systems. While this effect can be circumvented by bypassing the Dicer cleavage step and directly introducing siRNA, this tactic carries with it the risk that the chosen siRNA sequence may be non-functional or semi-functional.

A number of researches have expressed the view that siRNA design is not a crucial element of RNAi. On the other hand, others in the field have begun to explore the possibility that RNAi can be made more efficient by paying attention to the design of the siRNA.

To treat various diseases or disorders, the upregulation of certain proteins is desirable but this may not be all that is needed. For example, the combinatorial use of siRNA to knock down or knock out expression of an endogenous protein or a different protein may be needed. The present invention fulfills this need and provides methods of treating cancer, especially multiple myeloma.

Cancer, including multiple myeloma are diseases which would benefit from the ability to induce apoptosis. Conventional therapies for of multiple myeloma include chemotherapy, stem cell transplantation, high-dose chemotherapy with stem cell transplantation, and salvage therapy. Chemotherapies include treatment with Thalomid®(thalidomide), bortezomib, Aredia® (pamidronate), steroids, and Zometa® (zoledronic acid). However many chemotherapy drugs are toxic to actively dividing non-cancerous cells, such as of the bone marrow, the lining of the stomach and intestines, and the hair follicles. Therefore, chemotherapy may result in a decrease in blood cell counts, nausea, vomiting, diarrhea, and loss of hair.

Conventional chemotherapy, or standard-dose chemotherapy, is typically the primary or initial treatment for patients with of multiple myeloma. Patients also may receive chemotherapy in preparation for high-dose chemotherapy and stem cell transplant. Induction therapy (conventional chemotherapy prior to a stem cell transplant) can be used to reduce the tumor burden prior to transplant. Certain chemotherapy drugs are more suitable for induction therapy than others, because they are less toxic to bone marrow cells and result in a greater yield of stem cells from the bone marrow. Examples of chemotherapy drugs suitable for induction therapy include dexamethasone, thalidomide/dexamethasone, VAD (vincristine, Adriamycin® (doxorubicin), and dexamethasone in combination), and DVd (pegylated liposomal doxorubicin (Doxil®, Caelyx®), vincristine, and reduced schedule dexamethasone in combination).

The standard treatment for of multiple myeloma is melphalan in combination with prednisone (a corticosteroid drug), achieving a response rate of 50%. Unfortunately, melphalan is an alkylating agent and is less suitable for induction therapy. Corticosteroids (especially dexamethasone) are sometimes used alone for multiple myeloma therapy, especially in older patients and those who cannot tolerate chemotherapy. Dexamethasone is also used in induction therapy, alone or in combination with other agents. VAD is the most commonly used induction therapy, but DVd has recently been shown to be effective in induction therapy. Bortezomib has been approved recently for the treatment of multiple myeloma, but it is very toxic. However, none of the existing therapies offer a significant potential for a cure. Thus, there still remains a need to find a suitable treatment for cancer and multiple myeloma. The present invention fulfills this need.

SUMMARY OF INVENTION

The present invention relates to the combinatorial use of an siRNA targeted against an endogenous gene to knock out or knock down expression of the endogenous gene in a host and a delivery of a polynucleotide encoding the gene in a delivery vehicle/expression vector to the host to provide expression in the host of the protein encoded by the polynucleotide. A polynucleotide encoding a normal (non faulty) protein (or the protein itself) is administered to the host and is expressed (in the case of the polynucleotide) so that the normal protein can perform its necessary function. The siRNA is preferably designed to target a region of the gene so it either knocks down or knocks out endogenous expression of the faulty protein but at the same time will not effect exogenous expression of the administered polynucleotide encoding the normal protein.

The invention provides a composition comprising a complex of an eIF5A1 siRNA targeted against the 3' end of eIF5A1, an expression vector comprising a polynucleotide encoding a mutant eIF5A1 wherein the mutant eIF5A1 is unable to be hypusinated, and wherein the siRNA and the expression vector are complexed to polyethylenimine to form a complex.

The invention provides a composition comprising an siRNA targeted against a target gene to suppress endogenous expression of the target gene is a subject, and a polynucleotide encoding a target protein capable of being expressed in the subject. In certain embodiments the polynucleotide is in RNAi resistant plamsid (will not be suppressed by the siRNA). The siRNA and the plasmid are preferably complexed to polyethylenimine to form a complex.

In certain embodiments the siRNA has the sequence shown in FIG. 25 and wherein the polynucleotide encoding the mutant eIF5A1 is eIF5A1$^{K50R}$. The expression vector comprises the a polynucleotide encoding a mutant eIF5A1 and a promoter operably linked to provide expression of the polynucleotide in a subject. The promoter preferably is either tissue specific or systemic. For example, if the composition is used to treat cancer, then preferably the promoter is tissue specific for the tissue in which the cancer resides. For example, for treating multiple myeloma, it is preferable to use a B cell specific promoter, such as B29. In certain embodiments, the expression vector comprises a pCpG plasmid.

In certain embodiments, the eIF5A1 siRNA and the expression vector comprising the mutant eIF5A1 polynucleotide are independently complexed to polyethylenimine, such as in vivo JetPEI™. In other embodiments, the eIF5A1 siRNA and the expression vector comprising the mutant eIF5A1 polynucleotide are complexed together to polyethylenimine.

The present invention further provides a composition comprising an eIF5A1 siRNA targeted against the 3' end of eIF5A1 and an expression vector comprising a polynucleotide encoding a mutant eIF5A1 wherein the mutant eIF5A1 is unable to be hypusinated, and wherein the siRNA and the expression vector are delivered to a subject to treat cancer. The cancer may be any cancer including multiple myeloma.

The present invention further provides a method of treating cancer comprising administering composition of the present invention to a subject (including but not limited to mammals and humans).

The composition may be administered any acceptable route, such as, but not limited to intravenously, intra peritoneally, subcutaneously or intra tumorally. The siRNA and the expression vector may be administered at different times and via different routes or may be administered together at the same time and via the same route. For example, but not limited to, the siRNA may be delivered naked or complexed to a carrier such as in vivo jetPEI via IV and the expression vector may be administered intra tumorally, or both the siRNA and the expression vector may be administered IV or intratumorally, etc.

The present invention provides a method of inhibiting cancer cell growth and/or killing cancer cells. The present invention also provides a method of inhibiting or slowing down the ability of a cancer cell to metastasize. Inhibiting cancer growth includes a reduction in the size of a tumor, a decrease in the growth of the tumor, and can also encompass a complete remission of the tumor. The cancer can be any cancer or tumor, including but not limited to colon cancer, colorectal adenocarcinoma, bladder carcinoma, cervical adenocarcinoma, and lung carcinoma. Preferably the cancer is multiple myeloma.

In preferred embodiments, the eIF-5A is a mutant that is unable to be hypusinated. Exemplary mutants are described herein.

In addition to providing eIF-5A or a polynucleotide encoding eIF-5A to a subject (to provide expression of the eIF-5A), siRNA is provided to knock out or knock down endogenous expression of eIF-5A.

The present invention also provides the use of eIF5A, polynucleotides encoding eIF5A1 and siRNA against eIF5A1 to make a medicament to treat acner kill multiple myeloma cells in a subject having multiple myeloma. Preferably the polynucleotides encoding a mutant eIF-5A are unable to be hypusinated.

The present invention also provides a method of treating sickle cell anemia. A polynucleotide encoding a healthy hemoglobin gene (such as HBB) is administered to a patient suffering from sickle cell anemia. In conjunction, the patient is also administered siRNA that targets the gene encoding the faulty hemoglobin gene (such as the gene encoding the mutant HbS) to knock down or knock out expression of the faulty protein. The treatment may further comprise administration of other known medicines or treatments commonly used in treating sickle cell anemia.

BRIEF DESCRIPTION OF THE FIGURES

FIG. 1 provides the amino acid sequence of human eIF-5A1 (SEQ ID NO: 19) and shows various important sites. PHM6-eIF5A1 and Consensus sequence each disclosed as SEQ ID NO: 29.

FIG. 13A shows that treatment with eIF5A1 plasmid and eIF5A1 siRNA delays growth of multiple myeloma subcutaneous tumours and results in tumour shrinkage.

FIG. 18 shows that administration of eIF5A1 siRNA intravenously (i.v.) and PEI/eIF5A1K50R plasmid complexes intra-tumourally (i.t.) results in tumour shrinkage of multiple myeloma subcutaneous tumours. See example 13.

FIG. 23 shows the predicted sequence of pExp5A (3371 bp (SEQ ID NO: 30)). See example 17.

FIG. 25 shows the target sequence (SEQ ID NO: 31) and the sequence of a preferred eIF5A1 siRNA (SEQ ID NOS 31 and 32, respectively, in order of appearance).

FIG. 28 provides the sequence of eIF-5A1$^{k50R}$ cDNA (SEQ ID NO: 33) and protein (SEQ ID NO: 34). FIG. 28 also discloses the HA-tag as residues 25-54 of SEQ ID NO: 33.

FIG. 29 provides the alignment of human eIF-5A1 (SEQ ID NO: 19) against human eIF5A1$^{k50R}$ (SEQ ID NO: 6). The Consensus sequence is disclosed as SEQ ID NO: 6.

FIG. 30 shows the effect of DNA:siRNA ratio on HA-eIF5A$^{K50R}$ expression. See example 23.

FIG. 31 shows the effect of DNA:siRNA ratio on apoptosis induced by nanoparticle transfection. See example 24.

FIG. 32 shows administration of PEI complexes (N/P=6 or 8) containing eIF5A1K50R plasmid and eIF5A1 siRNA (siS-TABLE or non-siSTABLE) inhibits growth of multiple myeloma subcutaneous tumours and results in tumour shrinkage. See example 25.

FIG. 33 shows that the JET PEI™ nanoparticles are being effectively taken up by tumour tissue and that nanoparticles are delivering plasmid and siRNA to the same cell. See example 26.

DETAILED DESCRIPTION OF THE INVENTION

Figure 2A:
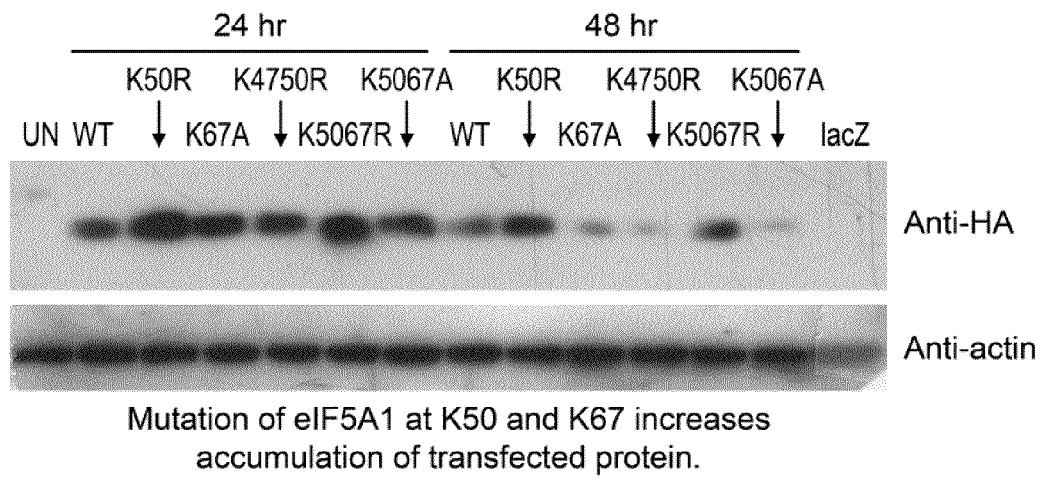
FIG. 2 shows that mutation of eIF5A1 at K50 and K67 increases accumulation of transfected protein. See example 1.

The present invention relates to the combinatorial use of an siRNA targeted against an endogenous gene to knock out or knock down expression of the endogenous gene in a subject and a of a polynucleotide encoding the gene in a delivery vehicle/expression vector provided to the subject to provide expression in the host of the protein encoded by the polynucleotide.

This combination is useful in treating a subject with a disease or condition caused by the existence of a faulty or mutant protein, i.e. where the protein produced in the subject is unable to perform it necessary function or alternatively, fowls up a metabolic pathway or biomolecule interaction because of its faulty structure. The siRNA is designed to target the gene encoding the faulty protein, and knock down or knock out expression of that faulty protein. A polynucleotide encoding a normal (non faulty) protein is administered to the subject and is expressed in the subject so that the normal protein is available to perform its necessary function.

In another embodiment, instead of administering the polynucleotide encoding the desired protein, the protein is administered to the subject. The terms protein, peptide and polypeptide are used herein interchangeably.

The siRNA is preferably designed to target a certain region of the gene so it either knocks down or knocks out endogenous expression of the faulty protein but at the same time will not effect exogenous expression of the administered polynucleotide encoding the normal protein. For example, the siRNA may target the 3'UTR so it does not effect exogenous expression of the administered sense construct (the polynucleotide encoding the protein). By knocking down or knocking out endogenous expression of the faulty gene, there will be less or none of the faulty protein to compete with the normal protein expressed from the exogenous polynucleotide.

One example of a disease state where this application would be useful concerns sickle cell anemia. Sickle cell anemia is a blood disorder that affects hemoglobin, the protein found in red blood cells (RBCs) that helps carry oxygen throughout the body.

Sickle cell anemia occurs when a person inherits two abnormal genes (one from each parent) that results in expression of a mutant hemoglobin (Hbs). The mutant hemoglobin causes the RBCs to change shape. Red blood cells with normal hemoglobin (hemoglobin A, or HbA) move easily through the bloodstream, delivering oxygen to all of the cells of the body. They can easily "squeeze" through even very small blood vessels. Sickle cell anemia occurs because the abnormal form of hemoglobin (HbS) tends to clump together, making red blood cells sticky, stiff, and more fragile, and causing them to form into a curved, sickle shape.

Although several hundred HBB gene variants are known, sickle cell anemia is most commonly caused by the hemoglobin variant HbS. In this variant, the hydrophobic amino acid valine takes the place of hydrophilic glutamic acid at the sixth amino acid position of the HBB polypeptide chain. This substitution creates a hydrophobic spot on the outside of the protein structure that sticks to the hydrophobic region of an adjacent hemoglobin molecule's beta chain. This clumping together (polymerization) of HbS molecules into rigid fibers causes the "sickling" of red blood cells.

Polymerization occurs only after red blood cells have released the oxygen molecules that they carry to various tissues throughout the body. Once red blood cells return to the lungs where hemoglobin can bind oxygen, the long fibers of HbS molecules depolymerize or break apart into single molecules. Cycling between polymerization and depolymerization causes red blood cell membranes to become rigid. The rigidity of these red blood cells and their distorted shape when they are not carrying oxygen can result in blockage of small blood vessels. This blockage can cause episodes of pain and can damage organs.

Sickle cell anemia is an autosomal recessive genetic disorder. For the disease to be expressed, a person must inherit either two copies of HbS variant or one copy of HbS and one copy of another variant. Carriers, who have one copy of the normal HBB gene (HbA) and one copy of HbS, are described as having sickle cell trait and do not express disease symptoms.

Thus, one embodiment of the present invention provides a method of treating subjects with sickle cell anemia. siRNA targeted to the HBB gene is administered to the patient. The siRNA is designed to knock down and preferably knock out the expression of the Hbs variant of hemoglobin. A polynucleotide encoding a normal hemoglobin is provided to the subject so the subject expresses a normal hemoglobin. The siRNA is also designed so that it will not interfere with expression of the exogenous polynucleotides encoding the normal hemoglobin. Thus, the subject no longer makes the variant hemoglobin (or makes substantially less) and instead makes normal healthy hemoglobin, resulting in more normal red blood cells, which function normally.

The present invention is also useful in situations where a post translational modification occurs to the protein, which causes or leads to a disease state. siRNA is used to knock down expression of the endogenous protein so none or less is available for the post translational modification. Then, a polynucleotide encoding a protein is provided to the patient for exogenous expression. The protein is modified so that it is unable to be post translationally modified. This protein is then available to the body for its appropriate use, but will not lead to the disease state because it is not able to be post translationally modified. One skilled in the art would understand different post translational modifications. For example, after translation, the posttranslational modification of amino acids extends the range of functions of the protein by attaching to it other biochemical functional groups such as acetate, phosphate, various lipids and carbohydrates, by changing the chemical nature of an amino acid (e.g. citrullination) or by making structural changes, like the formation of disulfide bridges. Also, enzymes may remove amino acids from the amino end of the protein, or cut the peptide chain in the middle. For instance, the peptide hormone insulin is cut twice after disulfide bonds are formed, and a propeptide is removed from the middle of the chain; the resulting protein consists of two polypeptide chains connected by disulfide bonds. Also, most nascent polypeptides start with the amino acid methionine because the "start" codon on mRNA also codes for this amino acid. This amino acid is usually taken off during post-translational modification. Other modifications, like phosphorylation, are part of common mechanisms for controlling the behavior of a protein, for instance activating or inactivating an enzyme. Another post translational modification includes the hypusination of eukarotic initiation factor 5A (eIF5A) by deoxyhypusine synthase (DHS).

Thus, the invention provides a method of altering expression of a gene in a subject, wherein a polynucleotide encoding a protein is provided to a patient and is expressed in the patient. The protein may be a normal/wild type protein or a mutated protein. Expression of the corresponding endogenous gene is suppressed with the siRNA that is administered to the subject.

The method further comprises providing a construct comprising a polynucleotide encoding the target protein wherein the polynucleotide is expressed in the subject to produce the target protein. In certain embodiments where the endogenous gene expresses a faulty protein, the polynucleotide is designed to encode either a normal/healthy protein. The siRNA is administered to suppress expression of the faulty endogenous protein. In certain embodiments where the endogenous gene expresses a normal healthy protein, the polynucleotide is designed to encode a mutant protein that can not be postranslationally modified as would occur with a normal/healthy or non mutant protein. The siRNA is administered to suppress expression of the endogenous protein so there is less of this protein to be available for posttranslational modification.

In certain embodiments, the siRNA is chosen or designed to target regions of the gene so as to not effect expression of the exogenous polynucleotide. For example, the siRNA may target the 3' UTR or 3' end.

The siRNA may be delivered to the patient as either naked siRNA or naked siRNA stabilized for serum. The siRNA may by either injected systemically, i.e. IP or IV. Alternatively, the siRNA may be injected or delivered locally to the desired area of the body. In certain embodiments, the siRNA may be administered in a delivery vehicle such as but not limited to dendrimers, liposomes, or polymers.

The polynucleotides encoding the desired protein may be administered through any delivery means that provide or allow expression of the nucleotide. The term polynucleotide and nucleotide are used herein interchangeably. Delivery may be through any viral or non-viral mechanism, such as but not limited to plasmids, expression vectors, viral constructs, adenovirus constructs, dendrimers, liposomes, or polymers.

In certain embodiments an expression plasmid having reduced CpG dinucleotides is used to express the polynucleotides. Any promoter capable of promoting expression of the polynucleotide may be used, which may be chosen based on the application desired for the therapy. For example, for killing multiple myeloma, a promoter specific for B cells may be desirable, such as human B29 promoter/enhancer. In other embodiments, the promoter may be another tissue specific promoter, or may be a system promoter.

The polynucleotides encoding the target protein may be delivered through IV or subcutaneous injection or any other biologically suitable delivery mechanism.

Alternatively, the polynucleotides may be delivered in liposomes or any other suitable "carrier" or "vehicle" that provides for delivery of the DNA (or plasmid or expression vector) to the target tumor or cancer cells. See for example, Luo, Dan, et al., Nature Biotechnology, Vol. 18, January 2000, pp. 33-37 for a review of synthetic DNA delivery systems. Thus, it may be preferable to deliver the nucleotides/plasmid/expression vector via a vehicle of nanometer size such as liposomes, dendrimers or a similar non-toxic nanoparticle. The vehicle preferably protects the nucleotides/plasmid/expression vector from premature clearance or from causing an immune response while delivering an effective amount of the nucleotides/plasmid/expression vector to the subject, tumor or cancer cells. Exemplary vehicles may range from a simple nano-particle associated with the nucleotides/plasmid/expression vector to a more complex pegylated vehicle such as a pegylated liposome having a ligand attached to its surface to target a specific cell receptor.

Liposomes and pegylated liposomes are known in the art. In conventional liposomes, the molecules to be delivered (i.e. small drugs, proteins, nucleotides or plasmids) are contained within the central cavity of the liposome. One skilled in the art would appreciate that there are also "stealth," targeted, and cationic liposomes useful for molecule delivery. See for example, Hortobagyi, Gabriel N., et al., J. Clinical Oncology, Vol. 19, Issue 14 (July) 2001:3422-3433 and Yu, Wei, et al., Nucleic Acids Research. 2004, 32(5);e48. Liposomes can be injected intravenously and can be modified to render their surface more hydrophilic (by adding polyethylene glycol ("pegylated") to the bilayer, which increases their circulation time in the bloodstream. These are known as "stealth" liposomes and are especially useful as carriers for hydrophilic (water soluble) anticancer drugs such as doxorubicin and mitoxantrone. To further the specific binding properties of a drug carrying liposome to a target cell, such as a tumor cell, specific molecules such as antibodies, proteins, peptides, etc. may be attached on the liposome surface. For example, antibodies to receptors present on cancer cells maybe used to target the liposome to the cancer cell. In the case of targeting multiple myeloma, folate, Il-6 or transferring for example, may be used to target the liposomes to multiple myeloma cells.

Dendrimers are also known in the art and provide a preferable delivery vehicle. See for example Marjoros, Istvan, J., et al, "PAMAM Dendrimer-Based Multifunctional Conjugate for Cancer Therapy: Synthesis, Characterization, and Functionality," Biomacromolecules, Vol. 7, No. 2, 2006; 572-579, and Majoros, Istvan J., et al., J. Med. Chem, 2005. 48, 5892-5899 for a discussion of dendrimers.

In a preferred embodiment, the delivery vehicle comprises a polyethylenimine nanoparticle. An exemplary polyethylenimine nanoparticle is the in vivo-jetPEI™, currently produced by Polyplus Transfection, Inc. In vivo-jetPEI™ is cationic polymer transfection agent useful as a DNA and siRNA delivery agent. In vivo-jetPEI™ from Polyplus Transfection is a linear polyethylenimine reagent that provides reliable nucleic acid delivery in animals. It is used for gene therapy (Ohana et al., 2004. Gene Ther Mol Bio 8:181-192; Vernejoul et al., 2002. Cancer Research 62:6124-31), RNA interference, (Urbain-Klein et al., 2004. Gene therapy 23:1-6; Grezelinski et al., 2006. Human Gene Therapy 17:751-66), and genetic vaccination (Garzon et al., 2005. Vaccine 23:1384-92). In vivo JET-PEI is currently in use in human clinical trials as a delivery vector for cancer gene therapy (Lemkine et al., 2002. Mol. Cell. Neurosci. 19:165-174).

In vivo-jetPEI™ condenses nucleic acids into roughly 50 nm nanoparticles, which are stable for several hours. As a result of this unique protection mechanism, aggregation of blood cells following injection is reduced compared to other reagents thereby preventing restricted diffusion within a tissue, erythrocyte aggregation and microembolia. These nanoparticles are sufficiently small to diffuse into the tissues and enter the cells by endocytosis. In vivo-jetPEI™ favors nucleic acids release from the endosome and transfer across of the nuclear membrane.

In a preferred embodiment, both the siRNA and a vector/plasmid comprising the polynuncleotide are administered to the subject via an in vivo-jetPEI™ complex. The siRNA and the vector/plasmid comprising the polynucleotide maybe complexed together via a polymer complex such as polyethylenimine or the in vivo jetPEI™ complex or may separately complexed to a polymer. For instance, where the siRNA and the vector/plasmid comprising the polynucleotide are to be administered separately to the subject (separately in the meaning of time and/or delivery site) it is preferable to have the siRNA and the polynucleotide complexed to a different carrier. Where the administration will be at the same time and at the same site, it may be preferable to complex the siRNA and the polynucleotide together.

In another embodiment, instead of a plasmid or vector being administered to deliver a polynucleotide that will be expressed in the subject, the protein per se is delivered to the subject. The protein may be either isolated or may be synthetic.

One embodiment of the present invention provides a method of treating cancer in a subject, including mammals and humans. Treating cancer includes, but is not limited to inducing apoptosis in cancer cells, killing cancer cells, reducing the number of cancer cells and reducing tumor volume/weight. The method comprises administering a composition comprising eIF5A1 siRNA and a polynucleotide encoding a mutant eIF5A1. The composition and eIF5A1 siRNA and a polynucleotide encoding a mutant eIF5A1 are discussed herein below.

All cells produce eukaryotic initiation factor 5A ("eIF-5A") (or also referred to herein as "factor 5A"). Mammalian cells produce two isoforms of eIF-5A1 (eIF-5A1 and eIF-5A2). eIF-5A1 has been referred to as apoptosis-specific eIF-5A, as it is upregulated in cells undergoing apoptosis. Human eIF-5A1 has the accession number NM 001970 and is shown in FIG. 1. It is believed that eIF-5A1 is responsible for shuttling out of the nucleus subsets of mRNAs encoding proteins necessary for apoptosis. eIF-5A2 has been referred to as proliferation eIF-5A as it is believed to be responsible for shuttling out of the nucleus subsets of mRNAs encoding proteins necessary for cellular proliferation. See Liu & Tartakoff (1997) Supplement to Molecular Biology of the Cell, 8, 426a. Abstract No. 2476, 37th American Society for Cell Biology Annual Meeting, and Rosorius et al. (1999) J. Cell Science, 112, 2369-2380.

Both factor 5As are post translationally modified by deoxyhypusine synthase ("DHS"). DHS hypusinates the eIF-5As. Hypusine, a unique amino acid, is found in all examined eukaryotes and archaebacteria, but not in eubacteria, and eIF-5A is the only known hypusine-containing protein. Park (1988) J. Biol. Chem., 263, 7447-7449; Schumann & Klink (1989) System. Appl. Microbiol., 11, 103-107; Bartig et al. (1990) System. Appl. Microbiol., 13, 112-116; Gordon et al. (1987a) J. Biol. Chem., 262, 16585-16589. Hypusinated eIF-5A is formed in two post-translational steps: the first step is the formation of a deoxyhypusine residue by the transfer of the 4-aminobutyl moiety of spermidine to the α-amino group of a specific lysine of the precursor eIF-5A catalyzed by deoxyhypusine synthase. The second step involves the hydroxylation of this 4-aminobutyl moiety by deoxyhypusine hydroxylase to form hypusine.

The amino acid sequence of eIF-5A is well conserved between species, and there is strict conservation of the amino acid sequence surrounding the hypusine residue in eIF-5A, which suggests that this modification may be important for survival. Park et al. (1993) Biofactors, 4, 95-104. This assumption is further supported by the observation that inactivation of both isoforms of eIF-5A found to date in yeast, or inactivation of the DHS gene, which catalyzes the first step in their activation, blocks cell division. Schnier et al. (1991) Mol. Cell. Biol., 11, 3105-3114; Sasaki et al. (1996) FEBS Lett., 384, 151-154; Park et al. (1998) J. Biol. Chem., 273, 1677-1683. However, depletion of eIF-5A protein in yeast resulted in only a small decrease in total protein synthesis suggesting that eIF-5A may be required for the translation of specific subsets of mRNA's rather than for protein global synthesis. Kang et al. (1993), "Effect of initiation factor eIF-5A depletion on cell proliferation and protein synthesis," in Tuite, M. (ed.), Protein Synthesis and Targeting in Yeast, NATO Series H. The recent finding that ligands binding eIF-5A share highly conserved motifs also supports the importance of eIF-5A. Xu & Chen (2001) J. Biol. Chem., 276, 2555-2561. In addition, the hypusine residue of modified eIF-5A was found to be essential for sequence-specific binding to RNA, and binding did not provide protection from ribonucleases.

The present inventors have shown that when polynucleotides encoding eIF-5A are administered to cells, there is an increase in apoptosis those cells. They have shown that they have been able to push cancer cells into apoptosis by administering eIF-5A1 polynucleotides that are then expressed in the cancer cells. See co-pending application Ser. Nos. 10/200, 148; 11/287,460; 11/293,391 and 11/637,835, all of which are incorporated by reference in their entireties.

The present inventors have additionally determined that when cells have a build up of the hypusinated form of factor 5A, the cells enter into a survival mode and do not undergo apoptosis as they normally would over time. Notably, in cancer cells, there is a significant amount of hyspusinated factor 5A and thus, the cells do not enter into apoptosis (and do not die). Thus, to treat cancer by killing the cancer cells (push the cancer cells to enter into the apoptosis pathway), a polynucleotide encoding eIF-5A1 is administered to the subject or to the cancer cells or tumor to provide increased expression of eIF-5A1, which in turn causes apoptosis in the cancer cells and ultimately cell death and tumor shrinkage. However, if one were to only provide polynucleotides encoding the eIF-5A1 protein to up regulate gene expression of eIF-5A1 and not also use siRNA to knock down endogenous expression of eIF-5A1, there is a tug of war: the eIF-5A1 expression directing the cells towards the apoptosis pathway competes with the presence of the hypusinated factor 5A directing the cells towards the cell survival pathway. The present invention eliminates this tug of war and represents an improvement over only increasing expression of eIF-5A1. The polynucleotides administered to the subject or cell are mutated so that the resulting expressed protein can not be hypusinated. In addition endogenous expression of factor 5A is knocked out/down with siRNA targeted against eIF-5A so there is none/less endogenous eIF-5A1 around to by hypusinated. Thus, since there is no (or substantially less) hypusinated eIF-5A in the cells, they are not pushed into survival mode.

The polynucleotide encoding a mutated eIF-5A1 is preferably mutated so that it can not be hypusinated and thus will not be available to drive the cell into survival mode. For example, in one embodiment, the polynucleotide encoding eIF-5A is mutated to so that the lysine (K) at position 50, which is normally hypusinated by DHS, is changed to an alanine (A) (which can not be hypusinated). This mutant is denoted as K50A.

In another embodiment, the lysine at position 67 is changed to an arginine (R). This mutant is denoted as (K67R). In another embodiment the lysine (K) at position 67 is changed to an alanine (A) and is denoted as (K67A). In another embodiment, the lysine (K) at position 50 is changed to an arginine (K50R) and another embodiment provides a mutant where the lysine (K) at position 47 is changed to an arginine (K47R).

In other embodiments, a double mutant is used. One double mutant is where the lysine (K) at position 50 is changed to an arginine (R) and the lysine (K) at position 67 is changed to a arginine (R). This double mutant is referred to as K50R/K67R. This double mutant is similarly unable to be hypusinated but the changes in the amino acids do not alter the 3-D structure of eIF-5A1 as much as the single mutation (K50A). The double mutation thus provides a protein that is very similar in 3-D shape and folding as the wild type and thus is more stable than the single mutant. Being more stable, it exists longer in the body to provide longer therapeutic benefit. Thus, the body will have the factor 5A it needs for normal cell function but it will not be able to hypusinated so the cells do not get locked into the cell survival mode and escape apoptosis.

Another double mutant is where the lysine (K) at position 47 is changed to an arginine (R) and the lysine at position 50 is changed to an arginine (R). This mutant is denoted as (K47R/K50R). The invention provides another double mutant where the lysine (L) at position 50 is changes to an alanine (A) and the lysine at position 67 is changes to an alanine (A). This mutant is denoted as (K50A/K67A).

Because the body needs factor 5A for normal cell survival and healthy cell proliferation, it is preferable not to shut off expression completely in the subject with the siRNA, if the siRNA is delivered systemically. Control of eIF-5A expression can be achieved by either using an siRNA that is not as good at shutting off expression (i.e. shuts down or reduces expression but does not completely shut off expression) or alternatively, or utilizing a dosing and/or treatment regimen to balance expression levels to allow normal growth and functioning of healthy cells but also to push cancerous cells to apoptosis.

Alternatively, one may utilize local delivery of siRNA. If the siRNA is delivered locally to the cancer cell or tumor, then the expression is preferably knocked out. By knocking out expression, there is no factor 5A around that can be hypusinated and thus there is no hypusinated eIF-5A to lock the cells into survival mode. Since the siRNA is delivered locally to the cancer or tumor, there is no need to have eIF-5A available for regular cell growth.

In certain embodiments, the endogenous gene is eIF5A1. siRNA targeted against eIF5A1 is administered to the subject to suppress expression of the endogenous eIF-5A1. In certain embodiments the siRNA comprises SEQ ID NO:1 or SEQ ID NO:2 or is any siRNA targeted against eIF5A1 that will suppress expression of endogenous eIF-5A1. In certain embodiments, the eIF5A1 is human eIF-5A1 (shown in FIG. 1) and the subject is a human. Other siRNAs targeted against human eIF-5A1 are known and disclosed in co-pending application Ser. Nos. 11/134,445; 11/287,460; 11/184,982; 11/293,391; 11/725,520; 11/725,470; 11/637,835. In other embodiments, the subject is a mammal and the eIF5A1 is specific to the mammal. For example, the subject is a dog and the eIF5A1 is canine eIF5A1. In certain embodiments, the siRNA consists essentially of the siRNA construct shown in FIG. 25. For example, the siRNA contains nucleic acids targeted against the eIF5A1 but also contains overhangs such as U or T nucleic acids or also contains tags, such as a his tag (often referred to as HA tag—which is often used in in vito studies). Molecules or additional nucleic acids attached at either the 5' or 3' end (or even within the consecutive string of nucleic acids shown in FIG. 25, for example) may be included and fall within the "consisting essentially of" as long as the siRNA construct is able to reduce expression of the target gene. Preferably the siRNA targets regions of the eIF5A1 gene so as to not effect expression of the exogenous polynucleotide. For example the eIF5A1 siRNA targets the 3' UTR or the 3' end. The siRNA shown in FIG. 25 an exemplary eIF5A1 siRNA.

The polynucleotide encodes eIF5A1 wherein the polynucleotide is mutated to encode an eIF5A1 variant. The mutated eIF5A1 is designed so that the variant eIF5A1 can not be post translationally modified (can not be hypusinated). Exemplary mutants are discussed herein above.

In the case of cancer involving solid tumors, it may be desirable to deliver the siRNA directly to the tumor. The siRNA maybe administered separately with respect to time as well as the delivery site from the polynucleotide or may administered together at the same time and/or at the same delivery site. One skilled in the art would understand that the timing of administration of the siRNA may be necessarily administered when the endogenous protein is being translated and not after it is already made.

Although the present inventors have earlier shown that eIF5A1 is non toxic to normal tissue (see pending application Ser. No. 11/293,391, filed Nov. 28, 2005, which is incorporated herein by reference in its entirety), a delivery complex (as compared to direct administration of the eIF5A polynucleotides/plasmid/expression vector) may be preferred. A preferred delivery system provides an effective amount of eIF5A1 to the subject, tumor or group of cancer cells, as well as preferably provides a targeted delivery to the tumor or group of cancer cells. Thus, in certain embodiments, it is preferable to deliver the eIF5A1 nucleotides/plasmid/expression vector via a vehicle of nanometer size such as liposomes, dendrimers or a similar non-toxic nano-particle such as a polyethylenimine polymer (such as an in vivo JetPEI™ complex).

The eIF5A1 protein may also be delivered directly to the site of the tumor. One skilled in the art would be able to determine the dose and length of treatment regimen for delivery of eIF5A1 protein.

The molecular basis for the induction of apoptosis by eIF5A1 is discussed below.

Death Receptor Signaling

Treatment of cancer cells with Ad-eIF5A1 (adenovirus with a wild type eIF5A1) or Ad-eIF5A1(K50A) induces activation of caspase 8, which is initiated by death receptor—ligand binding, and caspase 3, the executioner caspase. These are likely to be indirect effects of eIF5A1, and the fact that caspase 8 and caspase 3 are also activated following treatment with eIF5A1(K50A), which cannot be hypusinated, indicates that the effect is attributable to lysine$_{50}$ eIF5A1. Treatment with Ad-eIF5A1 also appears to result in up-regulation of death receptors as shown previously with upregulation of TNFR1.

Mitochondrial Pathway

Direct or indirect involvement of lysine$_{50}$ eIF5A1 in the mitochondrial pathway for apoptosis is supported by a number of observations including the finding that caspase 9 is activated by treatment of cancer cells with either eIF5A1 or eIF5A1(K50A). As well, p53, which plays a role in activation of the mitochondrial apoptotic pathway, appears to be regulated by eIF5A1. For example, treatment of cancer cells with Actinomycin D up-regulates p53, and this up-regulation of p53 is inhibited by eIF5A1 siRNA. Consistent with this, treatment of cancer cells with Ad-eIF5A1 up-regulates p53 mRNA. Treatment of cancer cells with eIF5A1 also induces migration of Bax from the cytosol to mitochondria, ensuing loss of mitochondrial membrane potential and release of cytochrome C from the intramitochondrial space into the cytosol. In addition, this treatment results in up-regulation of cleaved Bcl2, Bim and spliced Bim, which are all pro-apoptotic.

MAPK Signaling

In addition, the present inventors have obtained evidence for the involvement of eIF5A1 in MAPK signaling related to apoptosis. For example, treatment of cancer cells with Ad-eIF5A1 up-regulated P-JNK, which in turn inhibits anti-apoptotic Bcl2. In addition Ad-eIF5A1 and Ad-eIF5A1 (K50A) both induce the formation of P-p38, which can in turn initiate apoptosis by impacting a variety of pro-apoptotic agents including TNFR1 & TNF; FAS & FASL; caspase 8; Bid; Cytochrome C and Capase 3.

NF-κB Signaling

There is evidence that NF-κB signaling supports myeloma growth. For example, myeloma cell adhesion to bone marrow stromal cells induces NF-κB-dependent transcriptional up-regulation of IL-6, which is both a growth and anti-apoptotic factor in multiple myeloma [Chauhan et al. (1996) *Blood* 87, 1104.] In addition, TNF-α secreted by myeloma cells activates NF-κB in bone marrow stromal cells, thereby up-regulating IL-6 transcription and secretion. TNF-α also activates NF-κB in myeloma cells resulting in up-regulation of the intracellular adhesion molecule-1 (ICAM-1; CD54) and the vascular cell adhesion molecule-1 (VCAM-1; CD106) on both myeloma cells and bone marrow stromal cells [Hideshima et al. (2001) *Oncogene* 20, 4519]. This in turn enhances the association of myeloma cells with bone marrow stromal cells [Hideshima et al. (2001) *Oncogene* 20, 4519]. Conversely, these effects are inhibited by blocking TNFα-induced NF-κB activation [Hideshima et al. (2001) *Oncogene* 20, 4519]. Indeed, it seems likely that NF-κB mediates protection against TNFα-induced apoptosis in myeloma cells [Hideshima et al. (2002) *JBC* 277, 16639]. These and other observations have prompted the view that NF-kB signaling may be an attractive target for multiple myeloma therapies.

The inventors have shown that eIF5A1 siRNA inhibits both the activation of NF-κB and the formation of ICAM-1 in human myeloma cells. These observations indicate that eIF5A1 plays a role in NF-κB activation, and inasmuch as the ensuing effects of NF-κB activation are pro-survival in nature, we predict that this activation is mediated, directly or indirectly, by hypusinated eIF5A1.

IL-1

Over-production of the pro-inflammatory cytokine, IL-1, by myeloma cells is a characteristic feature of multiple myeloma that leads to deterioration of bone tissue. eIF5A1 siRNA has been shown to dramatically reduce the overproduction of IL-1 induced by an LPS challenge in mice.

One embodiment of the present invention provides a method of treating multiple myeloma. Multiple myeloma ("MM") is a progressive and fatal disease characterized by the expansion of malignant plasma cells in the bone marrow and by the presence of osteolytic lesions. Multiple myeloma is an incurable but treatable cancer of the plasma cell. Plasma cells are an important part of the immune system, producing immunoglobulins (antibodies) that help fight infection and disease. Multiple myeloma is characterized by excessive numbers of abnormal plasma cells in the bone marrow and overproduction of intact monoclonal immunoglobulins (IgG, IgA, IgD, or IgE; "M-proteins") or Bence-Jones protein (free monoclonal light chains). Hypocalcaemia, anemia, renal damage, increased susceptibility to bacterial infection, and impaired production of normal immunoglobulin are common clinical manifestations of multiple myeloma. Multiple myeloma is often also characterized by diffuse osteoporosis, usually in the pelvis, spine, ribs, and skull.

The present invention seems to be well suited to treat multiple myeloma because of the stimulation feedback loop found in multiple myeloma. For instance, multiple myeloma produces Il-1 in low concentrations in bone marrow. The Il-1 in turn stimulates stromal cells to produce IL-6, which then goes onto stimulate growth of the multiple myeloma. The inventors have previously shown (see pending application Ser. Nos. 11/725,539 and 11/184,982) that siRNA directed against eIF-5A1 was able to inhibit expression of proinflammatory cytokines, such as Il-1; TNF-α, and Il-8). Thus, the siRNA would not only knock down expression of eIF-5A so less is available for hypusination, it would also cut off or decrease the Il-1/Il-6 feedback loop.

An siRNA targeting human eIF5A was used to suppress levels of endogenous hypusinated eIF5A in tumours, while an RNAi-resistant plasmid expressing a mutant of eIF5A (eIF5A$^{K50R}$), that is incapable of being hypusinated, was used to raise the levels of unmodified eIF5A in vivo. Intra-tumoural injection of PEI nanocomplexes containing eIF5A siRNA inhibited MM tumour growth by more than 80% (*p=0.0003) versus complexes containing a control siRNA, indicating that suppressing levels of hypusinated eIF5A has an anti-tumoural effect. PEI complexes containing an eIF5A$^{K50R}$ expression plasmid had a similar effect and inhibited tumour growth by more than 70% (=p 0.001) versus complexes containing a control plasmid. Thus, MM tumour growth can be inhibited either by suppression of the growth-promoting hypusinated eIF5A or by increasing levels of the pro-apoptotic unhypusinated form of eIF5A. Intra-tumoural delivery of complexes containing both eIF5A siRNA and RNAi-resistant eIF5A$^{K50R}$ plasmid had a synergistic effect on tumour growth and resulted in significant tumour shrinkage, inhibiting tumour growth by 94% (*p=0.0002). Intra-venous delivery of eIF5A siRNA/ eIF5A$^{K50R}$ PEI complexes also efficiently reduced tumour growth by 95% (p=0.002) indicating systemic delivery of the therapeutic is feasible.

Both local and systemic delivery of eIF5A siRNA/ eIF5A$^{K50R}$ pDNA PEI complexes resulted in a significant anti-tumoural response in multiple myeloma.

The present invention further provides a composition useful in the treatment of cancer, including multiple myeloma. In a preferred embodiment, the composition is a complex of a plasmid DNA encoding point-mutated eIF5A1 that cannot be hypusinated and eIF5A1 siRNA that selectively suppresses endogenous human eIF5A1 but has no effect on the point-mutated eIF5A1 encoded by the plasmid. eIF5A1 siRNAs and polynucleotides encoding mutant eIF5A1 are discussed above. The plasmid DNA and the siRNA are both preferably complexed to PEI (polyethylenimine) nanoparticles. They may be complexed separately and administered separately or together or they may be complexed together. The DNA and the RNA bind to positively charged amino groups on the PEI and are released when the nanoparticles are taken up into cells. It has been demonstrated that PEI-nucleic acid complexes are effectively taken up into both dividing and non-dividing cells.

The plasmid DNA preferably encodes eIF5A1(K50R) which, like eIF5A1(K50A), cannot be hypusinated and, accordingly, is strongly apoptogenic. The expression of eIF5A1(K50R) is preferably regulated by a B-cell-specific promoter.

The eIF5A1 siRNA is preferably specific to the 3'-end of endogenous human eIF5A1 and has no effect on expression of the trans eIF5A1(K50R). An exemplary preferred eIF5A1 siRNA comprises, consists essentially of or consists of the siRNA shown in FIG. 25. The rationale for including the eIF5A1 siRNA is: (1) to deplete endogenous eIF5A1, which is almost all hypusinated and hence in the pro-survival form; (2) to inhibit activation of NF-κB, and thereby reduce the production of IL-6 and the formation of intracellular adhesion molecules; and (3) to inhibit the formation of IL-1. That eIF5A1 siRNA acts synergistically with eIF5A1(K50R) to induce apoptosis in myeloma cells. Inasmuch as (2) and (3) above are pro-survival events, they are likely mediated by hypusinated eIF5A1, and hence not affected by eIF5A1 (K50R) which cannot by hypusinated. This approach results in a larger pool of unhypusinated eIF5A leading to apoptosis of cancer cells, including multiple myeloma cells, with little effect on healthy cells.

A preferred composition is referred to herein as SNS01. SNS01 is a complex containing both, an RNAi-resistant plasmid DNA encoding eIF5A$^{K50R}$ driven by a promoter that restricts expression to cells of B-cell origin (including myeloma cells) for enhanced safety, and an siRNA targeting human eIF5A with dTdT 3' overhangs for enhanced nuclease resistance and which the siRNA and the plasmid are complexed to in vivo JetPEI™.

EXAMPLES

Example 1

Transfection of HeLaS3 Cells with Wild Type and Variants of eIF-5A1

Figure 2B:
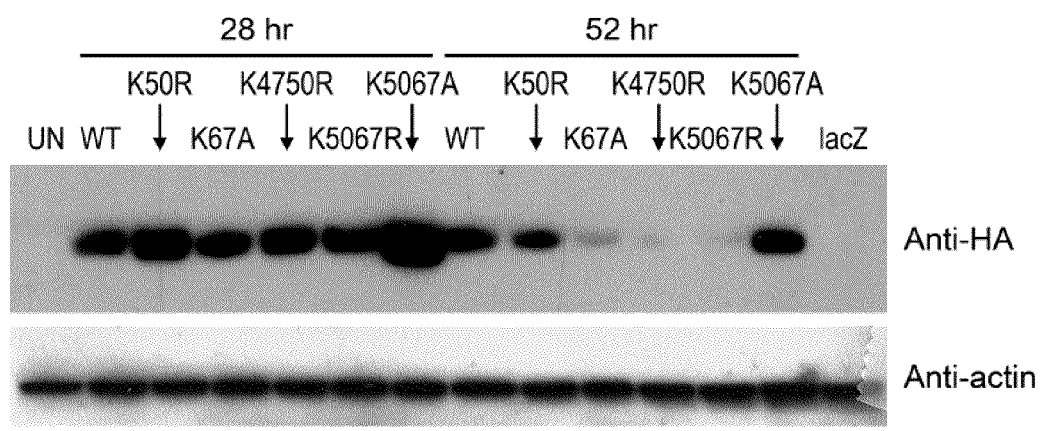

HeLa S3 cells were transfected using Lipofectamine 2000 with plasmids expressing HA-tagged eIF5A1 variants including wild-type eIF5A1 (WT), eIF5A1K50R (K50R), eIF5A1K67R (K67R), eIF5A1K67A (K67A), eIF5A1K47R/K50R (K4750R), eIF5A1K50R/K67R (K5067R), or eIF5A1K50A/K67A (K5067A). A plasmid expressing LacZ was used as a control. At 24 and 48 hours (A) or 28 and 52 hours (B) after transfection, the cell lysate was harvested and fractionated by SDS-PAGE. Expression levels of transfected eIF5A1 was detected using an antibody against HA. Result: Mutation of eIF5A1 at a lysine in the putative ubiquination site (K67R) increased the accumulation of the eIF5A1 transgene above wild-type (A). Mutation of eIF5A1 at the lysine required for hypusination (K50R) also increased accumulation of eIF5A1 transgene above wild-type eIF5A (B). A double mutant form of eIF5A1 (K50A/K67A) was expressed particularly well when compared to the unmutated wild-type eIF5A1 transgene (A+B). See FIG. 2.

Example 2

Transfection of KAS Cells with Wild Type and Variants of eIF-5A1

Figure 3:
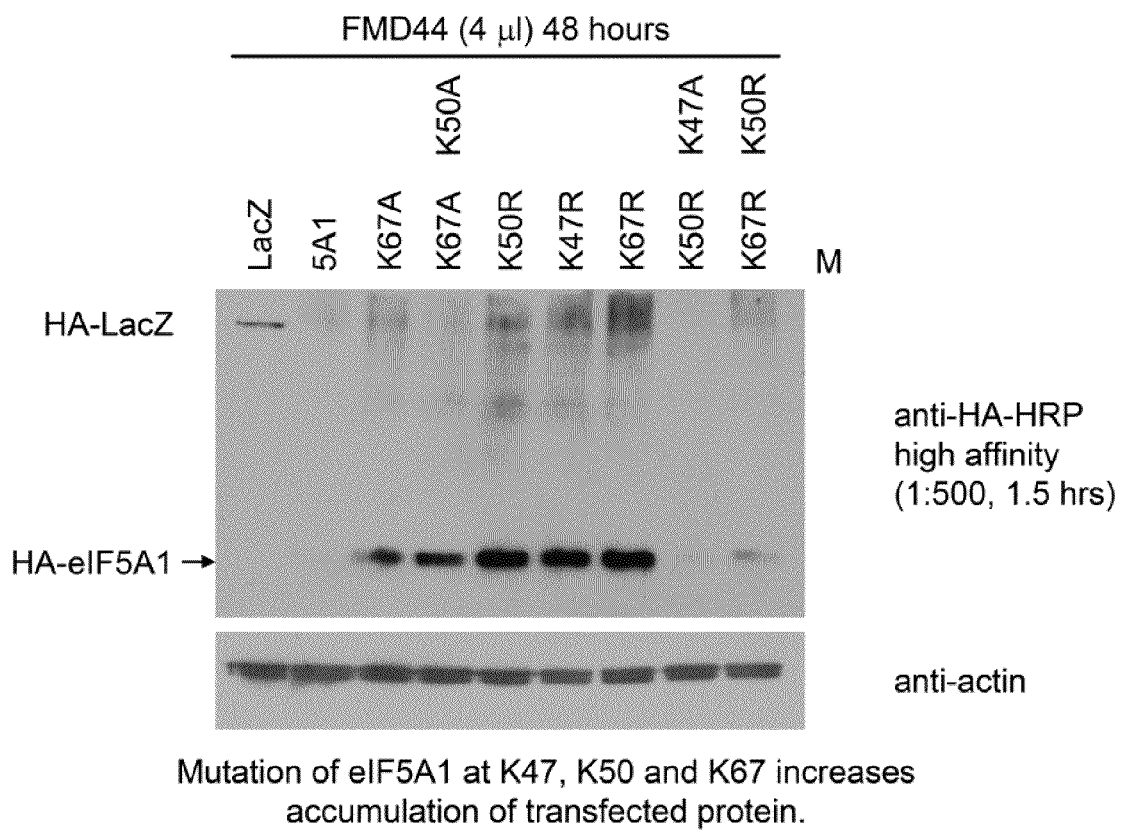
FIG. 3 shows that mutation of eIF5A1 at K47, K50 and K67 increases accumulation of transfected protein. See example 2.

KAS cells were transfected using PAMAM dendrimer (FMD44) with plasmids expressing HA-tagged eIF5A1 variants including wild-type eIF5A1 (5A1), eIF5A1K67A (K67A), eIF5A1K50A/K67A (K50A1K67A), eIF5A1K50R (K50R), eIF5A1K47R (K47R), eIF5A1K67R (K67R), eIF5A1K47R/K50R (K47R K50R), or eIF5A1K50R/K67R (K50R K67R). A plasmid expressing LacZ was used as a control. 48 hours (after transfection, the cell lysate was harvested and fractionated by SDS-PAGE. Expression levels of transfected eIF5A1 was detected using an antibody against HA. Equal loading was verified using an antibody against actin. Result: Mutation of eIF5A1 at a lysine in the putative ubiquination site (K67A or K67R) increased the accumulation of the eIF5A1 transgene above wild-type. Mutation of eIF5A1 at the lysine required for hypusination (K50R) or at an acetylation site (K47R) also increased accumulation of eIF5A1 transgene above wild-type eIF5A. A double mutant form of eIF5A1 (K50A/K67A) was also expressed at higher levels when compared to the unmutated wild-type eIF5A1 transgene. See FIG. 3.

Example 3

Transfection of KAS Cells using PAMAM Dendrimer

Figure 4:
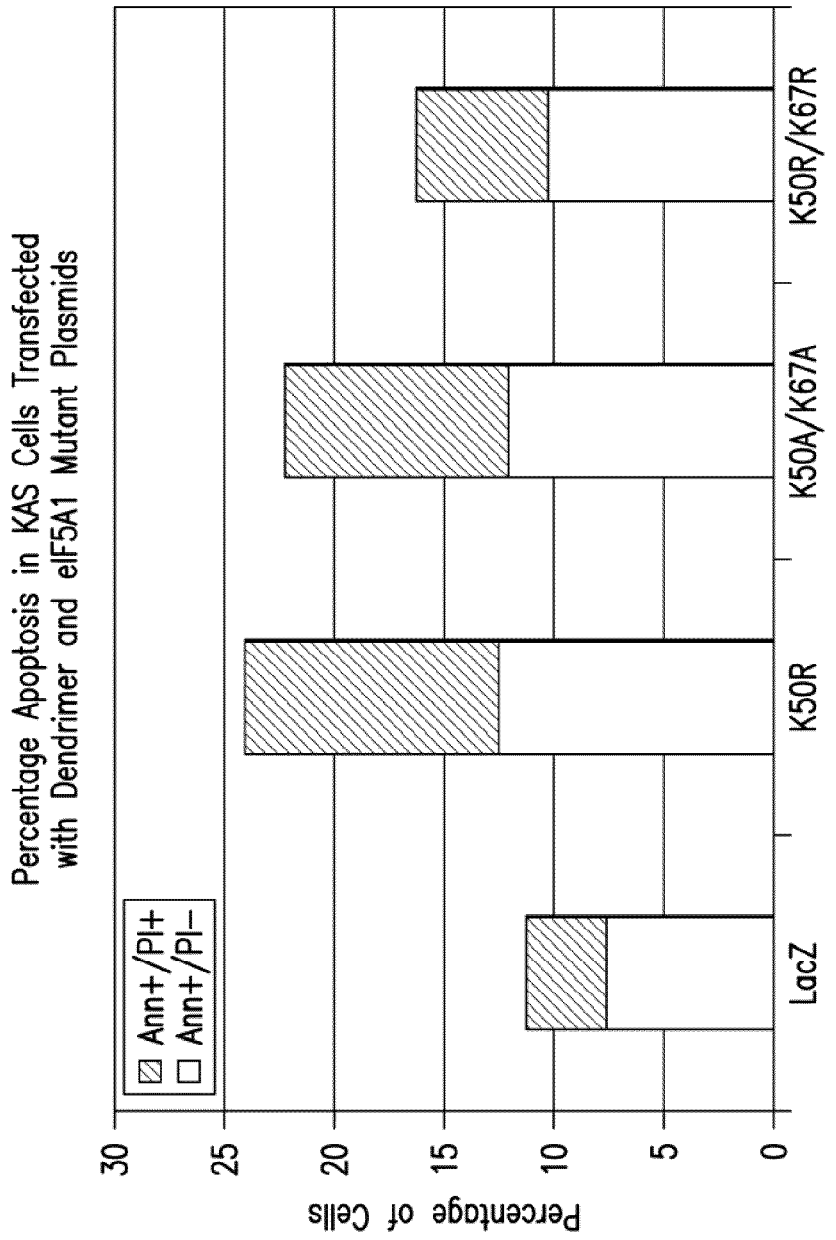
FIG. 4 shows that mutation of eIF5A1 at K50 and K67 results in induction of apoptosis when transfected into KAS cells. See example 3.

KAS cells were transfected using PAMAM dendrimer (FMD45-2) with plasmids expressing HA-tagged eIF5A1 variants including eIF5A1K50R (K50R), eIF5A1K50A/K67A (K50A/K67A), or eIF5A1K50R/K67R (K50R K67R). A plasmid expressing LacZ was used as a control. Seventy-two hours after transfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or in the putative ubiquination site (K67R), as well as the double mutant (K50A/K67A) resulted in apoptosis of KAS cells significantly above the levels of the LacZ control. See FIG. 4.

Example 4

Transfection of KAS Cells with Plasmids Expressing eIF-5A1 and eIF-5A1 Variants

Figure 5:
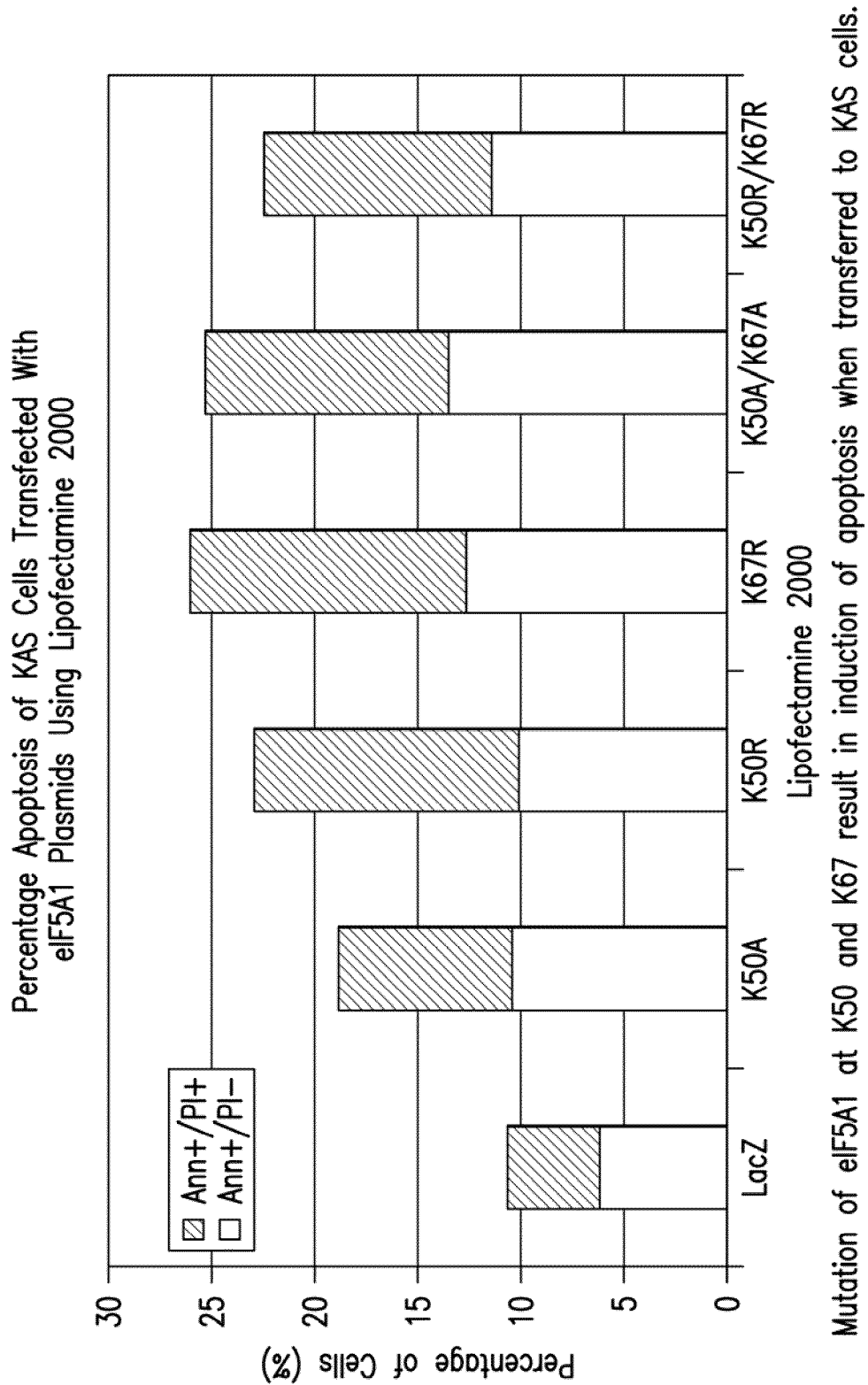
FIG. 5 shows that mutation of eIF5A1 at K50 and K67 results in induction of apoptosis when transfected into KAS cells. See example 4.

KAS cells were transfected using Lipofectamine 2000 with plasmids expressing HA-tagged eIF5A1 variants including eIF5A1K50A (K50A), eIF5A1K50R (K50R), eIF5A1K67R (K67R), eIF5A1K50A/K67A (K50A/K67A), or eIF5A1K50R/K67R (K50R K67R). A plasmid expressing LacZ was used as a control. Seventy-two hours after transfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or In the putative ubiquination site (K67R), as well as the double mutant (K50A/K67A) resulted in apoptosis of KAS cells significantly above the levels of the LacZ control. See FIG. 5.

Example 5

The use of Mutated eIF-5A1 to Treat KAS Cells Results in Apoptosis

Figure 6:
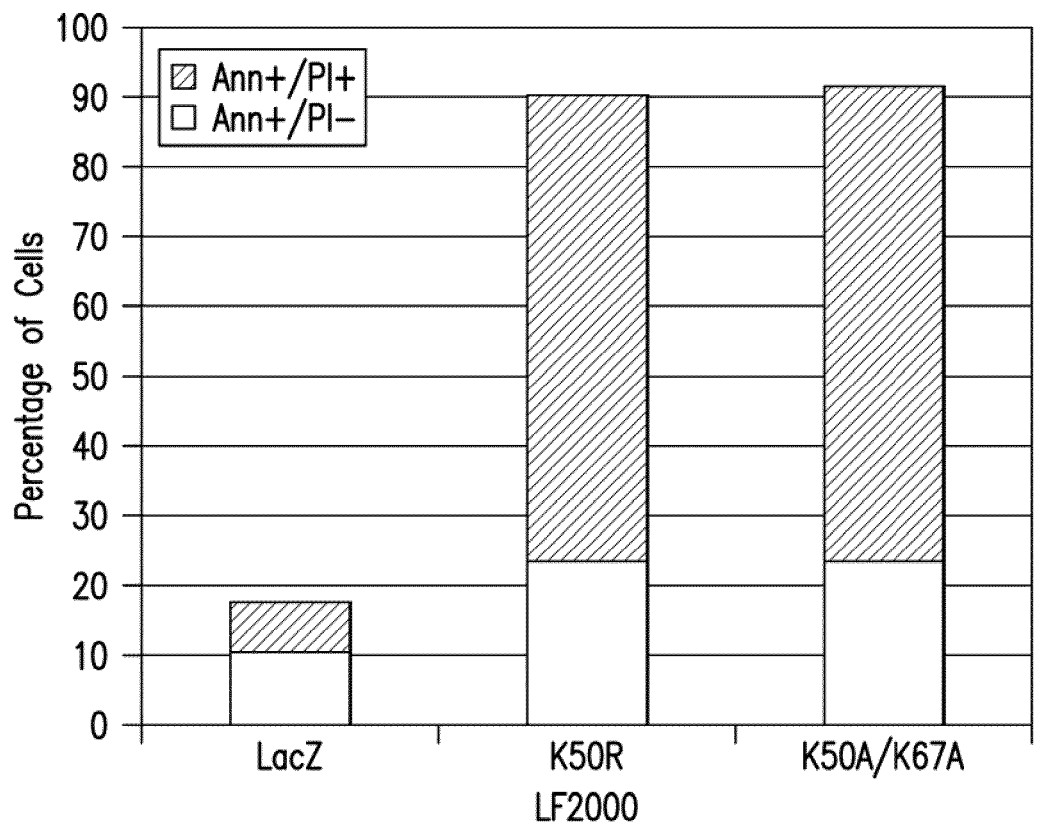
FIG. 6 shows that mutation of eIF5A1 at K50 and K67 results in induction of apoptosis when transfected into KAS cells. See example 5.
Figure 7A:
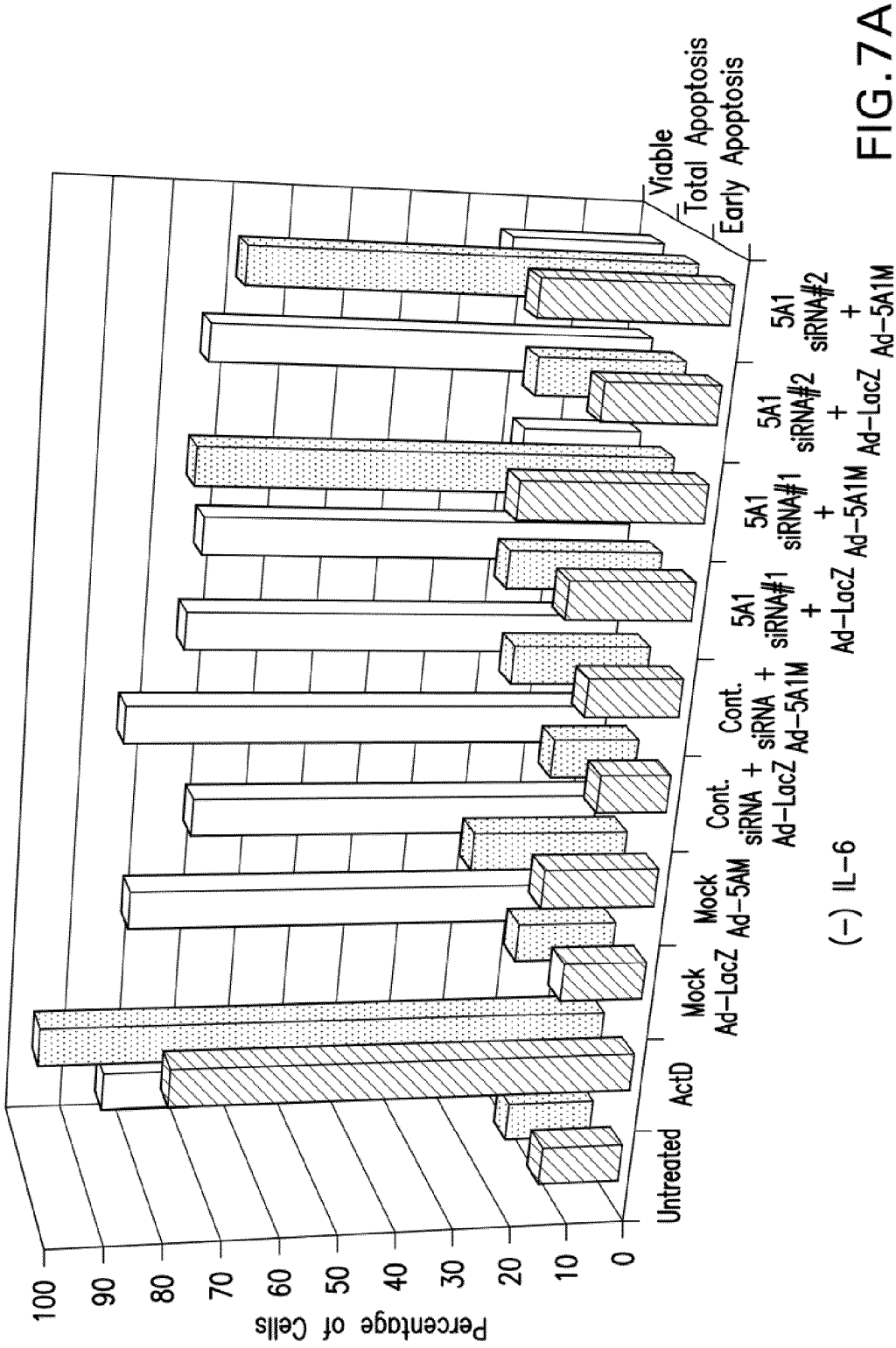
FIG. 7A shows transfection with siRNA and treating with an adenovirus that is modified to express eIF-5A1 results in apoptosis in KAS cells. See example 6A.
Figure 7B:
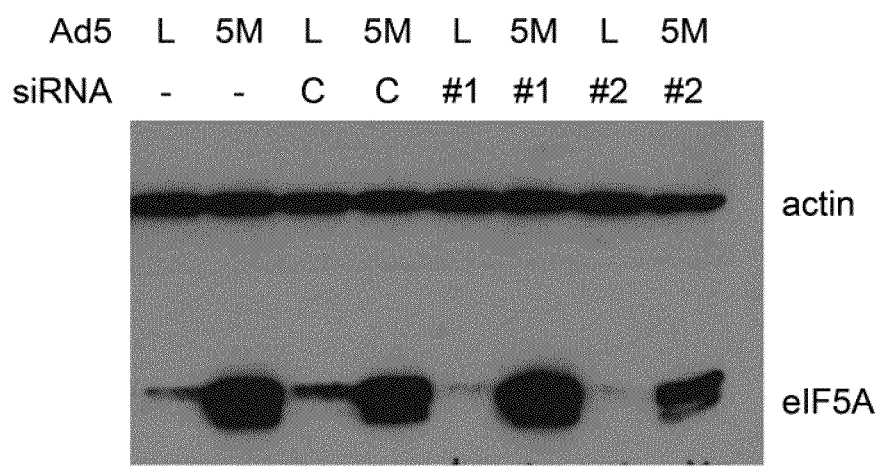
FIG. 7B shows that pre-treatment with eIF5A1 siRNA (against target #1 (SEQ ID NO: 1))(the sequence of the siRNA construct shown in FIG. 25 reduced expression of endogenous eIF5A1 but allows accumulation of RNAi-resistant eIF5A1$^{k50A}$ expressed by adenovirus. See example 6B.
Figure 7C:
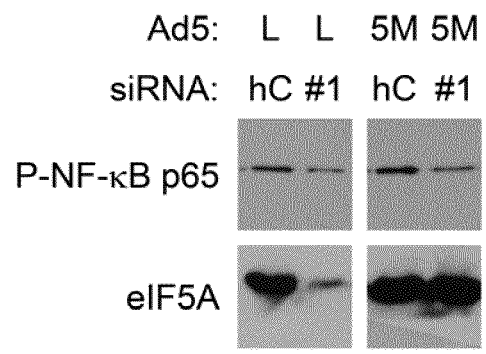
FIG. 7C shows that pre-treatment with eIF5A1 siRNA against target #1 prior to adenovirus infection reduces expression of phosphorylated NF-κB in human multiple myeloma cells. See example 6C.
Figure 7D:
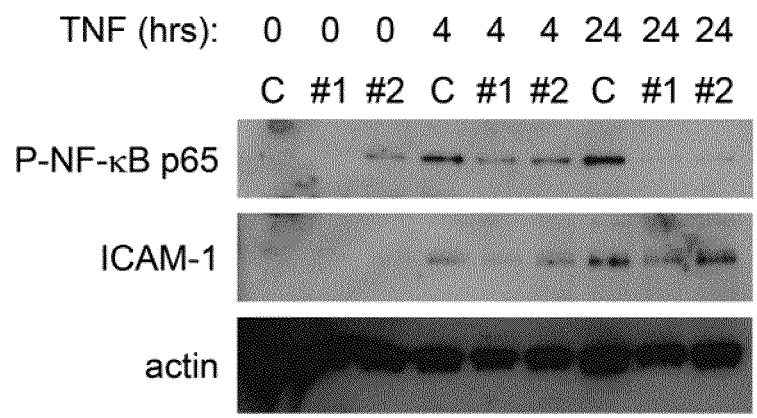
FIG. 7D shows that pre-treatment with eIF5A1 siRNA against target #1 prior to Adenovirus infection reduces expression of phosphorylated NF-kB and ICAM-1 in human multiple myeloma cells. See example 6D.
Figure 7E:
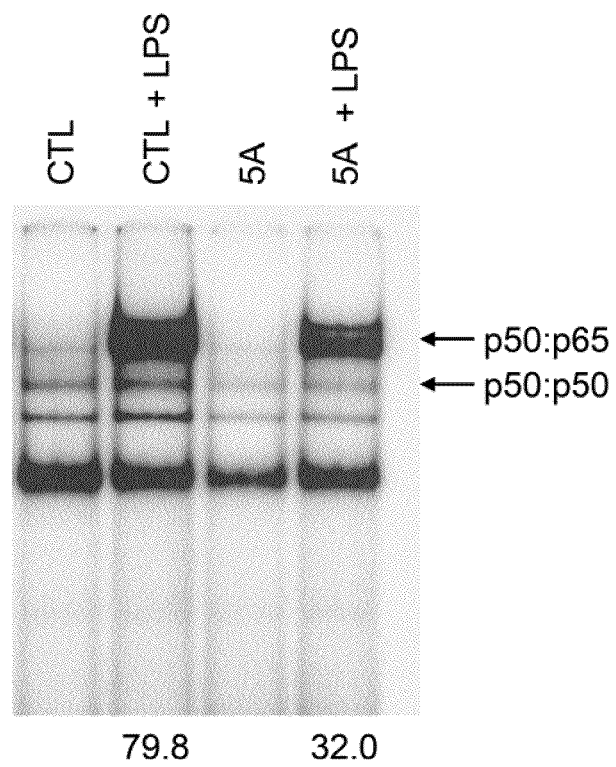
FIG. 7E shows that siRNA-mediated suppression of eIF5A in human multiple myeloma cells inhibits LPS-mediated induction of NFkB DNA-Binding Activity. The inhibition of NFkB activity by eIF5A siRNA could explain it's ability to increase apoptosis induction when combined with over-expression of eIF5A$^{K50R}$ since NF-kB regulates many pro-survival and anti-apoptosis pathways.
Figure 7F:
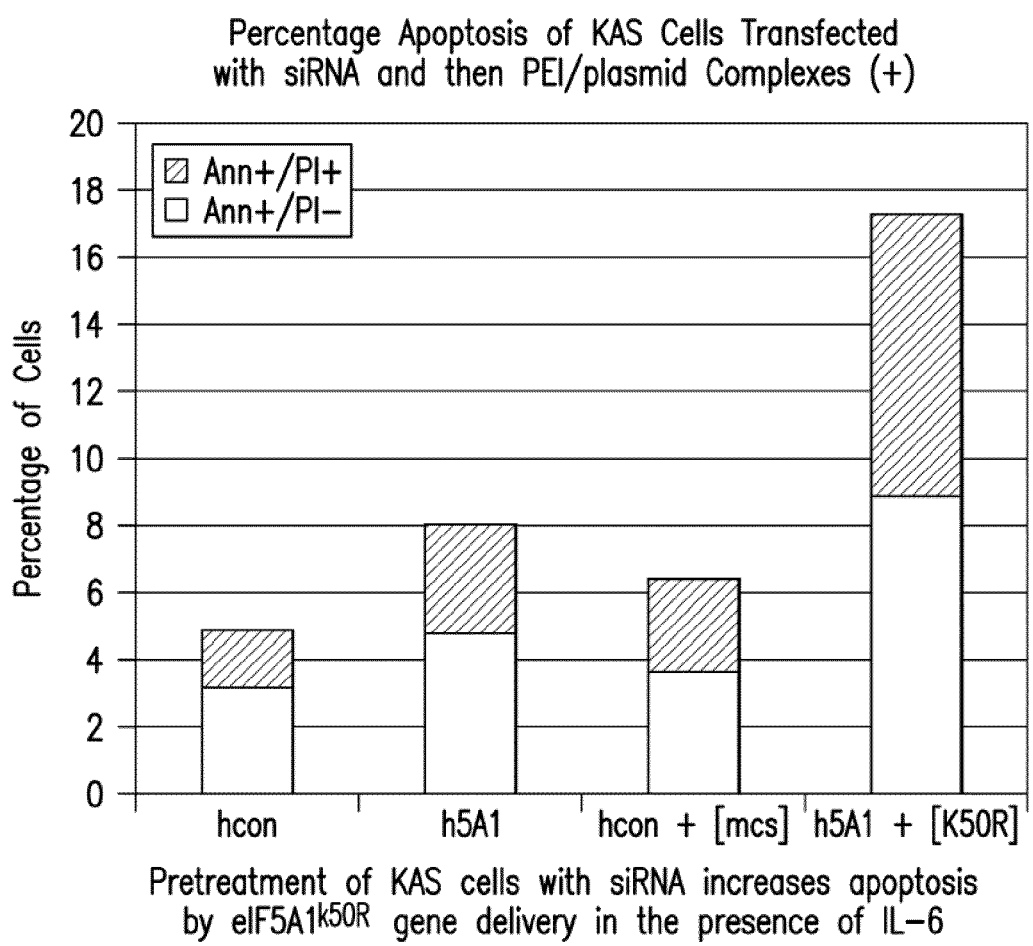
FIG. 7F shows that pretreatment of KAS cells with siRNA increases apoptosis by eIF5A1$^{k50R}$ gene delivery in the presence of IL-6. See example 6E.

KAS cells were transfected using Lipofectamine 2000 with plasmids expressing HA-tagged eIF5A1 variants eIF5A1K50R (K50R) or eIF5A1K50A/K67A (K50A/K67A. A plasmid expressing LacZ was used as a control. Seventy-two hours aftertransfection, the cells were stained with Annexin/PI and analyzed by FACS. Cells that stained positively for Annexin V and negatively for PI (propidium iodide) were considered to be in the early stages of apoptosis (Ann+/PI−) and cells that stained positively for both Annexin V and PI were considered to be in the late stages of apoptosis (Ann+/PI+). Result: Mutation of eIF5A1 at a lysine in the hypusination site (K50R) or mutation of eIF5A1 at both the hypusination site and in the putative ubiquination site (K50A/K67A) resulted in apoptosis of KAS cells significantly above the levels of the LacZ control. See FIG. 6.

Example 6A siRNA/Adenovirus-Mediated Killing of Multiple Myeloma Cells

KAS (human multiple myeloma) cells were maintained in S10 media [RPMI 1640 with 4 ng/ml IL-6, 10% fetal bovine serum (FBS), and penicillin/streptomycin (P/S)]. KAS cells were transfected with 58.7 pmoles of siRNA using Lipofectamine 2000 (Invitrogen). Mock transfected cells were treated with Lipofectamine 2000 in the absence of siRNA. Transfection was conducted in the antibiotic-free S10 media.
  a) siRNAs targeting human eIF5A1:
    eIF5A1 siRNA target #1 (the siRNA targets this region of human eIF5A1: 5'-AAGCTGGACTCCTCCTACACA-3' (SEQ ID NO: 1). The siRNA sequence is shown in FIG. 25 and is often referred to herein as h5A1.
    eIF5A1 siRNA target #2 eIF5A1 (this siRNA targets this region of human eIF5A1: 5'-AAAGGAATGACTTC-CAGCTGA-3' (SEQ ID NO: 2). (The siRNA sequence is often referred to herein ash5A1-ALT)
  b) control siRNA: The control siRNA had the following sequence: sense strand, 5 ACACAUCCUCCUCAG-GUCGdTdT-3' (SEQ ID NO: 3): and antisense strand, 3'-dT-dTUGUGUAGGAGGAGUCCAGC-5'" (SEQ ID NO: 4).
Other controls that have been used include non-targeting validated siRNAs from Dharmacon since they have been micro-array tested to limit unwanted off-targeting effects. For example, for in vitro work studying NFkB, the control used was Dharmacon's non-targeting siRNA's (sequence D-001700-01) and for in vivo work, the control used was Dharmacon's (sequence D-001810-01).

Four hours after transfection, the cells were pelleted and resuspended in 1 ml of S10 media. Seventy-two hours after the initial siRNA transfection, the transfected KAS cells were counted and seeded at 300,000 cells/well in a 24-well plate and transfected with the same siRNA a second time.

Four hours after transfection, the cells were pelleted and resuspended in 1 ml of S10 media (without IL-6) containing 3000 ifu of either Ad-LacZ (Adenovirus expressing β-galactosidase) or Ad-5A1M (Adenovirus expressing human eIF5A1$^{K50A}$).

Seventy-two hours later the cells were harvested and analyzed for apoptosis by staining with Annexin V-FITC and PI (BD Bioscience) followed by FACS analysis.
  a) early apoptosis was defined as cells that were positively stained with Annexin-FITC and negative for PI-staining (Ann+/PI−)
  b) total apoptosis was defined as the total of cells either in early apoptosis (Ann+/PI−) or late apoptosis/necrosis (Ann+/PI+)

The 5A1 siRNA targeting #1 targets the 3'UTR of human eIF5A1 and therefore will not affect expression of eIF5A1 from adenovirus. 5A1 siRNA targeting #2 targets within the open reading frame of human eIF5A1 and so it could potentially interfere with expression of eIF5A1 from the adenovirus.

Results:
Cells treated with siRNA and infected with adenovirus expressing the eIF-5A1 K50A variant undergo apoptosis in greater numbers than non-treated cells and cells treated only with siRNA. See FIG. 7.

Example 6B

Pre-Treatment with eIF5A1 siRNA against eIF5A1 Target #1 (Shown in FIG. 25), Reduced Expression of Endogenous eIF5A1 but allows Accumulation of RNAi-Resistant eIF5A1$^{K50A}$ Expressed by Adenovirus KAS cells were transfected using Lipofectamine 2000 with either a control siRNA (C) or one of two siRNAs targeting eIF5A1 (#1 and #2). The eIF5A1 siRNA #1 targets the 3'UTR of eIF5A1 and therefore does not interfere with expression of eIF5A1 from adenovirus since it contains only the open reading frame of eIF5A1. The sequence of the siRNA is shown in FIG. 25. The eIF5A1 #2 siRNA targets the open reading frame of eIF5A1 and will therefore affect expression of both endogenous and exogenously-expressed eIF5A1. Seventy-two hours after the initial transfection hours the cells were transfected with the same siRNA a second time. Four hours later the transfection complexes were removed from the cells and replaced with growth media (−) IL6 containing either Ad-LacZ (L) or Ad-eIF5A1$^{K50A}$ (5M). Seventy-two hours later the cell lysate was harvested and analyzed by Western blot using antibodies against eIF5A and actin. See FIG. 7B. Accumulation of virally expressed eIF5A1 can be observed (lane 1 vs lane 2) and reduction of eIF5A expression by eIF5A1 siRNAs targeting #1 and #2 can be clearly seen (lanes 5 and 7 vs lane 3). As expected, the eIF5A1 siRNA #1 does not affect accumulation of the virally expressed eIF5A1$^{K50A}$ (lane 6 vs lane 4) while the eIF5A1 siRNA #2 only moderately affects expression of the virally-expressed transgene (lane 8 vs lane 4).

Example 6C

Pre-Treatment with eIF5A 1 siRNA against Target #1 Prior to Adenovirus Infection Reduces Expression of Phosphorylated NF-κB in Human Multiple Myeloma Cells KAS cells were transfected using Lipofectamine 2000 with either a control siRNA (hC) or an siRNA targeting eIF5A1 (#1). The eIF5A1 siRNA #1 targets the 3'UTR of eIF5A1 and will therefore not interfere with expression of eIF5A1 from adenovirus since it contains only the open reading frame of eIF5A1. Seventy-two hours after the initial transfection hours the cells were transfected with the same siRNA a second time. Four hours later the transfection complexes were removed from the cells and replaced with growth media (+) IL6 containing either Ad-LacZ (L) or Ad-eIF5A1$^{K50A}$ (5M). Twenty-four hours later the cell lysate was harvested and analyzed by Western blot using antibodies against phospho-NF-kB p65 (Ser 536) and eIF5A. As expected, the eIF5A1 siRNA #1 does not affect accumulation of the virally expressed eIF5A1$^{K50A}$. Phosphorylation of NF-kB p65 at serine 536 regulates activation, nuclear localization, protein-protein interactions, and transcriptional activity. See FIG. 7C.

Example 6D

Pre-Treatment with eIF5A1 siRNA #1 Prior to Adenovirus Infection Reduces Expression of Phosphorylated NF-kB and ICAM-1 in Human Multiple Myeloma Cells KAS cells were transfected using Lipofectamine 2000 with either a control siRNA (C) or one of two siRNAs targeting eIF5A1 (#1 and #2). Seventy-two hours after the initial transfection hours the cells were transfected with the same siRNA a second time. Four hours later the transfection complexes were removed from the cells and replaced with growth media (+) IL6. Twenty-four hours after the second transfection, the cells were stimulated with 40 ng/ml TNF-α and cell lysate was harvested at 0, 4, or 24 hours and analyzed by Western blot using antibodies against phospho-NF-kB p65 (Ser 536), ICAM-1 and actin. A reduction in TNF-α induced NF-kB p65 phosphorylation (ser 536) and ICAM-1 expression was observed following transfection with both eIF5A1-specific siRNAs. Phosphorylation of NF-kB p65 at serine 536 regulates activation, nuclear localization, protein-protein interactions, and transcriptional activity. ICAM-1 is an inter-cellular adhesion surface glycoprotein that is believed to be involved in the pathogenesis of multiple myeloma. See FIG. 7D.

Example 6E

Pretreatment of KAS Cells with siRNA Increases Apoptosis by eIF5A1$^{k50R}$ Gene Delivery in the Presence of IL-6

KAS cells were transfected with either control siRNA (hcon) or human eIF5A1 siRNA (h5A1) using Lipofectamine 2000. Seventy-two hours later the cells were re-transfected with siRNA. PEI complexes of empty vector (mcs) or eIF5A1$^{k50R}$ (K50R) plasmids were added to the cells four hours later following removal of siRNA transfection medium. The growth medium used throughout the study contained IL-6. Apoptosis was measured seventy-two hours later by staining the cells with Annexin/PI and FACS analysis. See FIG. 7F.

Example 7

Figure 8:
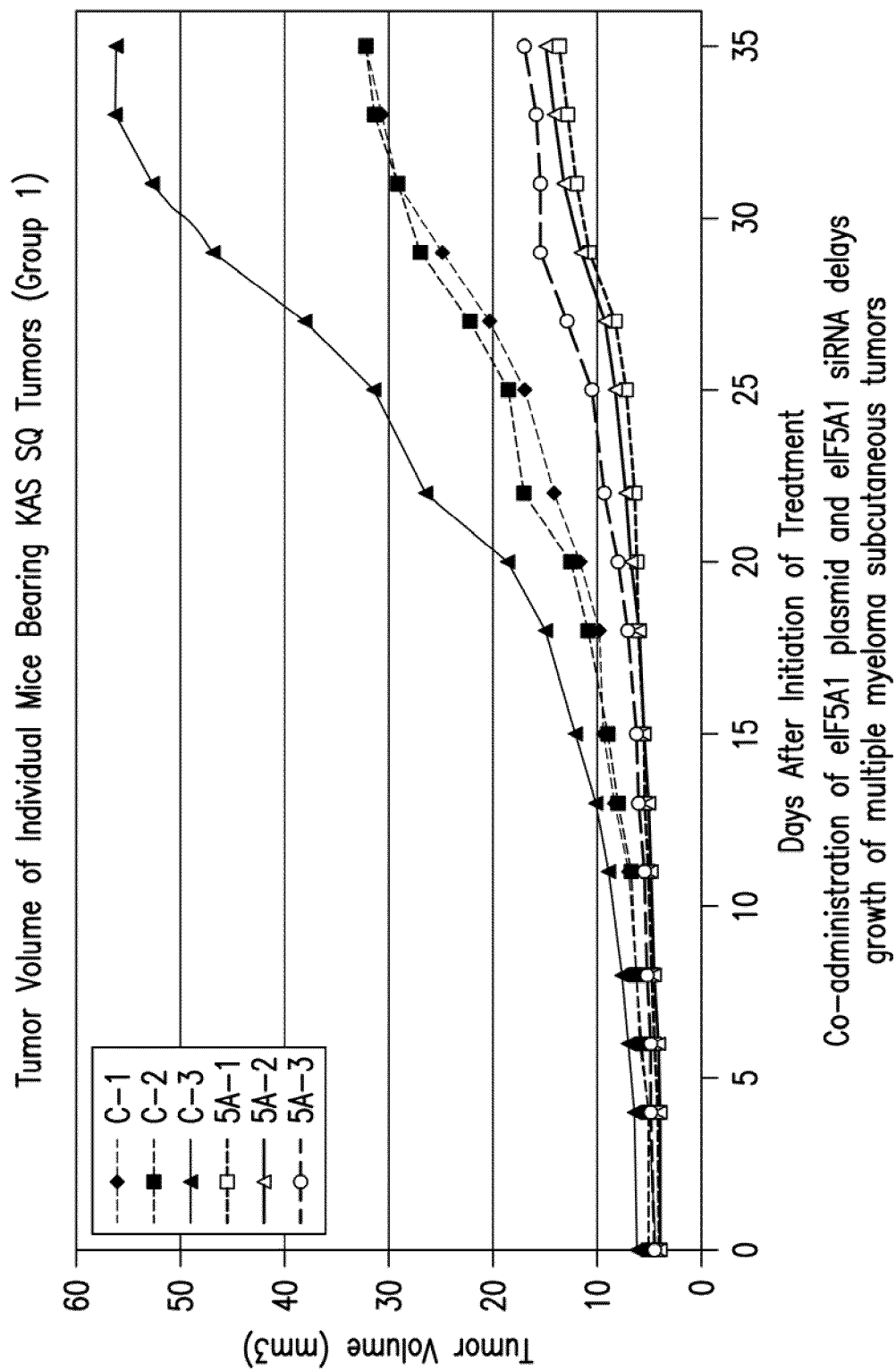
FIG. 8 shows that co-administration of eIF5A1 plasmid and eIF5A1 siRNA delays growth of multiple myeloma subcutaneous tumours. The data shown is the tumor volume for all the mice in each group. See example 7.
Figure 9:
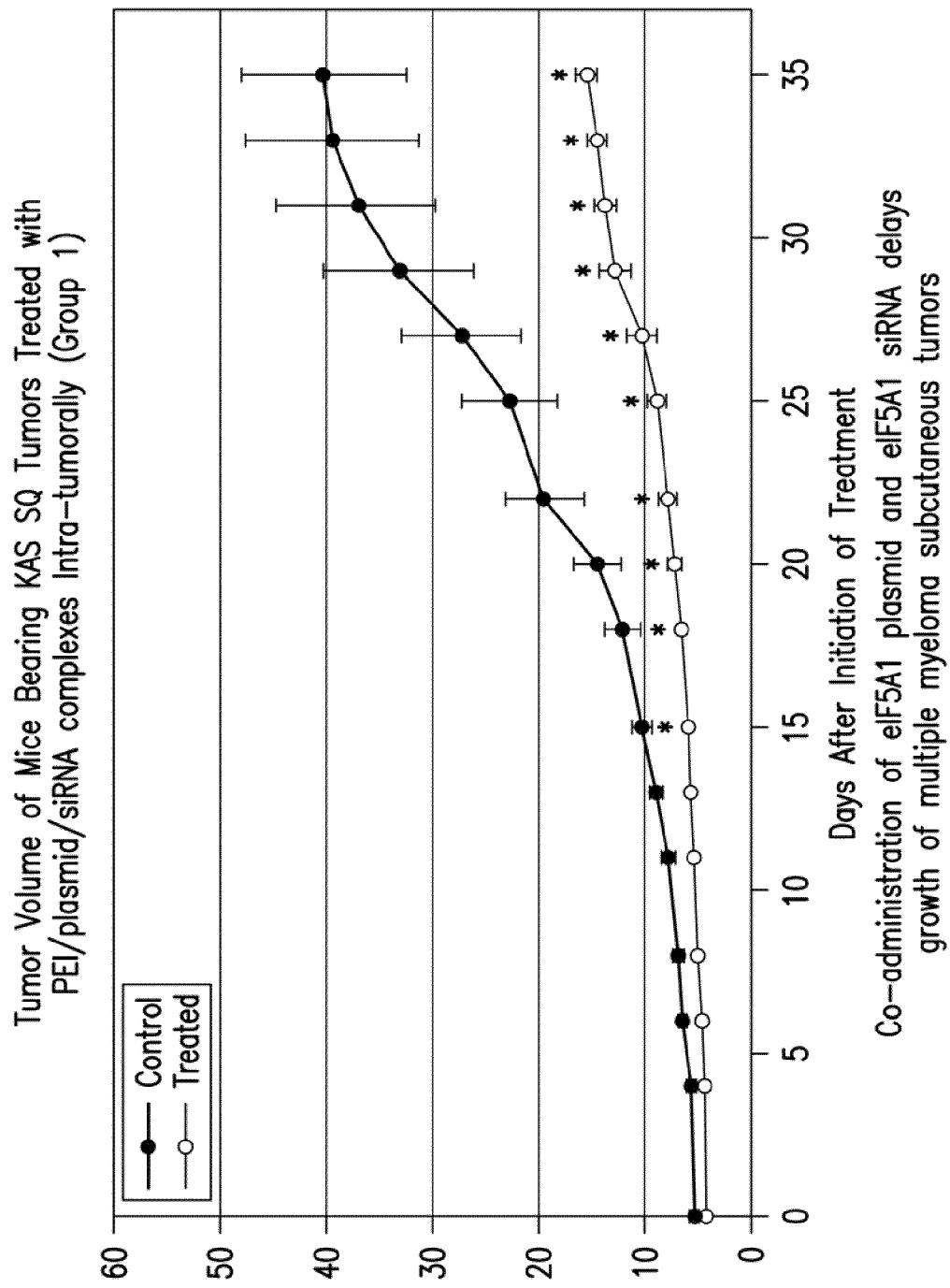
FIG. 9 shows that co-administration of eIF5A1 plasmid and eIF5A1 siRNA delays growth of multiple myeloma subcutaneous tumours. The data shown is the average tumor volume per group+/−standard error. See example 7.
Figure 10:
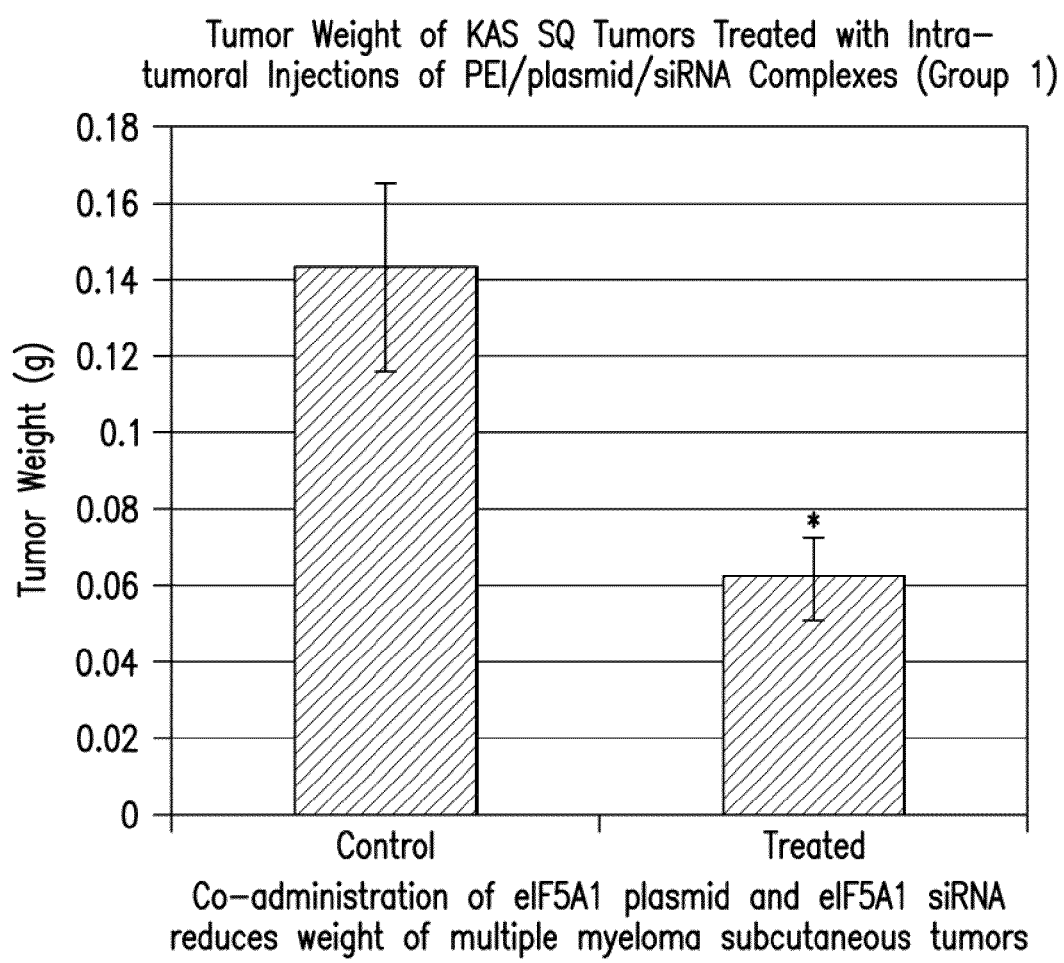
FIG. 10 shows that co-administration of eIF5A1 plasmid and eIF5A1 siRNA reduces weight of multiple myeloma subcutaneous tumours. See example 7.

Co-Administration of eIF-5A1 Plasmid and eIF-5A1 siRNA Delays Growth of Multiple Myeloma Subcutaneous Tumors (FIGS. 8-10)

SCID mice were injected subcutaneously with KAS cells. Treatment was initiated when palpable tumours were observed. Six 3-5 week old SCID/CB17 mice were injected with 10 million KAS-6/1 myeloma cells in 200 μL PBS in their right flank and treatment was initiated when the tumours reached a minimum size of 4 mm³.

Control mice were injected intra-tumourally 2 times per week with PEI complexes containing pCpG-mcs (empty vector) and control siRNA (control group was made up of 3 mice: C-1, C-2, and C-3). Treated mice were injected intra-tumourally 2 times per week with PEI complexes containing the RNAi-resistant plasmid pCpG-eIF5A1k50R and eIF5A1 siRNA (treated group was made up of 3 mice: 5A-1, 5A-2, and 5A-3). Injections were given at multiple sites within the tumor to prevent reflux and a slow rate of injection was used to increase uptake. The data in FIG. 8 shows the tumor volume for all the mice in the group. The data shown in FIG. 9 is the average tumor volume per group+/−standard error. Asterix denote statistical significance (*=p<0.025; n=3).

FIG. 10 shows that co-administration of eIF-5A1 plasmid and eIF-5A1 siRNA reduces the weight of multiple myeloma subcutaneous tumors. The data shown is the average tumor weight per group+/−standard error. Asterix denote statistical significance (*=p<0.05;n=3).

JET-PEI (PolyPlus) at 2×0.1 ml was used for the in vivo tests. The N/P ratio was 8. The PEI/DNA/siRNA complexes were formed in a total volume of 0.1 ml in 5% glucose. The protocol for forming complexes was as follows.

1. Bring components to room temperature. Keep sterile.
2. Dilute 20 μg of plasmid DNA (~10 μl at 2 mg/ml) and 10 μg siRNA (10 μl at 1 mg/ml) into a total volume of 25 μl. Use sterile water to make up difference.
3. Adjust the volume of DNA solution to 50 μl 5% glucose by adding 25 μl of 10% glucose. Vortex gently and centrifuge briefly.
4. Dilute 4.8 μl of invivo JETPEI into a total volume of 25 μl of 10% glucose. Adjust volume to 50 μl with sterile water to end up with a final concentration of 5% glucose. Vortex gently and centrifuge briefly.
5. Immediately add 50 μl of diluted PEI to the 50 μl of diluted DNA (do not reverse the order). Vortex briefly and immediately spin down.
6. Incubate for 15 minutes prior to injection. Complexes are stable for 6 hours.

CpG-free Cloning Vectors and pCpG Plasmids were obtained from InvivoGen. These plamids are completely devoid of CpG dinucleotides, named pCpG. These plasmids yield high levels of transgene expression both in vitro and in vivo, and in contrast to CMV-based plasmids allow sustained expression in vivo. pCpG plasmids contain elements that either naturally lack CpG dinucleotides, were modified to remove all CpGs, or entirely synthesized such as genes encoding selectable markers or reporters. Synthesis of these new alleles was made possible by the fact that among the sixteen dinucleotides that form the genetic code, CG is the only dinucleotide that is non-essential and can be replaced. Eight codons contain a CG encoding for five different amino acids. All eight codons can be substituted by at least a choice of two codons that code for the same amino acid to create new alleles that code for proteins having amino acid sequences that remain identical to the wild type and thus are as active as their wild-type counterparts. These new alleles are available individually in a plasmid named pMOD from which they can be easily excised.

pCpG plamids allow long lasting expression in vivo, and represent valuable tools to study the effects of CpGs on gene expression in vivo and in vitro, using cell lines expressing TLR9, as well as their effects on the innate and acquired immune systems.

The empty vector, pCpG-mcs (Invivogen) is a vector with no expressed gene product, only a multiple cloning site, and was used as the control vector. An HA-tagged eIF5A1$^{k50R}$ cDNA was subcloned into the NcoI and NheI sites of a pCpG-LacZ vector (Invivogen), from which the LacZ gene had been removed, to give rise to the treatment vector pCpG-eIF5A1 (K50R). The DNA was prepared using Endo-Free Qiagen kit. Endotoxin levels measured and are <0.03 EU/ug; DNA should be at 2 mg/ml in water.

The control siRNA used in the experiments was a microarray validated non-targeting control siRNA from Dharmacon (D-001810-01). The siRNA was obtained with a modification (siSTABLE) to prevent degradation in serum.

The eIF5A1 siRNA used in the experiments was designed against the 3'UTR of human eIF5A1. There is no similarity between the eIF5A1 siRNA and mouse eIF5A1 and the siRNA should therefore only suppress human (but not mouse) eIF5A1. The siRNA also has no similarity to eIF5A2 (either human or mouse). The siRNA was obtained with a modification (siSTABLE) to prevent degradation in serum. The eIF5A1 siRNA has the following target sequence:

```
                                           (SEQ ID NO: 5)
     5' GCU GGA CUC CUC CUA CAC A (UU) 3
```

The siSTABLE siRNA was dissolved at 1 mg/ml in water (stored in aliquots at −20 C).

Tumour dimensions of length (l) and width (w) were measured 2-3 times per week using digital calipers. Tumour volume was calculated according to the following equation:
l=length; smallest dimension
w=width; largest dimension tumour volume (mm$^3$)=$l^2$*w*0.5

Statistical Analyses

Student's t-test was used for statistical analysis. Significance was deemed to be a confidence level above 95% (p<0.05).

Example 8

Figure 11:
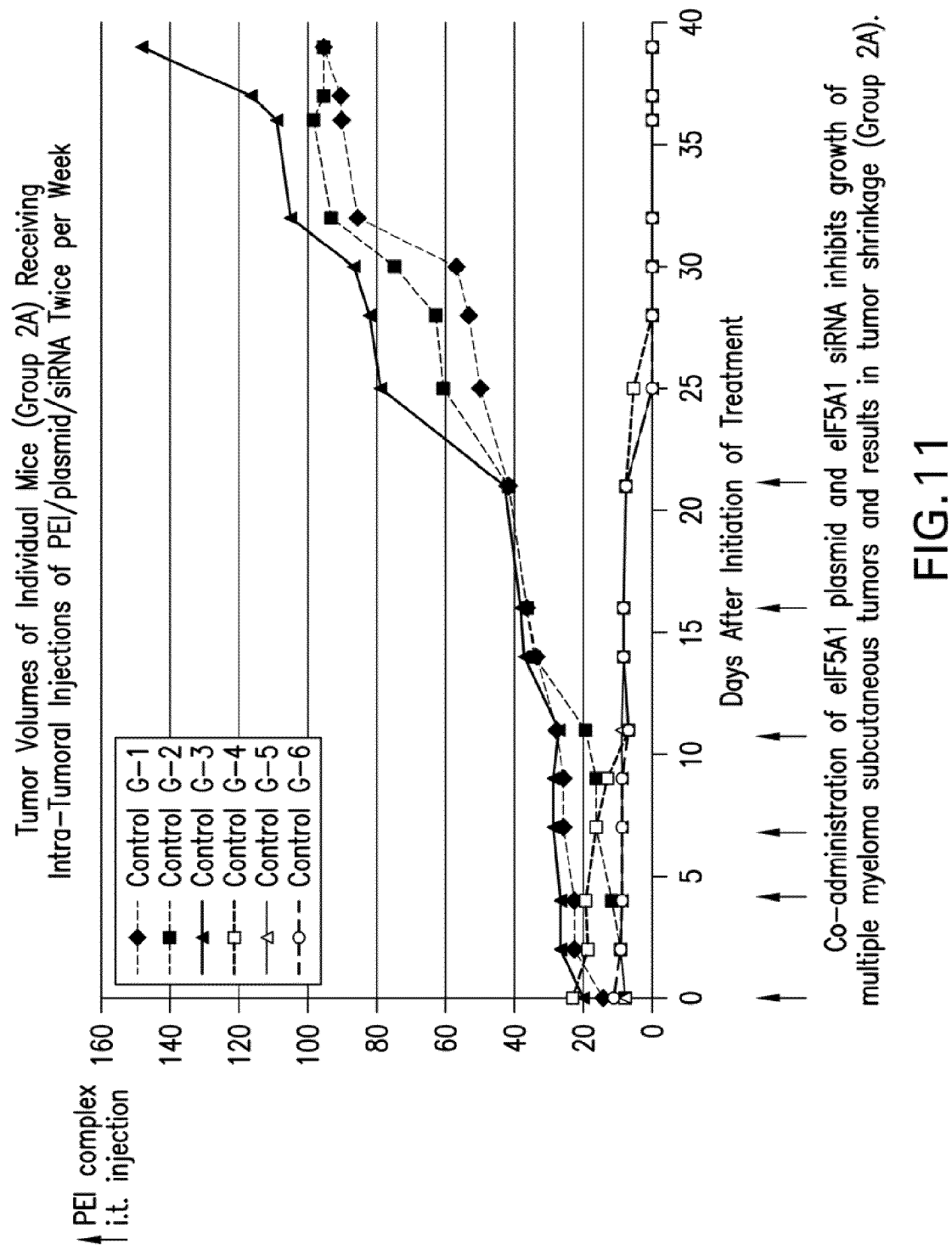
FIG. 11 shows that co-administration of eIF5A1 plasmid and eIF5A1 siRNA delays growth of multiple myeloma subcutaneous tumours and results in tumour shrinkage. See Example 8.

Co-Administration of eIF5A1 Plasmid and eIF5A1 siRNA Delays Growth of Multiple Myeloma Subcutaneous tumors and Results in Tumor Shrinkage In another study, again SCID mice were injected subcutaneously with KAS cells. Treatment was initiated when palpable tumours were observed. Control mice were injected intra-tumourally 2 times per week with PEI complexes containing pCpG-mcs (empty vector) and control siRNA (control group G-1, G-2 and G-3). Treated mice were injected intra-tumourally 2 times per week with PEI complexes containing the RNAi-resistant plasmid pCpG-eIF5A1k50R (20 µg of plasmid DNA) and eIF5A1 siRNA (10 µg of siRNA)(treated group G-4, G-5 and G-6). The data shown in FIG. 11 is the average tumour volume per group+/−standard error. Asterix denote statistical significance (*=p<0.025; n=3). Six injections over a period of 21 days were given (red arrows).

Example 9

Administration of eIF5A1 siRNA Intra-Venously (i.v.) and PEI/eIF5A1K50R Plasmid Complexes Intra-Tumourally (i.t.) Results in Tumour Shrinkage of Multiple Myeloma Subcutaneous Tumours (Group 2B)

Figure 12:
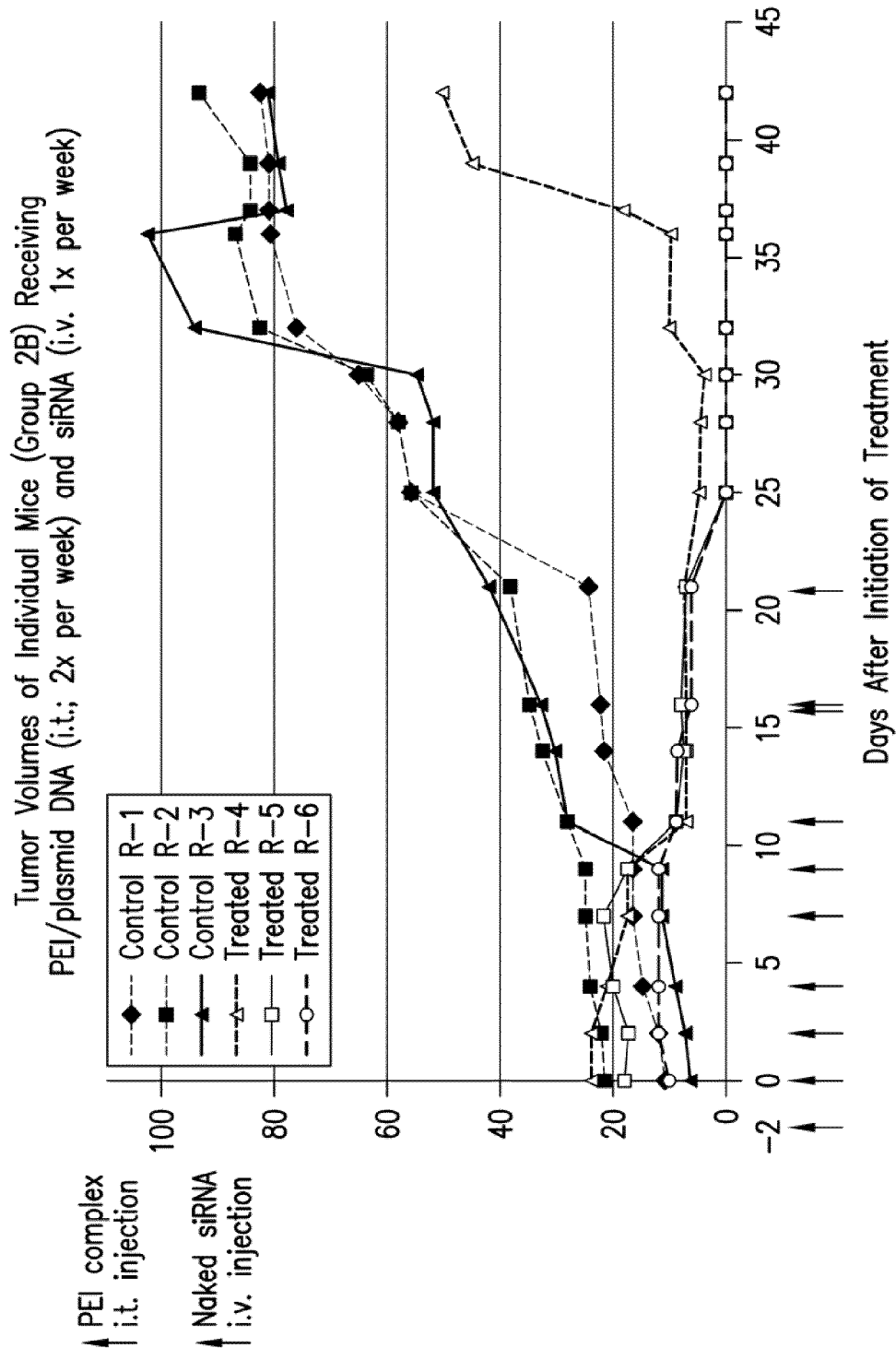
FIG. 12 shows that administration of eIF5A1 siRNA intravenously (i.v.) and PEI/eIF5A1K50R plasmid complexes intra-tumourally (i.t.) results in tumour shrinkage of multiple myeloma subcutaneous tumours. See example 9.

SCID mice were injected subcutaneously with KAS cells. When palpable tumours were observed treatment was initiated with an initial tail injection of 50 micrograms of either control siRNA (control group) or human eIF5A1 siRNA (treated group). Control Mice were subsequently treated by intra-tumoural injections 2 times per week with PEI complexes containing pCpG-mcs (empty vector; control group; G-1, G-2, and G-3). Treated mice were subsequently treated by intra-tumoural injections 2 times per week with PEI complexes containing the RNAi-resistant plasmid pCpG-eIF5A1k50R (20 µg plasmid DNA)(treated group; G-4, G-5, and G-6). Control mice continued to receive control siRNA (control group R-1, R-2, and R-3) by i.v. injection once per week. Treated mice continued to receive human eIF5A1 siRNA (20 µg)(treated group R-4, R-5, and R-6) by i.v. injection once per week. The data shown in FIG. 12 is the tumor volume for all the mice in each group. Six intramural injections of PEI/DNA (red arrows) and four i.v. injections of siRNA (blue arrows) were given over a period of 21 days.

FIG. 13 provides an overlay of the results from Example 8 and 9. SCID mice were injected subcutaneously with KAS cells. The data shown in FIG. 13 is the average tumor volume for the mice in each group+/−standard error. Asterix denote statistical significance between treated and control groups (=p<0.01; *=p<0.001; n=3).

Protocol for forming PEI complexes:
1. Bring components to room temperature. Keep sterile.
2. Dilute plasmid DNA or plasmid DNA+siRNA into a total volume of 25 µl. Use sterile water to adjust the volume.
   a) For plasmid DNA only complexes:
      Dilute 20 µg of plasmid DNA (10 µl at 2 mg/ml) into a total volume of 25 µl. Use sterile water to make up difference.
   b) For plasmid DNA+siRNA complexes:
      Dilute 20 µg of plasmid DNA (~10 µl at 2 mg/ml) and 10 µg of siRNA (10 µl at 1 mg/ml) into a total volume of 25 µl. Use sterile water to make up difference.
3. Adjust the volume of DNA solution to 50 µl 5% glucose by adding 25 µl of 10% glucose (provided with PEI kit). Vortex gently and centrifuge briefly.
4. Dilute in vivo JETPEI into a total volume of 25 µl of 10% glucose.
   a) For plasmid DNA only complexes:
      Dilute 3.2 µl of in vivo JETPEI into a total volume of 25 µl of 10% glucose. Adjust volume to 50 µl with sterile water to end up with a final concentration of 5% glucose. Vortex gently and centrifuge briefly.
   b) For plasmid DNA+siRNA complexes:
      Dilute 4.8 µl of in vivo JETPEI into a total volume of 25 µl of 10% glucose. Adjust volume to 50 µl with sterile water to end up with a final concentration of 5% glucose. Vortex gently and centrifuge briefly.
5. Immediately add 50 µl of diluted PEI to the 50 µl of diluted DNA (do not reverse the order!). Vortex briefly and immediately spin down.
6. Incubate for 15 minutes prior to injection. Complexes are stable for 6 hours.

Regarding the tail-vein injection of siRNA, the initial siRNA injection was 50 micrograms. siRNA was diluted to 0.4 mg/ml in PBS. 125 µl per mouse (50 µg) was injected into the tail vein. Subsequent injections of serum-stabilised siRNA were given two times per week at 20 µg per mouse. siRNA was diluted to 0.4 mg/ml in PBS. 50 µl per mouse (20 µg) was injected into the tail vein.

Figure 13B:
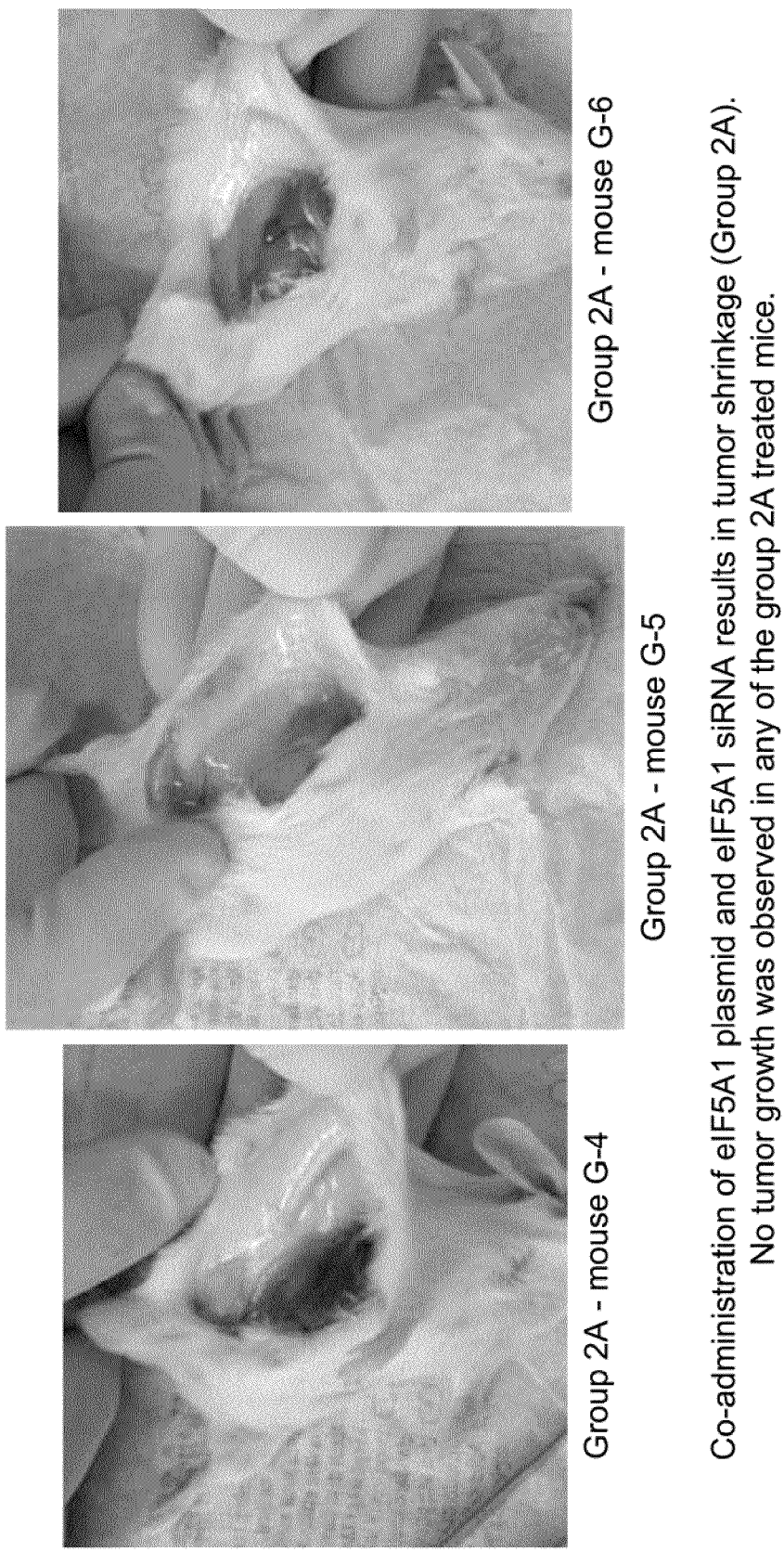
FIG. 13B shows that co-administration of eIF5A1 plasmid and eIF5A1 siRNA results in tumour shrinkage.

FIG. 13B shows that co-administration of eIF5A1 plasmid and eIF5A1 siRNA results in tumour shrinkage. SCID mice were injected subcutaneously with KAS cells. Treatment was initiated when palpable tumours were observed. Mice were injected intra-tumourally 2 times per week with PEI complexes containing the RNAi-resistant plasmid pCpG-eIF5A1k50R and eIF5A1 siRNA (treated group; G-4, G-5, and G-6). Six injections over a period of 21 days were given. Forty-two days after the initiation of treatment the mice were sacrificed and the skin under the tumour site was opened and examined for evidence of tumour growth. No tumour growth was observed in any of the group 2A treated mice.

Figure 13C:
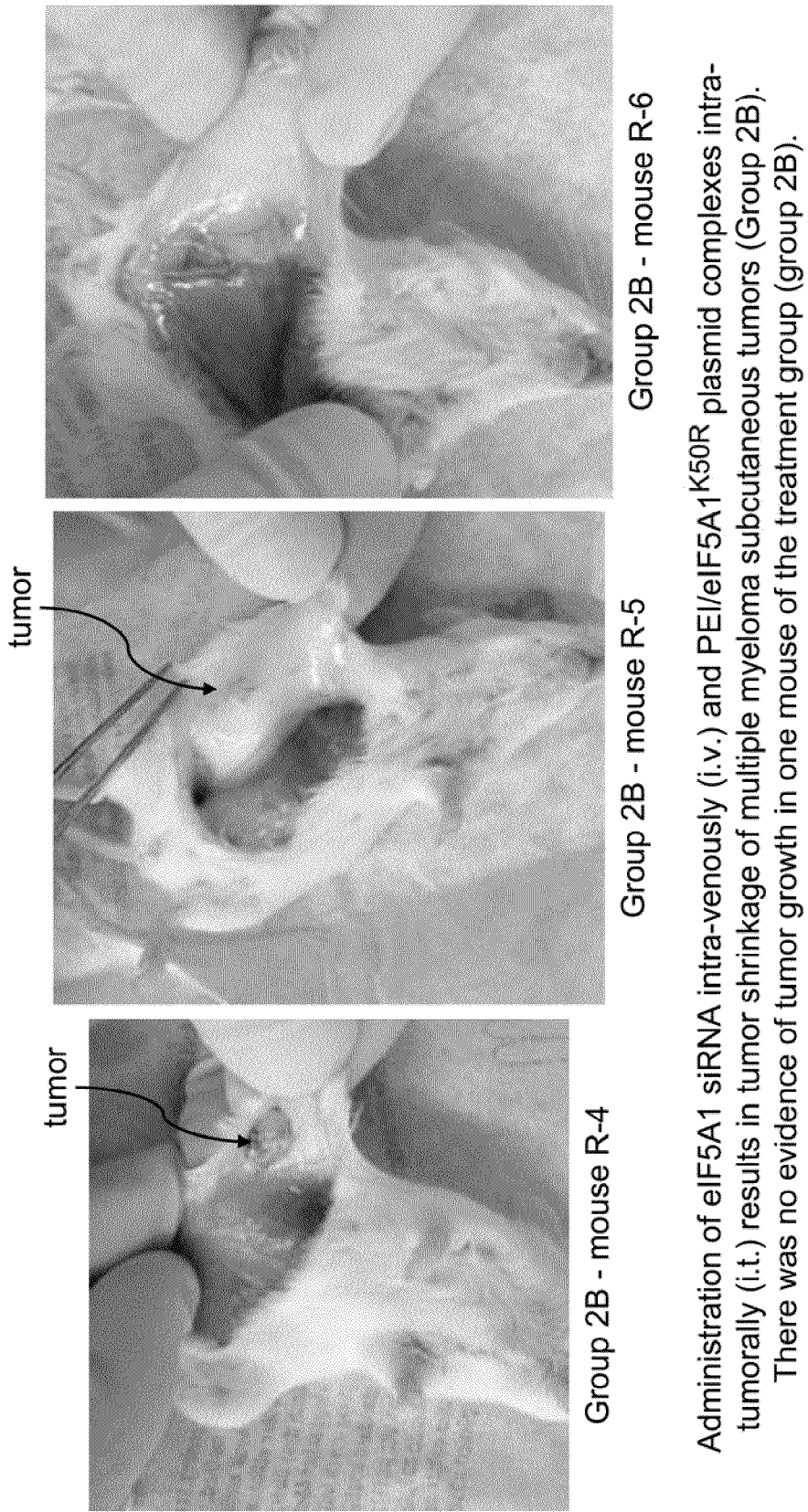
FIG. 13C shows that administration of eIF5A1 siRNA intra-venously (i.v.) and PEI/eIF5A1$^{K50R}$ plasmid complexes intra-tumourally (i.t.) results in tumour shrinkage of multiple myeloma subcutaneous tumours.

FIG. 13C shows that administration of eIF5A1 siRNA intra-venously (i.v.) and PEI/eIF5A1K50R plasmid complexes intra-tumourally (i.t.) results in tumour shrinkage of multiple myeloma subcutaneous tumours. SCID mice were injected subcutaneously with KAS cells. When palpable tumours were observed treatment was initiated with an initial injection of 50 micrograms of human eIF5A1 siRNA (treated group). Mice were subsequently treated by intra-tumoural injections 2 times per week with PEI complexes containing the RNAi-resistant plasmid pCpG-eIF5A1k50R (treated group; R-4, R-5, and R-6). Mice continued to receive human eIF5A1 siRNA by i.v. injection once per week. Treatment ended 21 days after initiation of treatment. Forty-two days after the initiation of treatment the mice were sacrificed and the skin under the tumour site was opened and examined for evidence of tumour growth. There was no evidence of tumour growth in one mouse of the treatment group (group 2B).

Example 10

Figure 14:
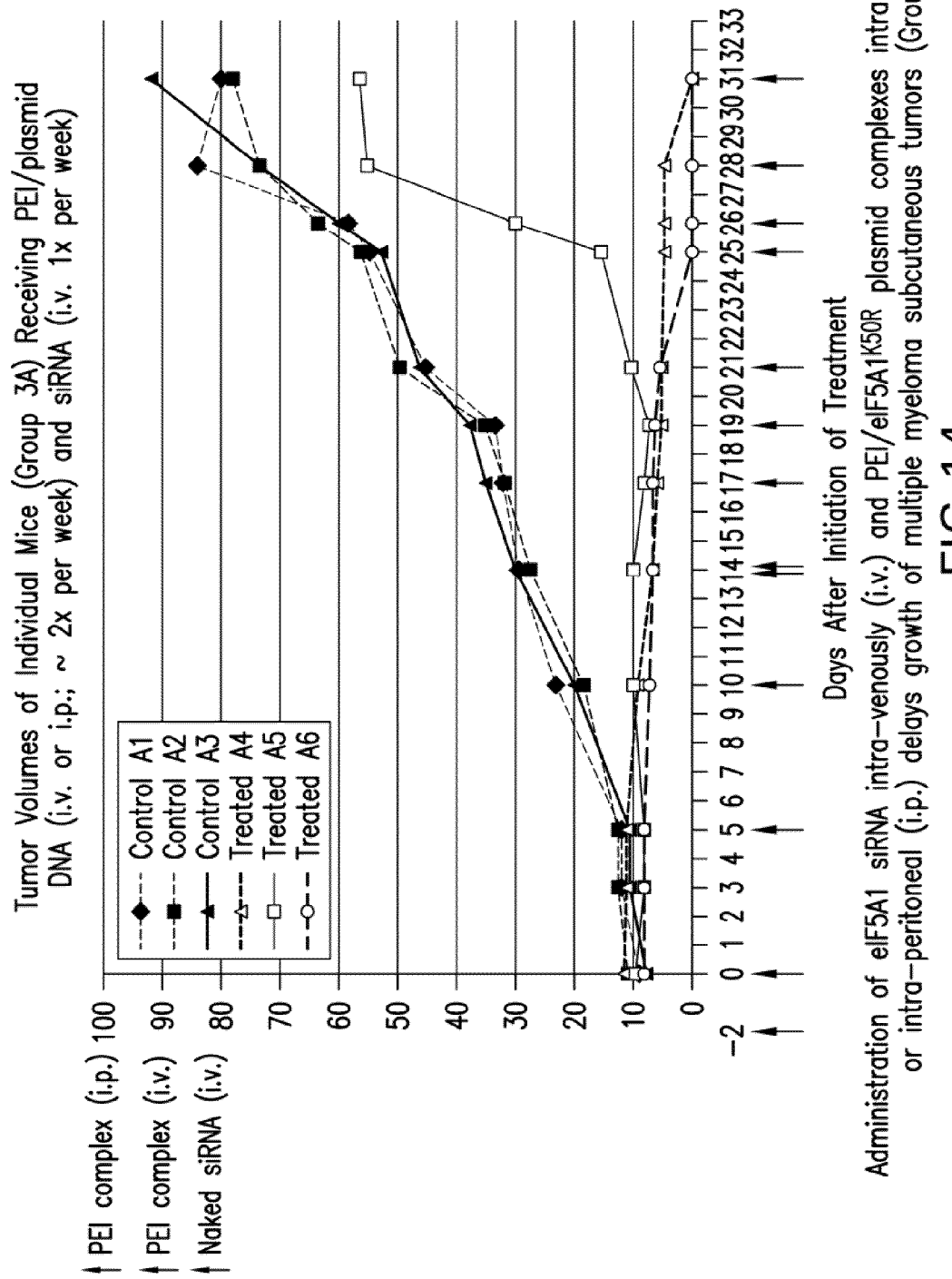
FIG. 14 shows that intra-venous co-administration of eIF5A1 plasmid and eIF5A1 siRNA delays growth of multiple myeloma subcutaneous tumours. See example 10.

Intra-Venous Co-Administration of eIF5A1 Plasmid and eIF5A1 siRNA Delays Growth of Multiple Myeloma Subcutaneous Tumours SCID mice were injected subcutaneously with KAS cells. When palpable tumours were observed treatment was initiated with an initial injection of 50 micrograms of either control siRNA (control group) or human eIF5A1 siRNA (treated group). Mice were subsequently treated by intra-venous (red arrows) or intra-peritoneal injections (green arrow)~twice per week with either PEI complexes containing pCpG-mcs (empty vector; control group A1, A2, and A3) or PEI complexes containing the RNAi-resistant plasmid pCpG-eIF5A1k50R (treated group; A4, A5, and A6). Mice continued to receive either control siRNA (control group A1, A2, and A3) or human eIF5A1 siRNA (treated group A4, A5, and A6) by i.v. injection (blue arrows) once per week. The data shown is the tumour volume for all the mice in each group. The data shown in FIG. 14 is the tumour volume for all the mice in each group.

Example 11

Figure 15:
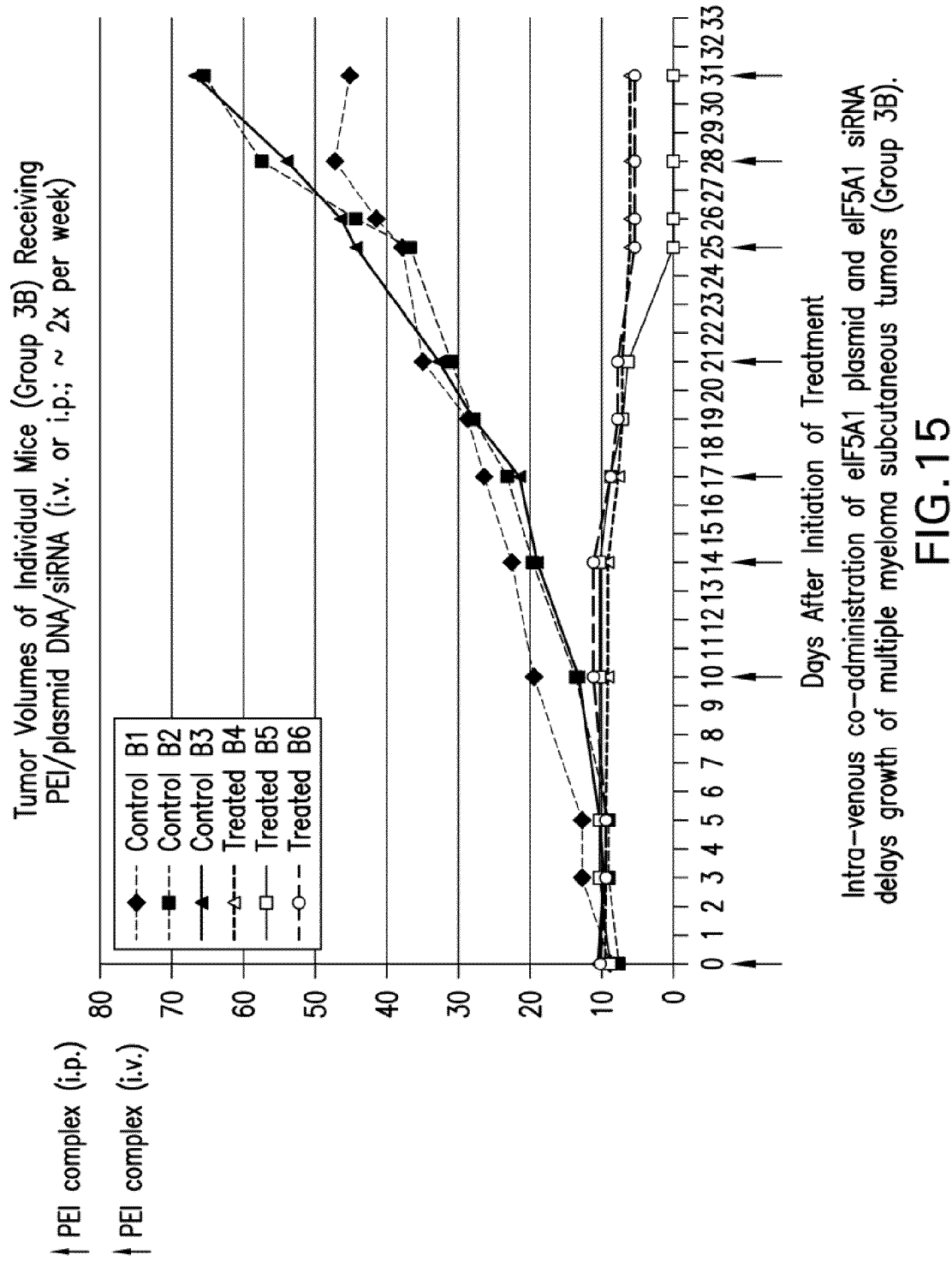
FIG. 15 shows that administration of eIF5A 1 siRNA intravenously (i.v.) and PEI/eIF5A1K50R plasmid complexes intra-venously (i.v.) or intra-peritoneal (i.p.) delays growth of multiple myeloma subcutaneous tumours. See example 11.

Administration of eIF5A1 siRNA Intra-Venously (i.v.) and PEI/eIF5A1K50R Plasmid Complexes Intra-Venously (i.v.) or Intra-Peritoneal (i.p.) Delays Growth of Multiple Myeloma Subcutaneous Tumours SCID mice were injected subcutaneously with KAS cells. When palpable tumours were observed treatment was initiated with an initial injection of 50 micrograms of either control siRNA (control group) or human eIF5A1 siRNA (treated group). Control mice were subsequently treated by intra-venous or intra-peritoneal injections once per week with PEI complexes containing pCpG-mcs (empty vector; control group was three mice: B1, B2, and B3). Treated mice were subsequently treated by intra-venous or intra-peritoneal injections~once per week with PEI complexes containing the RNAi-resistant plasmid pCpG-eIF5A1$^{K50R}$ (treated group; B4, B5, and B6). Mice continued to receive either control siRNA (control group B1, B2, and B3) or human eIF5A1 siRNA (treated group was three mice: B4, B5, and B6) by i.v. injection once per week. The experiment began with initial siRNA injection of 50 μg (day-2 on graph in FIG. 15). Subsequent injections used 20 micrograms of siRNA once weekly. The siRNA was given naked, i.e. no delivery vehicle. PEI complexes contained 20 μg of plasmid DNA. The initial PEI injection was given i.p. and subsequent injections were given i.v. The data shown in FIG. 15 is the tumor volume for all the mice in each group.

Figure 16:
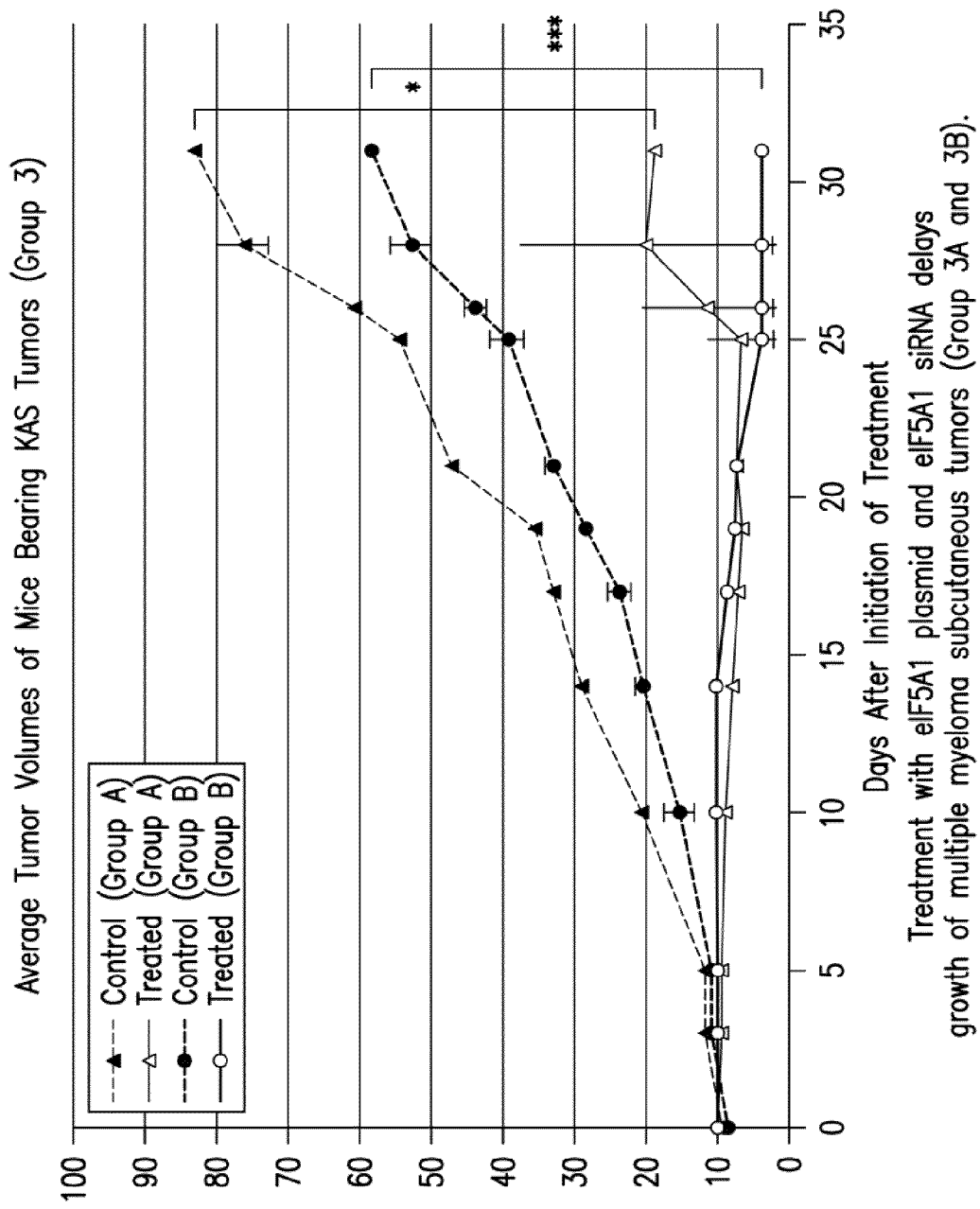
FIG. 16 shows that treatment with eIF5A1 plasmid and eIF5A1 siRNA delays growth of multiple myeloma subcutaneous tumours.

FIG. 16 provides an overlay of Example 10 and 11. SCID mice were injected subcutaneously with KAS cells. Treatment was initiated when palpable tumours were observed. One set of mice received i.v. injections of either control siRNA (control; Group A) or eIF5A1 siRNA (treated; Group A) once per week and either i.v. or i.p. of either PEI complexes containing pCpG-mcs (control; Group A) or PEI complexes containing the RNAi-resistant plasmid pCpG-eIF5A1$^{K50R}$ (treated; Group A). A second set of mice were given i.v. or i.p. injections~2 times per week with either PEI complexes containing pCpG-mcs (empty vector) and control siRNA (control; Group B.) or PEI complexes containing the RNAi-resistant plasmid pCpG-eIF5A1k50R and eIF5A1 siRNA (treated; Group B). The data shown is the average tumour volume for the mice in each group+/−standard error. Asterix denote statistical significance between treated and control groups (*=p<0.05; ***=p<0.001; n=3).

The protocols for preparing the PEI complexes and the siRNA are as described in previous examples.

Example 12

Figure 17A:
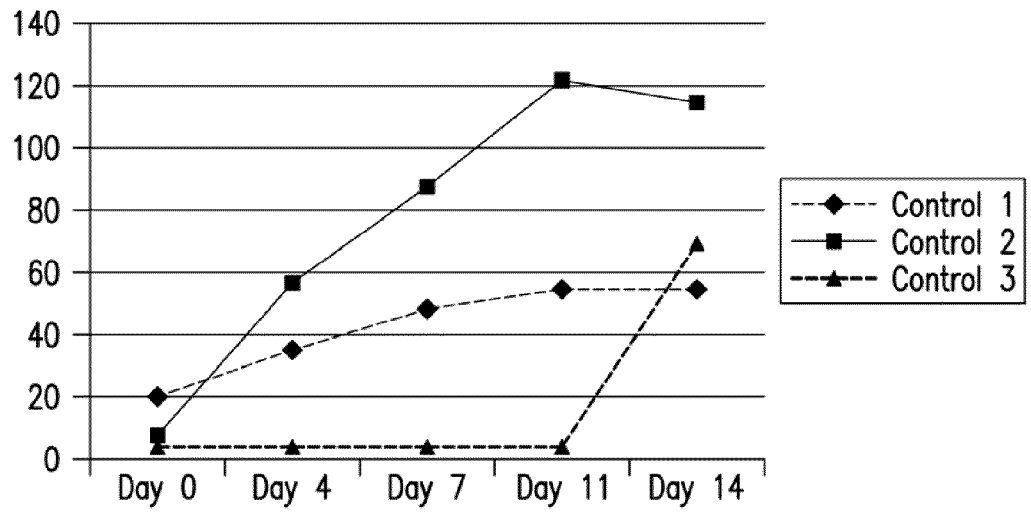
FIG. 17 shows that co-administration of eIF5A1 plasmid and eIF5A1 siRNA delays growth of multiple myeloma subcutaneous tumours and results in tumour shrinkage. See example 12.
Figure 17B:
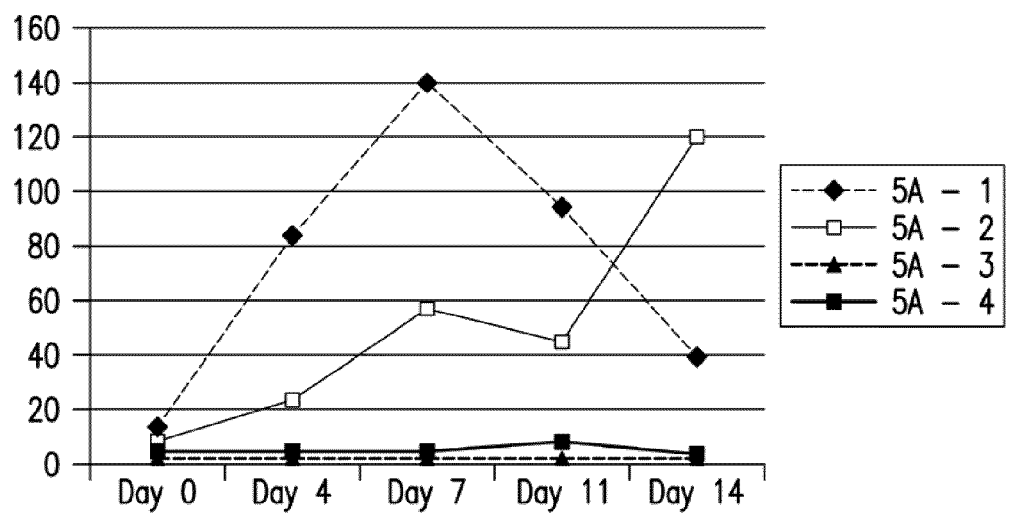

Co-Administration of eIF5A1 Plasmid and eIF5A1 siRNA Delays Growth of Multiple Myeloma Subcutaneous Tumours and Results in Tumour Shrinkage SCID mice were injected subcutaneously with KAS cells. Treatment was initiated when palpable tumours were observed. Control mice were injected intra-tumourally 2 times per week with PEI complexes containing pCpG-mcs (empty vector) and control siRNA (control group had 3 mice: control 1, control 2, and control 3). Treated mice were injected intra-tumourally 2 times per week with PEI complexes containing the RNAi-resistant plasmid pCpG-eIF5A1$^{K50R}$ and eIF5A1 siRNA (treated group contained 4 mice: 5A-1, 5A-2, 5A-3, and 5A-4). The intra-tumoral rejections of PEI complexes contained both 20 μg of plasmid DNA and 10 μg of siRNA. The data shown in FIG. 17 is the tumour volume for all the mice in each group.

Example 13

Administration of eIF5A1 siRNA Intra-Venously (i.v.) and PEI/eIF5A1$^{K50R}$ Plasmid Complexes Intra-Tumourally (i.t.) Results in Tumour Shrinkage of Multiple Myeloma Subcutaneous Tumours SCID mice were injected subcutaneously with KAS cells. When palpable tumours were observed treatment was initiated with an initial injection of 50 micrograms of either control siRNA (control group had three mice: control 1, control 2 and control 3) or human eIF5A1 siRNA (treated group had 3 mice: 5A-1, 5A-2, 5A-3). Control mice were subsequently treated by intra-tumoural injections 2 times per week with PEI complexes containing pCpG-mcs (20 μg) (control group 1-3). Treated mice were subsequently treated by intra-tumoural injections 2 times per week with PEI complexes containing the RNAi-resistant plasmid pCpG-eIF5A1$^{K50R}$ (20 μg) (5A-1, 5A-2, 5A-3). Control mice continued to receive either control siRNA (20 μg) by tail vein i.v. injection twice per week. Treated mice continued to receive human eIF5A1 siRNA (20 μg) by tail vein i.v. injection twice per week. The injections were give 48 hours prior to the intra-tumoural injections. The siRNA was given as naked siRNA, i.e. no delivery vehicle. The data shown in FIG. 18 is the tumour volume for all the mice in each group.

Example 14

Figure 19:
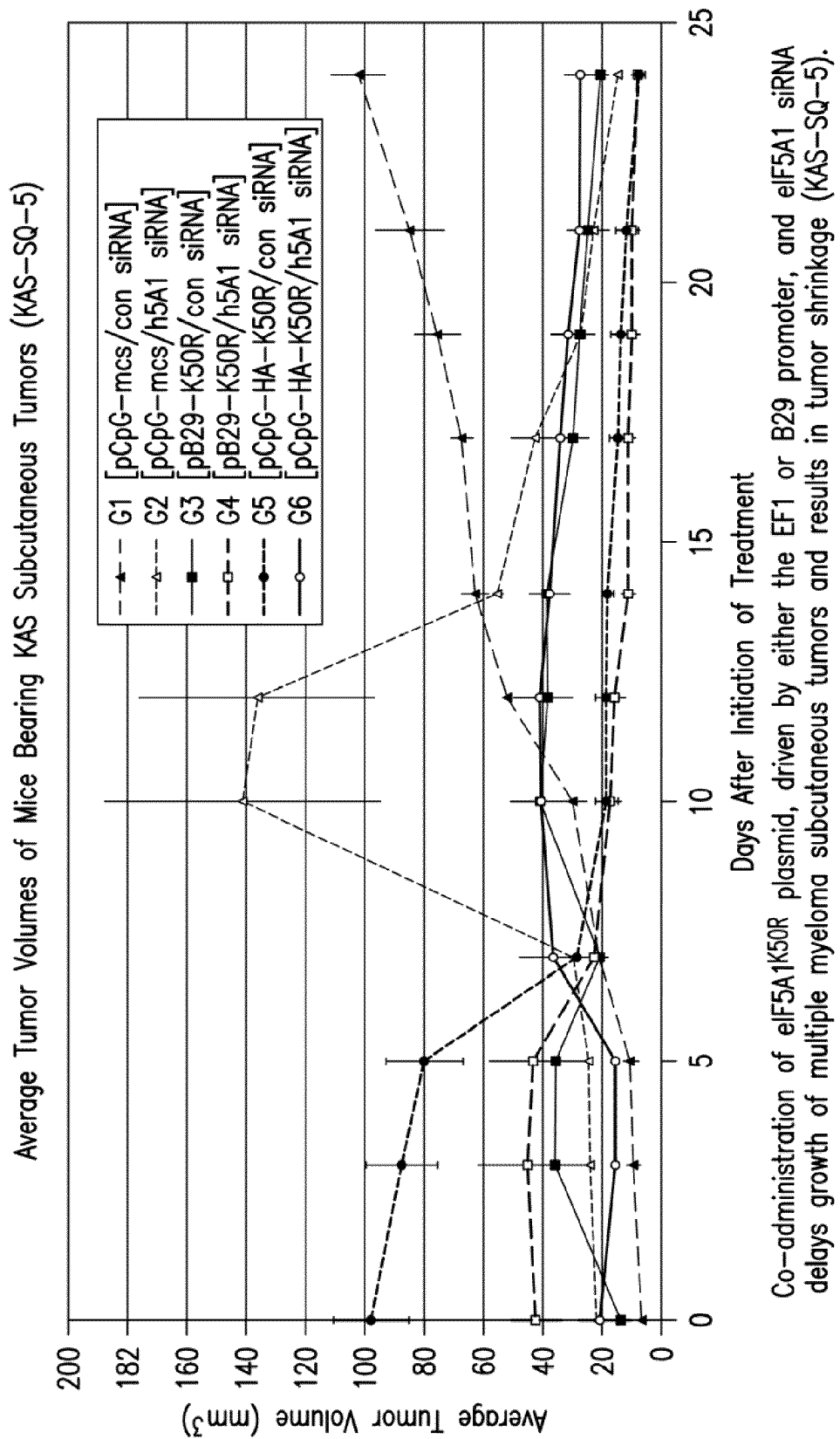
FIG. 19 shows co-administration of eIF5A1$^{K50R}$ plasmid, driven by either the EF1 or B29 promoter, and eIF5A1 siRNA delays growth of multiple myeloma subcutaneous tumours and results in tumour shrinkage (KAS-SQ-5). See example 14.

Co-Administration of eIF5A1$^{K50R}$ Plasmid, Driven by either the EF1 or B29 Promoter, and eIF5A1 siRNA Delays Growth of Multiple Myeloma Subcutaneous Tumours and Results in Tumour Shrinkage SCID mice were injected subcutaneously with KAS cells. Treatment was initiated when palpable tumours were observed. Mice were injected intra-tumourally 2 times per week with PEI complexes containing either control vector (G1 and G2) or an eIF5A1 plasmid driven by either the B29 promoter (G3 and G4) or the EF1 promoter (G5 and G6) and either control siRNA (G1, G3, G5) or h5A1 siRNA (G2, G4, G6). The data shown is the average tumour volume+/−standard error for each group. Note: the B29 promoter was intended as a B-cell-specific promoter. However, although the B29 promoter/mCMV enhancer used in this study was found to drive high expression of HA-eIF5A1$^{K50R}$ in KAS cells in vitro, it does not appear to be B-cell-specific (likely due to CMV enhancer). See FIG. 19.

Example 15

Figure 20:
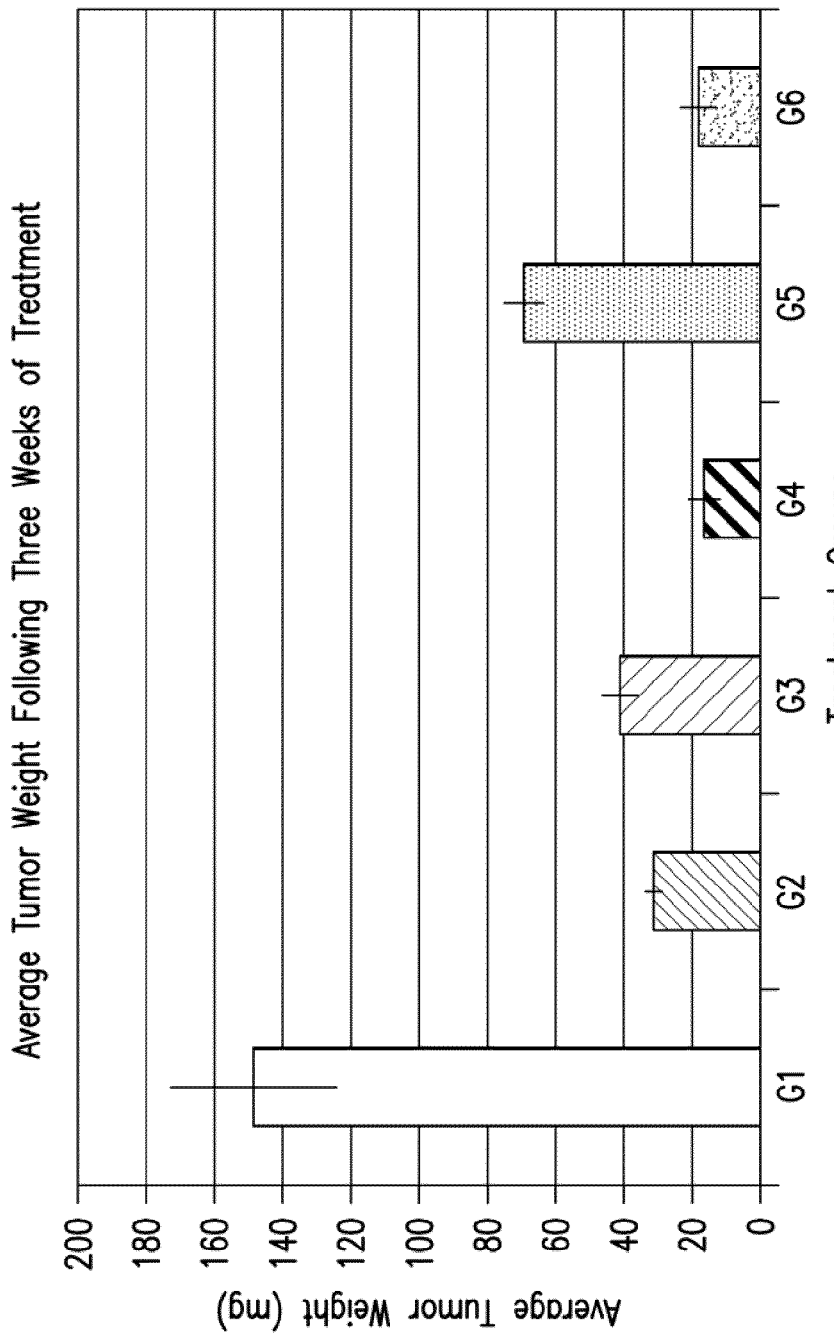
FIG. 20 shows co-administration of eIF5A1 siRNA increases anti-tumor effect of eIF5A1$^{K50R}$ plasmid, driven by either the EF1 or B29 promoter, on multiple myeloma subcutaneous tumours and results in reduced tumor burden (KAS-SQ-5). See example 15.

Co-Administration of eIF5A1 siRNA Increases Anti-Tumor Effect of eIF5A1$^{K50R}$ Plasmid, Driven by either the EF1 or B29 Promoter, on Multiple Myeloma Subcutaneous Tumours and Results in Reduced Tumor Burden SCID mice were injected subcutaneously with KAS cells. Treatment was initiated when palpable tumours were observed. Mice were injected intra-tumourally 2 times per week with PEI complexes containing either control vector (G1 and G2) or an eIF5A1 plasmid driven by either the B29 promoter (G3 and G4) or the EF1 promoter (G5 and G6) and either control siRNA (G1, G3, G5) or h5A1 siRNA (G2, G4, G6). The mice were sacrificed 24 days after the initiation of treatment and the subcutaneous tumor was removed and weighed. The data shown is the average tumor weight+/− standard error for all groups. See FIG. 20.

Figure 21:
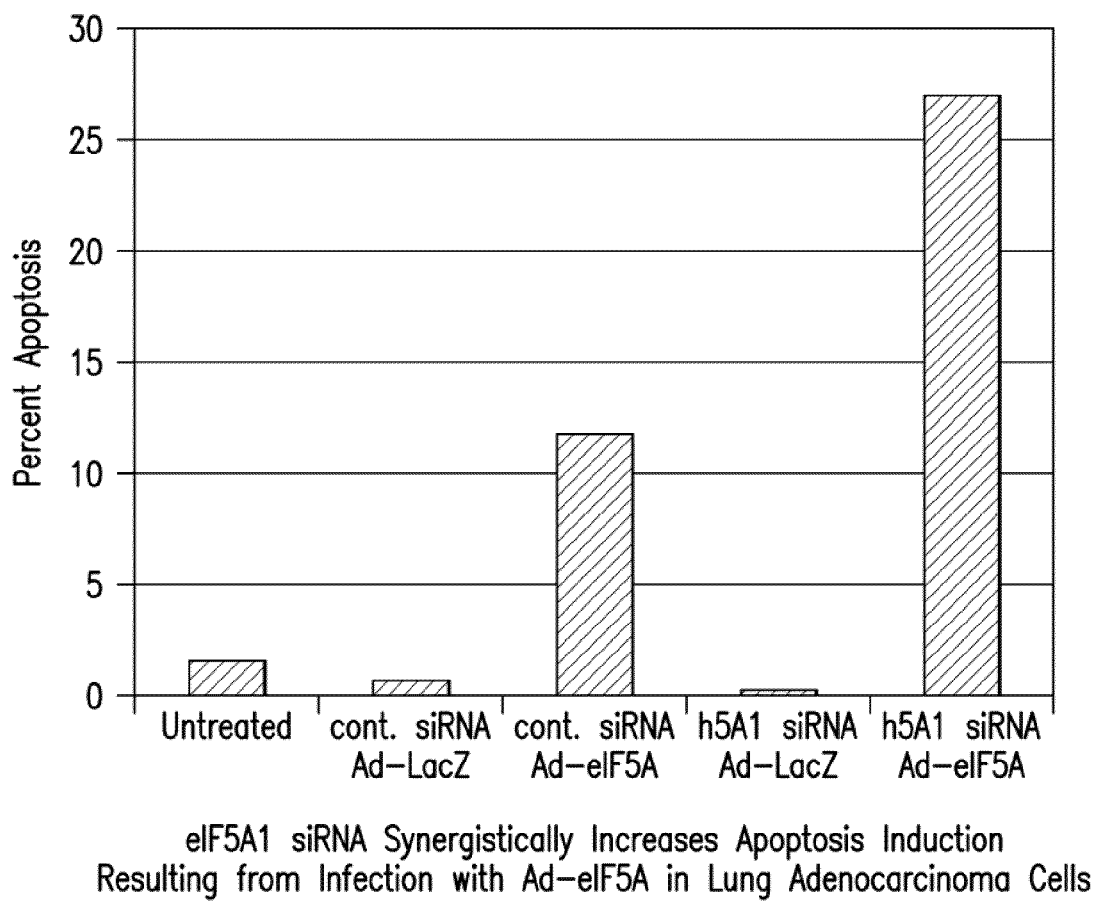
FIG. 21 shows eIF5A1 siRNA synergistically increases apoptosis resulting from infection with Ad-eIF5A in lung adenocarcinoma cells. See example 16.

Example 16 eIF5A1 siRNA Synergistically Increases Apoptosis Induction Resulting from Infection with Ad-eIF5A in Lung Adenocarcinoma Cells A549 cells were infected with either Ad-LacZ or Ad-eIF5A. Cells were transfected with either a control siRNA or an siRNA targeting human eIF5A1 (h5A1) by adding the transfection media to cells immediately following addition of the virus. Four hours after transfection with the siRNA and infection with virus, the media was replaced with fresh media and the cells were incubated for 72 hours prior to labelling with Annexin/PI to detect apoptotic cells. Note: over-expression of eIF5A in this cell line results in the accumulation of unhypusinated eIF5A due to limiting amounts of DHS and DOHH and therefore results in same pro-apoptotic effect as over-expression of eIF5A$^{K50R}$. These data indicate that the synergistic effect in apoptosis caused by simultaneous suppression of hypusinated eIF5A and over-expression of unhypusinated eIF5A is observed in non-myeloma tumour-types as well. See FIG. 21.

Example 17

Construction of Plasmid pExp5A pExp5A is an expression plasmid with reduced CpG dinucleotides designed to drive expression of human eIF5A1$^{K50R}$ predominantly in cells of B cell lineage. The vector is derived from pCpG-LacZ, a plasmid completely devoid of CpG dinucleotides (Invivogen). All the elements required for replication and selection in *E. coli* are free of CpG dinucleotides. The original CMV enhancer/promoter and LacZ gene from the CpG-LacZ vector have been replaced with a human minimal B cell specific promoter (B29/CD79b; Invivogen) and human eIF5A1$^{K50R}$, respectively, in order to drive B-cell specific expression of eIF5A1$^{K50R}$. The B29 DHS4.4 3' enhancer has been introduced into the plasmid downstream of the eIF5A1 expression cassette in order to enhance activity of the B29 promoter and reduce expression in non-B cells (Malone et al. 2006. B29 gene silencing in pituitary cells is regulated by its 3' enhancer. J. Mol. Biol. 362: 173-183). Incorporation of the B29 minimal promoter, eIF5A1$^{K50R}$, and the B29 DHS4.4 3' enhancer has introduced 32 CpG dinucleotides into the vector.

Elements for Expression in *E. coli*

Origin of replication: *E. coli* R6K gamma ori.

* Due to the presence of the R6K gamma origin of replication, pCpG plasmids can only be amplified in *E. coli* mutant strain expressing a pir mutant gene. They will not replicate in standard *E. coli* strains. Therefore, pCpG plasmids are provided with the *E. coli* GT115 strain, a pir mutant also deficient in Dcm methylation (Invivogen).

Bacterial promoter: EM2K, a CpG-free version of the bacterial EM7 promoter.

Selectable marker: Zeocin™ resistance gene; a synthetic allele with no CpGs.

Elements for Expression in Mammalian Cells

Mammalian promoter: the human −167 bp minimal B29 (CD79b) promoter for tissue-specific expression in B cells. A synthetic intron (I 140) is also present in the 5'UTR.

Polyadenylation signal: a CpG dinucleotide-free version of the late SV40 polyadenylation signal.

3' Enhancer: the human B29 DHS4.4 3' enhancer.

MAR: Two CpG-free Matrix attached regions (MAR) are present between the bacterial and mammalian transcription units. One MAR is derived from the 5' region of the human IFN-β gene and one from the 5' region of the β-globin gene.

The predicted Sequence of pExp5A (3371 bp is provided at FIG. 23.

Amino Acid Sequence of eIF5A1$^{K50R}$ (SEQ ID NO: 6)

* K50R mutation is underlined

Amino Acid Sequence of eIF5A1$^{K50R}$
* K50R mutation is underlined (SEQ ID NO: 6)
MADDLDFETGDAGASATFPMQCSALRKNGFVVLKGRPCKIVEMSTSKTG

RHGHAKVHLVGIDIFTGKKYEDICPSTHNMDVPNIKRNDFQLIGIQDGY

LSLLQDSGEVREDLRLPEGDLGKEIEQKYDCGEEILITVLSAMTEEAAV

AIKAMAK

Construction of pExp5A—Outline of Construction:
Step 1: Cloning of B29 DHS4.4 3' enhancer and subcloning into pGEM T easy (Promega)—creates pGEM-4.4enh #8.
Step 2: Subcloning of minimal B29 promoter into pCpG-LacZ (Invivogen)—creates B29-5#3.
Step 3: Subcloning of HA-eIF5A1$^{K50R}$ into B29-5#3 vector—creates B29-5#3-eIF5A1$^{K50R}$.
Step 4: Creation of new multiple cloning site in pCpG-mcs (Invivogen)—creates pCpG-Linker4.
Step 5: Subcloning of B29 DS4.4 3' enhancer into pCpG-Linker4—creates pCpG-DHS4.4.
Step 6: Subcloning of B29 promoter+HA-eIF5A1$^{K50R}$+SV40 pA expression cassette into pCpG-DHS4.4 creates pExp-5.
Step 7: Replacement of HA-eIF5A1$^{K50R}$ in pExp-5 with non-HA eIF5A1$^{K50R}$ creates final vector, pExp5A.
Construction in Detail:
Step 1: Cloning of B29 DHS4.4 3' enhancer and subcloning into pGEM T easy (Promega)—creates pGEM-4.4enh #8.

The B29 DHS4.4 3' enhancer was cloned by PCR from genomic DNA isolated from KAS cells (human multiple myeloma cell line) using the following primers: forward 5'-CAGCAAGGGAGCACCTATG-3' (SEQ ID NO: 7) and reverse 5'-GTTGCAGTGAGCGGAGATG-3' (SEQ ID NO: 8). The primers were designed using the sequence of the human CD79B/GH-1 Intergenic region (Accession AB062674). The resulting 608 bp PCR fragment was subcloned into the pGEM® T easy cloning vector (Promega) and sequenced. Komatsu et al. 2002. Novel regulatory regions found downstream of the rat B29/Ig-b gene. Eur. J. Biochem. 269: 1227-1236.

Sequence of B29 DHS4.4 3' enhancer PCR fragment (297 Bp) in pGEM-4.4enh #8 (SEQ ID NO: 9)

```
ACCACCCTGGGCCAGGCTGGGCCAAGCCAGGCGGCCCCTGTGTTTTCCCC
AGTCTCTGGGCTGCTGGAGGGAACCAGGTTGTTTTGGCATCAGCCTCTAC
TGAGCCGGAGCCCTTCCTTTCCTGCTGCTTTGCATAGTGGCACTAATTCC
GTCCTCCTACCTCCACCAGGGACCTAGGCAGCCGGGTAGATGGTGGGAGG
AGGCTTCACTTCTCCCCCAAGCAGGGTCTCCACCTGCTTGAGGCTGCCCT
GGGTTGGGGGAGGCCTTGGCTTTACCTAAAGACTTTTTAACACCTCT
```

+4.4 regions contains several transcription
factor binding sites
SRY GTTGTTT
GATA CATCAGC
OCT-X GCTGCTTTGCATAG
(residues 124-137 of SEQ ID NO: 9)
NF-KB GAGGCTGCCCBU
(residues 240-249 of SEQ ID NO: 9)

Alignment of B29 DHS4.4 3' enhancer PCR fragment (297 bp (SEQ ID NO: 9)) in pGEM-4.4enh #8 with sequence of the human CD79B/GH-1 Intergenic region (Accession AB062674 (SEQ ID NO: 10)). The consensus sequence is disclosed as SEQ ID NO: 9.

```
           1         10        20        30        40        50        60        70        80        90       100       110       120   130
           |---------+---------+---------+---------+---------+---------+---------+---------+---------+---------+---------+---------+----|
genb       GGGAACAGCTGCCAGCTGGGAGACCAAGTGCAATCAACCTGACGTGCACGTGCAAAGCCTCCCTCCCACTTCCTGTTGTCTCCACTTCCTGAGGGAATCCTTCGAGGCCCCTCTGCTATTCCTG
PCR        ...............................................................................................................................
Consensus 131       140       150       160       170       180       190       200       210       220       230       240       250   260
           |---------+---------+---------+---------+---------+---------+---------+---------+---------+---------+---------+---------+----|
genb       CTCTGAATTCCAGCCTCAAGGAGCACCTGCTGAGCCGACAAGCTACATGCTGTGGGAGCTGCCAGTTTAACTGGGGAATCAAGAACTAGTGAGAACAGTGCCAATTTTCACCAGAATTCCCTGGAATTCCAGGTGG
PCR        ...............................................................................................................................
Consensus 261       270       280       290       300       310       320       330       340       350       360       370       380   390
           |---------+---------+---------+---------+---------+---------+---------+---------+---------+---------+---------+---------+----|
genb       GGCAGGTGGGTAAGGCCCCCACGCTGCAGTTTCAGGTAAATCTCTCCACCACCCCTGGGCCAGGCTGGGCCAAGCCAGGCGGGCCGGGCCAAGCCAGGAACCAGGAACCAGGTTGT
PCR        ..........................................ACCACCCCTGGGCCAGGCTGGGCCAAGCCAGGCGGGCCGGGCCAAGCCAGGAACCAGGAACCAGGTTGT
Consensus                                             ACCACCCCTGGGCCAGGCTGGGCCAAGCCAGGCGGGCCGGGCCAAGCCAGGAACCAGGAACCAGGTTGT 391       400       410       420       430       440       450       460       470       480       490       500       510   520
           |---------+---------+---------+---------+---------+---------+---------+---------+---------+---------+---------+---------+----|
genb       TTTTGACATCAGCCTCTCACCTGCTTGAGCCGGAGCCCTTCCTGTGCTTTTCATTCCCTGCTTTTACATAGTAGCACTGATTCCATCAGTAGCCGGTAGCCGGATGGTGAGAGAGGCTTCACTTC
PCR        TTTTGACATCAGCCTCTCACTGAGCCGGAGCCCTTCCTGTGCTTTTCATTCCCTGCTTTTACATAGTAGCACTGATTCCATCAGTAGCCGGTAGCCGGATGGTGAGAGAGGCTTCACTTC
Consensus  TTTTGACATCAGCCTCTCACTGAGCCGGAGCCCTTCCTGTGCTTTTCATTCCCTGCTTTTACATAGTAGCACTGATTCCATCAGTAGCCGGTAGCCGGATGGTGAGAGAGGCTTCACTTC 521       530       540       550       560       570       580       590       600       610       620       630       640   650
           |---------+---------+---------+---------+---------+---------+---------+---------+---------+---------+---------+---------+----|
genb       TCCCCAAGCAGGATCTCCACCTGCTTGAGGCTGCCTCCCTGAGGCTTGAGGCTGCCTGGGTTGGGGAGGCCTTGGCTTTAACCTTTTAACACCTTTAACACCCTCTGAACAACAACAGTTTCCCTGAACACTTTCCTGAGACTTTGAAGCTCTTGTTTTATTTA
PCR        TCCCCAAGCAGGATCTCCACCTGCTTGAGGCTGCCTCCCTGAGGCTTGAGGCTGCCTGGGTTGGGGAGGCCTTGGCTTTAACCTTTAACACCCTCTGAACAACAACAGTTTCCCTGAACACTTTGAAGCTCTTGTTTTATTTA
Consensus  TCCCCAAGCAGGATCTCCACCTGCTTGAGGCTGCCTCCCTGAGGCTTGAGGCTGCCTGGGTTGGGGAGGCCTTGGCTTTAACCTTTAACACCCTCTGAACAACAACAGTTTCCCTGAACACTTTGAAGCTCTTGTTTTATTTA 651       660       670       680       690       700       710       720       730       740       750       760       770   780
           |---------+---------+---------+---------+---------+---------+---------+---------+---------+---------+---------+---------+----|
genb       TTTTATTTATTTATTTATTACTTATTATTATTTGCAGACAGAGTCTCACTCTGTTGCCCAGACTGGAGTGCAGTGGCACCATCTCCCGCTCACTGCAACCTCCGTCTCCTGAGTTCAAGCAATTCTCCT
PCR        TTTTATTTATTTATTTATTACTTATTATTATTTGCAGACAGAGTCTCACTCTGTTGCCCAGACTGGAGTGCAGTGGCACCATCTCCCGCTCACTGCAACCTCCGTCTCCTGAGTTCAAGCAATTCTCCT
Consensus 781       790       800
           |---------+---------+--|
genb       GCCTCAGCCTCCCAAGTACC
PCR        ....................
Consensus
```

Step 2: Subcloning of minimal B29 promoter into pCpG-LacZ (Invivogen)—creates B29-5 #3.

The minimal −167 human B29 promoter was amplified from a commercial plasmid bearing the full length human B29 promoter (pDrive-hB29; Invivogen) using the following primers: forward 5'-CCA ACTAGTGCGACCGCCAAACCTTAGC-3' (SEQ ID NO: 11); reverse: 5'-CAA AAGCTTGACAACGTCCGAGGCTCCTTGG-3' (SEQ ID NO: 12). The resulting PCR fragment was digested with SpeI and HindIII and ligated into the SpeI and HindIII sites of the pCpG-LacZ vector (Invivogen) to create B29-5 #3.

Sequence of B29 minimal promoter PCR fragment (188 bp) in B29-5 #3 (SEQ ID NO: 13)

GCGACCGCCAAACCTTAGCGGCCCAGCTGACAAAAGCCTGCCCTCCCCCA

GGGTCCCCGGAGAGCTGGTGCCTCCCCTGGGTCCCAATTTGCATGGCAGG

AAGGGGCCTGGTGAGGAAGAGGCGGGGAGGGGACAGGCTGCAGCCGGTG

CAGTTACACGTTTTCCTCCAAGGAGCCTCGGACGTTGTC

Alignment of B29 minimal promoter PCR fragment (B29min) in B29-5 #3 (SEQ ID NO: 13) with full length human B29 promoter from pDrive-hB29 (SEQ ID NO: 14). The consensus sequence is disclosed as SEQ ID NO: 13.

```
                    10         20         30         40         50         60         70         80         90        100        110        120        130
           1  ----------+----------+----------+----------+----------+----------+----------+----------+----------+----------+----------+----------+----------
B29_prom      CCTGCAGGGCCCCACTAGTAAACGAGAGGTTGTGAGGAGGTGGAGAGTGGACAGAGGGCACCACGAGATCTTTCCTCTCCTGGGGTCGAGGATGAGAGGATGAGAGCAAAAAGAAGCTGCCAGGAAAC
B29_min       .............................................................................................................................
Consensus     .............................................................................................................................

140        150        160        170        180        190        200        210        220        230        240        250        260
         131  ----------+----------+----------+----------+----------+----------+----------+----------+----------+----------+----------+----------+----------
B29_prom      ATAAAATTCAGAGGGCTCAGTCTGCACGAAGGTCTGCAAGCTGAGTCTGCAAGCATGCATGCTTGTGCTACACTTGTGCCCTTGCCACACAAGGGCATCTCTGAAGGGGCTGCACTGGACCCCAGGGCAGGGGCAAAAGT
B29_min       .............................................................................................................................
Consensus     .............................................................................................................................

270        280        290        300        310        320        330        340        350        360        370        380        390
         261  ----------+----------+----------+----------+----------+----------+----------+----------+----------+----------+----------+----------+----------
B29_prom      GAGTTTATATCAGTTCCTGAGCACTGGCTCCATCCAGCACTCTGAGGACAGGCAGGATACAGCTGGAGGACCTGAGGGGCTCCCCACACCAGCTCCTGTTCCTGCCCAAGACCCCCTGGACCTGCAG
B29_min       .............................................................................................................................
Consensus     .............................................................................................................................

400        410        420        430        440        450        460        470        480        490        500        510        520
         391  ----------+----------+----------+----------+----------+----------+----------+----------+----------+----------+----------+----------+----------
B29_prom      ACAACAATTCAACGACTCAGAGTTCCCAGTGAAGAGGCTCCTGAAGAACTCCCTGAAGTTAAGAACTGGCTGCGTGGTGGATTTTCGCAGCTGTCTCCACTACATCCACCCTGTTTGCAGCCCTACTATCT
B29_min       .............................................................................................................................
Consensus     .............................................................................................................................

530        540        550        560        570        580        590        600        610        620        630        640        650
         521  ----------+----------+----------+----------+----------+----------+----------+----------+----------+----------+----------+----------+----------
B29_prom      TTCACAGCATGAGGAGGAGGGCCTCTCCACCAAGAACTTCTCTCCGACTGACCTGACCTGGTCCAGTGCCTGCTGCCCACACCCAGTCTTCCTGCCAAAGCTGTCTCCACCTGACTGGCTGTGTGGGTCTGTGGCTGCGTGGCTGCCTCCCATCCTCCAGGGGTCAGGACAGAGG
B29_min       .............................................................................................................................
Consensus     .............................................................................................................................

660        670        680        690        700        710        720        730        740        750        760        770        780
         651  ----------+----------+----------+----------+----------+----------+----------+----------+----------+----------+----------+----------+----------
B29_prom      ATGGCTGCCTGCACTCCAGCCAAGAGGCTCTGCTCTGCGGCCCCTCCAGATGCCTGACCTGGTCTGTGGCTGCGTGCCTCCTTCTTCAGTGCTCCTCCCGTCTGGGTGAGGAATAGTTCAGGACAGAGG
B29_min       .............................................................................................................................
Consensus     .............................................................................................................................

790        800        810        820        830        840        850        860        870        880        890        900        910
         781  ----------+----------+----------+----------+----------+----------+----------+----------+----------+----------+----------+----------+----------
B29_prom      AGCTTAAGTTCAGTTCATTCATTAGGACAGGTGCCTATTTCGCTCACGGCCCCAGGAATAGAGACTTGCCGGGCTCGGCCCTTCGGGAGTTGGCAGACGGCAGAGGGGAGGAGGCTGCTGCCCAGGGGATGA
B29_min       .............................................................................................................................
Consensus     .............................................................................................................................

920        930        940        950        960        970        980        990       1000       1010       1020       1030       1040
         911  ----------+----------+----------+----------+----------+----------+----------+----------+----------+----------+----------+----------+----------
B29_prom      CCACCGGTTGGGGTAAGCACAGACAGAGGGGAGCACAGGCTTCCCCCAGAGAGACTGAGAGGCCATCCACAGAGGAGCCCCCAGCTGTGCTGCTGCCCAGCAAGCTGGGCGACCACCAAACCTTAGCGGC
B29_min       ..................................................................................................................GCGACCACCAAACCTTAGCGGC
Consensus     ..................................................................................................................GCGACCACCAAACCTTAGCGGC 1050       1060       1070       1080       1090       1100       1110       1120       1130       1140       1150       1160       1170
        1041  ----------+----------+----------+----------+----------+----------+----------+----------+----------+----------+----------+----------+----------
B29_prom      CCAGCTGACAAAAACCTGCCCCTCCCCAGGGTCCCGGAGAACTGGTGCCTCCCCTGGGTCCAATTTGCATGCCAGAAGGAGGCGGAGAAGGAGCCTGGTGAGGAATGGCCAGAAGAGGCGGTACAACCGGTGCAG
B29_min       CCAGCTGACAAAAACCTGCCCCTCCCCAGGGTCCCGGAGAACTGGTGCCTCCCCTGGGTCCAATTTGCATGCCAGAAGGAGGCGGAGAAGGAGCCTGGTGAGGAATGGCCAGAAGAGGCGGTACAACCGGTGCAG
Consensus     CCAGCTGACAAAAACCTGCCCCTCCCCAGGGTCCCGGAGAACTGGTGCCTCCCCTGGGTCCAATTTGCATGCCAGAAGGAGGCGGAGAAGGAGCCTGGTGAGGAATGGCCAGAAGAGGCGGTACAACCGGTGCAG 1180       1190       1200       1210       1220       1230  1237
        1171  ----------+----------+----------+----------+----------+----------+-------
B29_prom      TTACACGTTTTCTCCAAGGAGCCTCGAACGTTGTC
B29_min       TTACACGTTTTCTCCAAGGAGCCTCGAACGTTGTC
Consensus     TTACACGTTTTCTCCAAGGAGCCTCGAACGTTGTC
```

Step 3: Subcloning of HA-eIF5A1$^{K50R}$ into B29-5#3 vector—creates pB29-eIF5A1K50R_7.

HA-eIF5A1$^{K50R}$ was amplified by PCR using the pHM6-eIF5A1$^{K50R}$ as a DNA template and the following primers: forward 5'-CGCCATGGACATGTACCCTTACGACGTC-CCAGACTACGCTGCAGATGATTTGGACTT CGAG-3' (SEQ ID NO: 15) and reverse 5'-CGC GCTAGCCAGTTATTTTGCCATCGCC-3' (SEQ ID NO: 16). The resulting PCR fragment was digested with NcoI and NheI and subcloned into the NcoI and NheI sites of B29-5 #3 to replace LacZ.

Sequence of HA-eIF5A1$^{K50R}$ PCR fragment (497 bp) in pB29-eIF5A1K50R_7 (SEQ ID NO: 17).

```
ACATGTACCCTTACGACGTCCCAGACTACGCTGCAGATGATTTGGACTTC
GAGACAGGAGATGCAGGGGCCTCAGCCACCTTCCCAATGCAGTGCTCAGC
ATTACGTAAGAATGGTTTTGTGGTGCTCAAGGGCCGGCCATGTAAGATCG
TCGAGATGTCTACTTCGAAGACTGGCAGGCATGGCCATGCCAAGGTCCAT
CTGGTTGGCATTGATATTTTTACTGGGAAGAAATATGAAGATATCTGCCC
GTCGACTCATAACATGGATGTCCCCAACATCAAAAGGAATGATTTCCAGC
TGATTGGCATCCAGGATGGGTACCTATCCCTGCTCCAGGACAGTGGGGAG
GTACGAGAGGACCTTCGTCTGCCTGAGGGAGACCTTGGCAAGGAGATTGA
GCAGAAGTATGACTGTGGAGAAGAGATCCTGATCACAGTGCTGTCCGCCA
TGACAGAGGAGGCAGCTGTTGCAATCAAGGCGATGGCAAAATAACTG
```

Translation of HA-eIF5A1$^{K50R}$ PCR fragment in pB29-eIF5A1K50R_7 (SEQ ID NO: 18) HA epitope eIF5A1$^{K50R}$ K50R MD<u>MYPYDVPDYA</u>ADDLDFETGDAGASATFPMQCSALRKNGFVVLKGRPCKI

VEMSTSKTGRHGHAKVHLVGIDIFTGKKYEDICPSTHNMDVPNIKRNDF

QLIGIQDGYLSLLQDSGEVREDLRLPEGDLGKEIEQKYDCGEEILITVLSA

MTEEAAVAIKAMAK

Alignment of HA-eIF5A1$^{K50R}$ PCR fragment in pB29-eIF5A1K50R_7 (SEQ ID NO: 18) with human eIF5A1 (Accession #NP_001961 (SEQ ID NO: 19)). The consensus sequence is disclosed as residues 12-165 of SEQ ID NO: 18.

vector was then ligated to a synthetic linker with EcoRI sticky ends to create a promoterless vector with a new multiple cloning site (pCpG-Linker4). SEQ ID NOS 20-21 are disclosed below, respectively, in order of appearance.

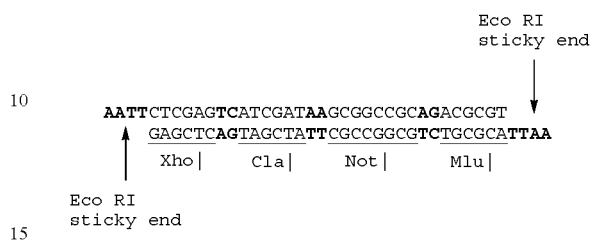

Synthetic Linker, Linker4 with two Eco RI sticky ends
Sequence of region surrounding new multiple cloning site in pCpG-Linker4 (SEQ ID NO: 22)

```
GGCATGTGAACTGGCTGTCTTGGTTTTCATCTGTACTTCATCTGCTACCT
CTGTGACCTGAAACATATTTATAATTCCATTAAGCTGTGCATATGATAGA
TTTATCATATGTATTTTCCTTAAAGGATTTTTGTAAGAACTAATTGAATT
GATACCTGTAAAGTCTTTATCACACTACCCAATAAATAATAAATCTCTTT
GTTCAGCTCTCTGTTTCTATAAATATGTACAAGTTTTATTGTTTTTAGTG
GTAGTGATTTTATTCTCTTTCTATATATATACACACACATGTGTGCATTC
ATAAATATATACAATTTTTATGAATAAAAAATTATTAGCAATCAATATTG
AAAACCACTGATTTTTGTTTATGTGAGCAAACAGCAGATTAAAAGGAATT
CTCGAGTCATCGATAAGCGGCCGCAGACGCGTAATTCAGTCAATATGTTC
ACCCCAAAAAGCTGTTTGTTAACTTGCCAACCTCATTCTAAAATGTATA
TAGAAGCCCAAAAGACAATAACAAAAATATTCTTGTAGAACAAAATGGGA
AAGAATGTTCCACTAAATATCAAGATTTAGAGCAAAGCATGAGATGTGTG
GGGATAGACAGTGAGGCTGATAAAATAGAGTAGAGCTCAGAAACAGACCC
ATTGATATATGTAAGTGACCTATGAAAAAATATGGCATTTTACAATGGG
AAAATGATGATCTTTTTCTTTTTTAGAAAAACAGGGAAATATATTTATAT
GTAAAAAATAAAAGGGAACCCATATGTCATACCATACACACAAAAAAAAT
```

-continued

```
ATCCAGTGAATTATAAGTCTAAATGGAGAAGGCAAAACTTTAATCTTTTA
GAAAATAATATAGAAGCATGCCATCAAGACTTCAGTGTAGAGAAAAATTT
CTTATGACTCAAAGTCCTAACCACAAAGAAAAGATTGTTAATTAGATTGC
```

Step 4: Creation of new multiple cloning site in pCpG-mcs (Invivogen)—creates pCpG-Linker4.

The pCpG cloning vector, pCpG-mcs G2 (Invivogen), was digested with EcoRI to remove the mammalian expression cassette containing the mCMV enhancer, the hEF1 promoter, the synthetic intron, the multiple cloning site, and the SV40 polyadenylation signal. The EcoRI-digested pCpG-mcs G2

```
          1         10        20        30        40        50        60        70        80        90
          |---------+---------+---------+---------+---------+---------+---------+---------+---------+
   eIF5A              MADDLDFETGDAGASATFPNQCSALRKNGFVVLKGRPCKIVEMSTSKTGKHGHAKVHLVGIDIFTGKKYEDICPSTHNM
HA-5A_K50R  MDMYPYDVPDYAADDLDFETGDAGASATFPNQCSALRKNGFVVLKGRPCKIVEMSTSKTGKHGHAKVHLVGIDIFTGKKYEDICPSTHNM
Consensus   ...........aADDLDFETGDAGASATFPNQCSALRKNGFVVLKGRPCKIVEMSTSKTGKHGHAKVHLVGIDIFTGKKYEDICPSTHNM
                     100       110       120      130 131     140       150       160  165
            ---------+---------+---------+---------+|--------+---- ----+---------+----|
   eIF5A    DVPNIKRNDFQLIGIQDGYLSLLQDSGEVREDLRLPEGDLGKEIEQKYDCGEEILITVLSAMTEEAAVAIKANAK
HA-5A_K50R  DVPNIKRNDFQLIGIQDGYLSLLQDSGEVREDLRLPEGDLGKEIEQKYDCGEEILITVLSAMTEEAAVAIKANAK
Consensus   DVPNIKRNDFQLIGIQDGYLSLLQDSGEVREDLRLPEGDLGKEIEQKYDCGEEILITVLSAMTEEAAVAIKANAK
```

```
ATGAATATTAAGACTTATTTTTAAAATTAAAAAACCATTAAGAAAAGTCA

GGCCATAGAATGACAGAAAATATTTGCAAC
```

βGlo MAR (nucleotides 1-380); EcoRI recognition sequence (nucleotides 396-401); XhoI recognition sequence (nucleotides 401-406); ClaI recognition sequence (nucleotides 409-414); NotI recognition sequence (nucleotides 417-424); MluI recognition sequence (nucleotides 427-432); IFNβ S/MAR (nucleotides 438-1,030).

Step 5: Subcloning of B29 DS4.4 3' enhancer into pCpG-Linker4—creates pCpG-DHS4.4.

The B29 DHS4.4 3' enhancer was amplified by PCR using pGEM-4.4enh #8 as a template and the following primers: forward 5'-GAA GCGGCCGCACCACCCTGGGCCAGGCTGG-3' (SEQ ID NO: 23); and reverse 5'-CC ACGCGTAGAGGTGTTAAAAAGTCTTTAGGTAAAG-3' (SEQ ID NO: 24). The resulting PCR fragment was digested with NotI and MluI and ligated into the NotI and MluI sites in the new multiple cloning site of pCpG-Linker4 to create pCpG-DHS4.4.

>pCpG-DHS4.4 full-length sequences (2,282 bp (SEQ ID NO: 25))

```
TTAATTAAAATTATCTCTAAGGCATGTGAACTGGCTGTCTTGGTTTTCAT

CTGTACTTCATCTGCTACCTCTGTGACCTGAAACATATTTATAATTCCAT

TAAGCTGTGCATATGATAGATTTATCATATGTATTTTCCTTAAAGGATTT

TTGTAAGAACTAATTGAATTGATACCTGTAAAGTCTTTATCACACTACCC

AATAAATAATAAATCTCTTTGTTCAGCTCTCTGTTTCTATAAATATGTAC

AAGTTTTATTGTTTTTAGTGGTAGTGATTTTATTCTCTTTCTATATATAT

ACACACACATGTGTGCATTCATAAATATATACAATTTTTATGAATAAAAA

ATTATTAGCAATCAATATTGAAAACCACTGATTTTTGTTTATGTGAGCAA

ACAGCAGATTAAAAGGAATTCTCGAGTCATCGATAAGCGGCCGCACCACC

CTGGGCCAGGCTGGGCCAAGCCAGGCGGCCCCTGTGTTTTCCCCAGTCTC

TGGGCTGCTGGAGGGAACCAGGTTGTTTTGGCATCAGCCTCTACTGAGCC

GGAGCCCTTCCTTTCCTGCTGCTTTGCATAGTGGCACTAATTCCGTCCTC

CTACCTCCACCAGGGACCTAGGCAGCCGGGTAGATGGTGGGAGGAGGCTT

CACTTCTCCCCCAAGCAGGGTCTCCACCTGCTTGAGGCTGCCCTGGGTTG

GGGGAGGCCTTGGCTTTACCTAAAGACTTTTTAACACCTCTACGCGTAAT

TCAGTCAATATGTTCACCCCAAAAAAGCTGTTTGTTAACTTGCCAACCTC

ATTCTAAAATGTATATAGAAGCCCAAAAGACAATAACAAAAATATTCTTG

TAGAACAAAATGGGAAGAATGTTCCACTAAATATCAAGATTTAGAGCAA

AGCATGAGATGTGTGGGGATAGACAGTGAGGCTGATAAAATAGAGTAGAG

CTCAGAAACAGACCCATTGATATATGTAAGTGACCTATGAAAAAAATATG

GCATTTTACAATGGGAAAATGATGATCTTTTTCTTTTTTAGAAAAACAGG

GAAATATATTTATATGTAAAAAATAAAAGGGAACCCATATGTCATACCAT

ACACACAAAAAAATTCCAGTGAATTATAAGTCTAAATGGAGAAGGCAAAA

CTTTAAATCTTTTAGAAAATAATATAGAAGCATGCCATCAAGACTTCAGT

GTAGAGAAAAATTTCTTATGACTCAAAGTCCTAACCACAAAGAAAAGATT

GTTAATTAGATTGCATGAATATTAAGACTTATTTTTAAAATTAAAAAACC

ATTAAGAAAAGTCAGGCCATAGAATGACAGAAAATATTTGCAACACCCCA

GTAAAGAGAATTGTAATATGCAGATTATAAAAGAAGTCTTACAAATCAG

TAAAAAATAAAACTAGACAAAAATTTGAACAGATGAAAGAGAAACTCTAA

ATAATCATTACACATGAGAAACTCAATCTCAGAAATCAGAGAACTATCAT

TGCATATACACTAAATTAGAGAAATATTAAAAGGCTAAGTAACATCTGTG

GCTTAATTAAAACAGGTAGTTGACAATTAAACATTGGCATAGTATATCTG

CATAGTATAATACAACTCACTATAGGAGGGCCATCATGGCCAAGTTGACC

AGTGCTGTCCCAGTGCTCACAGCCAGGGATGTGGCTGGAGCTGTTGAGTT

CTGGACTGACAGGTTGGGGTTCTCCAGAGATTTTGTGGAGGATGACTTTG

CAGGTGTGGTCAGAGATGATGTCACCCTGTTCATCTCAGCAGTCCAGGAC

CAGGTGGTGCCTGACAACACCCTGGCTTGGGTGTGGGTGAGAGGACTGGA

TGAGCTGTATGCTGAGTGGAGTGAGGTGGTCTCCACCAACTTCAGGGATG

CCAGTGGCCCTGCCATGACAGAGATTGGAGAGCAGCCCTGGGGGAGAGAG

TTTGCCCTGAGAGACCCAGCAGGCAACTGTGTGCACTTTGTGGCAGAGGA

GCAGGACTGAGGATAACCTAGGAAACCTTAAAACCTTTAAAAGCCTTATA

TATTCTTTTTTTTCTTATAAAACTTAAAACCTTAGAGGCTATTTAAGTTG

CTGATTTATATTAATTTTATTGTTCAAACATGAGAGCTTAGTACATGAAA

CATGAGAGCTTAGTACATTAGCCATGAGAGCTTAGTACATTAGCCATGAG

GGTTTAGTTCATTAAACATGAGAGCTTAGTACATTAAACATGAGAGCTTA

GTACATACTATCAACAGGTTGAACTGCTGATC
```

βGlo MAR (nucleotides 1-400); EcoRI recognition sequence (nucleotides 416-421); XhoI recognition sequence (nucleotides 421-426); ClaI recognition sequence (nucleotides 429-434); NotI recognition sequence (nucleotides 437-444); DHS4.4 (nucleotides 445-741); MluI recognition sequence (nucleotides 742-747); IFNβ S/MAR(nucleotides 753-1, 569).

Step 6: Subcloning of B29 promoter+HA-eIF5A1$^{K50R}$+SV40 pA expression cassette into pCpG-DHS4.4—creates pExp-5.

The B29-eIF5A1 expression cassette containing the minimal B29 promoter, the synthetic intron, HA-eIF5A1$^{K50R}$, and the SV40 pA, was amplified from pB29-eIF5A1K50R_7 (Step 3) by PCR using the following primers: forward 5'-GTTATCGATACTAGTGCGACCGCCAAACC-3' (SEQ ID NO: 26); and reverse 5'-CAAGCGGCCGCCATACCACATTTGTAGAGGTTTTAC-3' (SEQ ID NO: 27). The resulting PCR fragment was digested with ClaI and NotI and sublcloned into the ClaI and NotI sites in the multiple cloning site of pCpG-DHS4.4 to create pExp-5.

Step 7: Replacement of HA-eIF5A1$^{K50R}$ in pExp-5 with non-HA eIF5A1$^{K50R}$ creates final vector, pExp5A.

The pExp-5 plasmid was digested with NcoI and NheI to remove HA-eIF5A1$^{K50R}$. A non-HA-tagged eIF5A1$^{K50R}$ PCR fragment was amplified from pHM6-eIF5A1$^{K50R}$ by PCR using the following primers: forward 5'-CACCATG-GCAGATGATTTGGACTTC-3' (SEQ ID NO: 28); and reverse 5'-CGCGCTAGCCAGTTATTTTGCCATCGCC-3' (SEQ ID NO: 16). The resulting PCR product was digested with NcoI and NheI and ligated into the NcoI and NheI sites of B29-5 #3 to generate B29-K50R. B29-K50R was digested with NcoI and NheI and the 470 bp eIF5A1$^{K50R}$ fragment was gel purified and ligated to NcoI/NheI-digested pExp-5 to generate the final expression vector, pExp5A.

Example 18

Testing of pExp5A

Figure 24B:
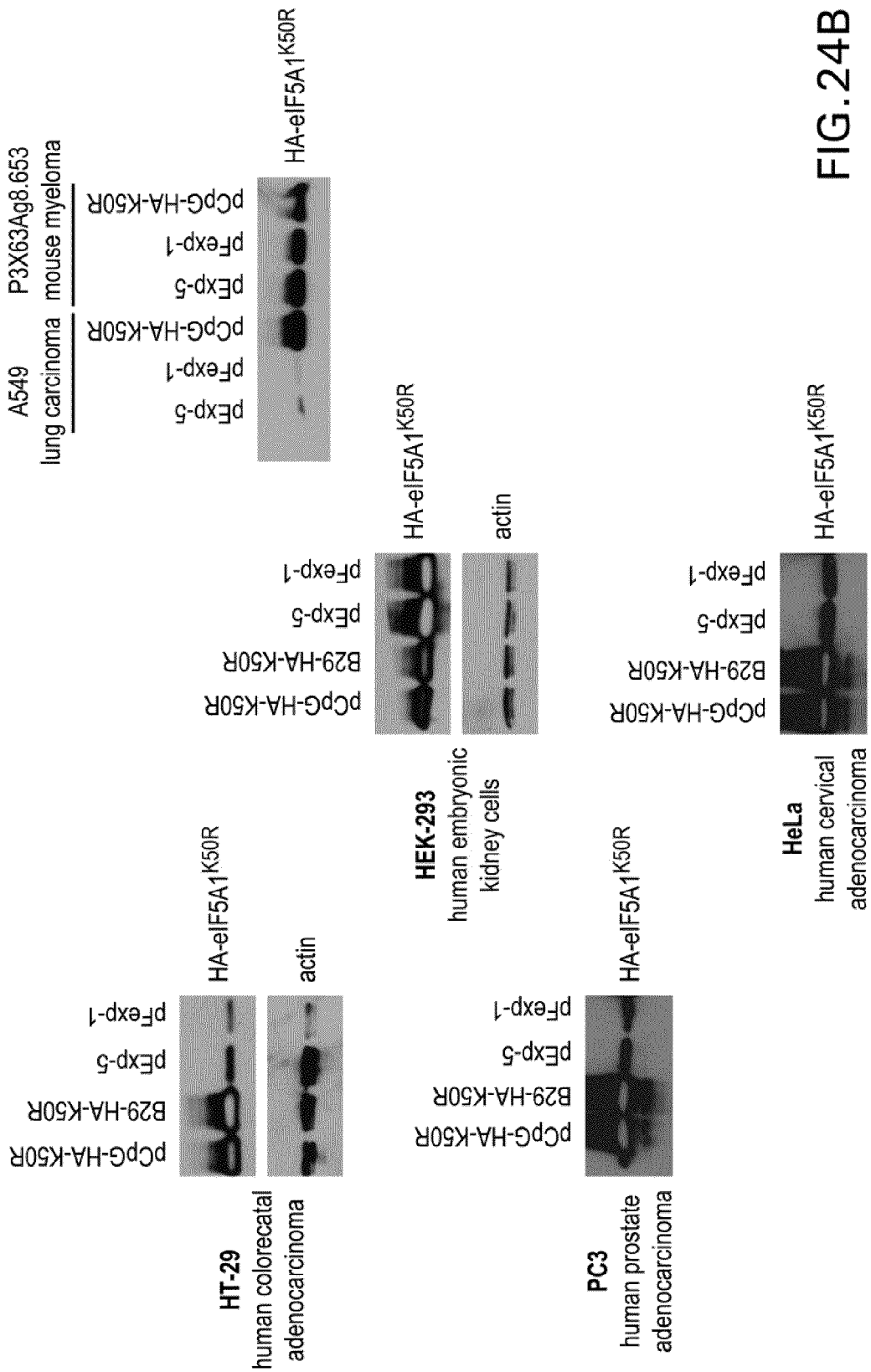
FIG. 24 shows the rexpression of eIF5A1$^{K50R}$ in various cell lines. See example 18.

Various cell lines were transfected with plasmids using Lipofectamine 2000 and expression of HA-eIF5A1K50R was determined 24 hours following transfection by Western blotting with an anti-HA antibody (Roche). Different cells lines tested were P3X63Ag8.653 (mouse B lymphoblast—myeloma), KAS (hyman myeloma), HepG2 (huma liver hepatocellular carcinoma), T24 (human bladder carcinoma); HT-29 (human colorectal adenocarcinoma), HEK-293 (human embryonic kidney cells), PC3 (human prostrate adenocarcinoma); HeLa (human cervical adenocarcinoma), and A549 (lung carcinoma). See FIG. 24.

pExp-5 plasmid expresses HA-eIF5A1$^{K50R}$ in both human and mouse myeloma cell lines at comparable levels to a plasmid with the constitutive EF1 promoter (CpG-eIF5A1$^{K50R}$). However expression of HA-eIF5A1$^{K50R}$ driven by pExp-5 is limited in non-B cell lines compared to expression by a constitutive promoter. The one exception was in HEK-293 cells, a human embryonic kidney cell line where high levels of HA-eIF5A1$^{K50R}$ expression was observed following pExp-5 transfection—this may be due to the embryonic nature of the cell line; at this time we do not know if pExp-5 expresses in adult kidney cells. The final plasmid for use in toxicity studies and clinical trial will be a version of pExp-5 in which HA-eIF5A1$^{K50R}$ has been replaced by non-HA tagged eIF5A1$^{K50R}$ (pExp5A). pExp-5 contains HA-tagged eIF5A1$^{K50R}$ under the control of the minimal human B29 promoter/enhancer; expression of HA-eIF5A1$^{K50R}$ was compared to that driven by plasmids with constitutive expression as well as to a plasmid containing the full-length B29 promoter Example 19

Formation of In vivo JETPEI™ Nanoparticle

This example given is for formation of the in vivo JET-PEI™ nanoparticle complex for injection into 20 g mouse for a dose of 1.5 mg/kg (0.1 mL)—1.5 mg/kg=1.0 mg pExp5A/kg+0.5 mg h5A1/kg—DNA: siRNA ratio=2:1.

Dilute plasmid DNA and siRNA into a total volume of 25 ml. Use sterile water to adjust the volume. *Dilute 20 mg of plasmid DNA (10 ml at 2 mg/ml) and 10 mg of siRNA (10 ml at 1 mg/ml) into a total volume of 25 ml. Use sterile water to make up difference. Adjust the volume of DNA solution to 50 ml 5% glucose by adding 25 ml of 10% glucose (provided with PEI kit). Vortex gently and centrifuge briefly. Dilute in vivo JETPEI™ into a total volume of 25 ml of water. *Dilute 3.6 ml of in vivo JETPEI™ into a total volume of 25 ml of water. Adjust final volume to 50 ml with 10% glucose to end up with a final concentration of 5% glucose. Vortex gently and centrifuge briefly. Immediately add 50 ml of diluted PEI to the 50 ml of diluted DNA (do not reverse the order!). Vortex briefly and immediately spin down.

After formation the complex is stable for 8 to 10 hours. The N/P ratio of the complex should be 6. The N/P ratio is the ratio of the number of positively charged nitrogen residues of in vivo-jetPEI to the number of negatively charged phosphate residues of DNA and siRNA. DNA and siRNA contain the same number of phosphate groups per gram. The N/P ratio is therefore a measure of the ionic balance within the complex. Increasing the N/P ratio of the complex can increase the toxicity of the complex. In vivo JET-PEI is provided as a 150 mM solution (expressed as nitrogen residues) while DNA contains 3 nmoles of anionic phosphate in 1 mg. The final concentration of DNA in the final volume should not exceed 0.5 mg/ml. The DNA should be of high quality and prepared in water. In vivo-jetPEI and 10% glucose should be brought to room temperature prior to use.

Example 20

Figure 22:
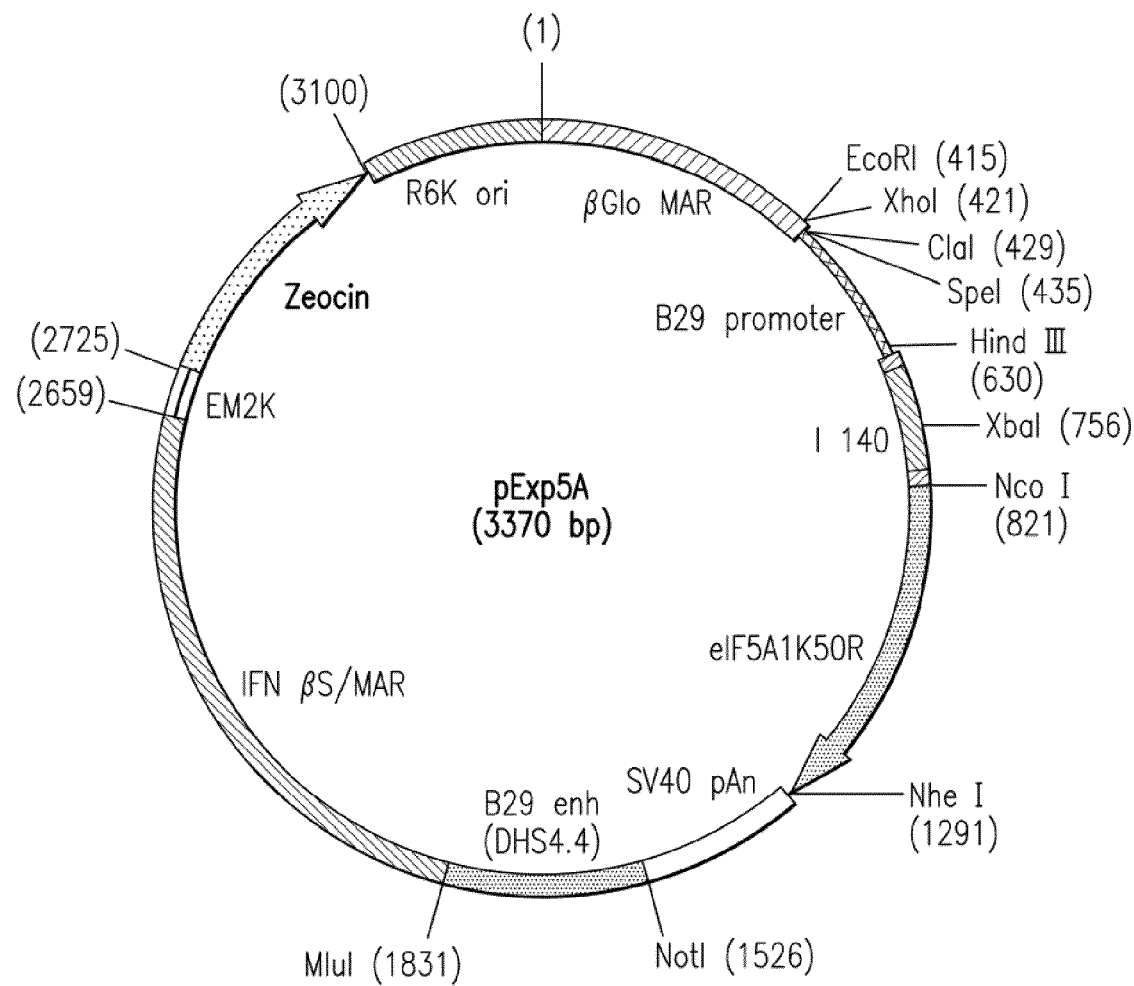
FIG. 22 shows the map of pExp5A, the construction of which is described in Example 17.

Dose Range-Finding and Repeat Dose Studies with Intra-Venous SNS01 and SNS-EF1/UU in Mice SNS01 is one embodiment of the present invention—it is a cancer therapy biologic targeted to the treatment of multiple myeloma. SNS01 is comprised of three components: a DNA vector expressing a pro-apoptotic mutant of eIF5A (see FIG. 22); an siRNA that targets the native eIF5A that promotes growth/anti-apoptosis of cancer cells (see the sequence in FIG. 25); and a synthetic polymer called polyethylenimine (In vivo-jetPEI; Polyplus Transfection Inc.) that acts as a delivery vehicle.

The purpose of the studies was to determine the maximum tolerated dose and the feasibility of long-term administration of therapeutic doses of intra-venous SNS01 into mice. Two separate studies were performed. The maximum tolerated dose (Study ID MTD) study was an 8-day study in which mice received two intra-venous doses of increasing amounts of SNS01 (from 2.2 mg/kg to 3.7 mg/kg) and toxicity was assessed by monitoring clinical signs, body weight, organ weight and liver enzymes. The 9-week repeated dose study (Study ID:EX6) was a study designed to assess toxicity following long-term administration of twice-weekly therapeutic doses (1.5 mg/kg) of SNS-EF1/UU and as well as it's various components. SNS-EF1/UU is a preclinical version of SNS01 and differs mainly in that expression of eIF5A$^{K50R}$ is driven by a constitutive promoter (one that expresses in all tissues at all times) rather than a B-cell-specific promoter as in the SNS01 complex. The use of the B cell-specific B29 promoter in SNS01 was designed to enhance the safety of the therapeutic by limiting expression of the pro-apoptotic eIF5A mutant to cells of B-cell origin, including myeloma cells. The EX6 study also included a group of mice that were dosed with a mouse-specific eIF5A siRNA to determine whether there were any toxic effects of suppressing eIF5A in mouse tissues. Toxicity in the repeated dose study was assessed by monitoring clinical signs, body weight, hematology, liver enzymes, as well as histopathology.

| Study ID | Animal Model | Injection Schedule | Duration of Treatment | Test Article |
|---|---|---|---|---|
| MTD | CD-1 (female) | Twice weekly Intra-venous | 8-Days (2 injections) | SNS01 |

-continued

| | | | | | |
|---|---|---|---|---|---|
| EX6 | Balb/c (female) | Twice weekly Intra-venous | 9-Weeks | SNS-EF1/UU SNS-EF1/UU components tested individually Mouse eIF5A siRNA | |

| Test Article | Plasmid DNA | siRNA | Vehicle | Material Grade |
|---|---|---|---|---|
| SNS01[a] | pExp5A[c] (eIFSA$^{K50R}$ expression driven by B29 B-cell-specific promoter) | eIF5A siRNA (dTdT overhang[d]) human-specific eIF5A siRNA | In vivo-jetPEI ™ | GLP-grade materials |
| SNS-EF1/UU[b] | pCpG-HA-eIFSA$^{K50R}$ (HA-eIF5A$^{K50R}$ expression driven by ubiquitous EF1 promoter) | h5A1 (UU overhang[d]) human-specific eIF5A siRNA | In vivo-jetPEI ™ | Research-grade materials |

[a] SNS01 contains GLP-grade materials and is being developed for the clinic
[b] SNS-EF1/UU is a test article used in preclinical research that led to the development of SNS01
[c] the pExp5A plasmid is RNAi-resistant due to the fact that the plasmid contains only the open reading frame of eIF5A while the eIF5A siRNA (h5A1) targets the 3' UTR of eIF5A
[d] the sequence of the SNS01 eIF5A siRNA and the h5A1 siRNA are identical except for the presencce of a dTdT overhang rather than a UU overhang on the 3' terminal ends of the siRNA; the dTdT overhang does not affect the target selectivity or efficacy of the siRNA but has been proposed to enhance stability Preclinical experiments have indicated that SNS01 is therapeutic at doses of 0.75 mg/kg to 1.5 mg/kg (Study EX9). In the 8-day dose range-finding study (Study ID: MTD) significantly higher doses than the therapeutic range was tested to determine the upper limit of the dose range. Twice-weekly intra-venous doses of the test article was well tolerated at the lower dose levels of 2.2 mg/kg and 2.9 mg/kg although one mouse reached morbidity at the 2.9 mg/kg and was euthanized. Doses at 3.3 mg/kg or above resulted in survival rates of approximately 20-25%. Therefore, the maximum tolerated dose is between 2.2 mg/kg and 2.9 mg/kg and is well above the therapeutic range of 0.75 mg/kg to 1.5 mg/kg.

In the 9-week repeated dose study (Study ID: EX6) the mice received twice weekly tail vein injections of therapeutic doses (1.5 mg/kg) of SNS-EF1/UU and no test article-related toxic effects were observed over the period of the study. The DNA and siRNA were also tested separately in this study and both were well tolerated by the mice. Since the human eIF5A siRNA is not active in mice, a mouse eIF5A-specific siRNA was also included in this study. No toxic effects related to chronic administration of the mouse eIF5A siRNA were observed over the 9-week period. These results indicate that therapeutic doses of SNS01 and SNS-EF1/UU are non-toxic to mice even when administered over long periods.

Test Article and Vehicle

| Test Article | Manufacturer of Plasmid DNA component | Manufacturer of siRNA component | Manufacturer of PEI component | Formation of Test Article |
|---|---|---|---|---|
| SNS01 | VGXI Lot # pExp5A.08L007 | Avecia | Polyplus Transfection Inc GLP-Grade | Components were combined with 10% glucose to form nano-complexes; complexes were injected within 2-4 hours |
| SNS-EF1/UU | Qiagen EndoFree Plasmid Mega Kit <0.1 EU/µg DNA | ThermoScientific Dharmacon RNAi Technologies | Polyplus Transfection Inc. Research-Grade | Components were combined with 10% glucose to form nano-complexes; complexes were injected within 2-4 hours |
| Storage Conditions (Stability) | −20° C. (≥1 year) | −20° (≥1 year) | 4° (≥1 year) | Room Temperature (≥6 hours) |

Test Systems and Study Designs

All aspects of this study were conducted in accordance with the guidelines set out by the University of Waterloo Animal Care Committee (Waterloo, Ontario, Canada) as established by the Canadian Council on Animal Care and the Province of Ontario Animals for Research Act.

The CD-1 and BALB/c mice were obtained from Charles River Laboratories (Quebec, Canada). Mice from both studies received the test article twice-weekly via tail vein intra-venous injections. Slow injections (~2-3 minutes) were used to deliver volumes greater than 0.2 ml.

The mice for the 8-day study were approximately 6-9 weeks old at the start of study. The mice for the 9-week repeated dose study were approximately 5-6 weeks old at the initiation of the study.

STUDY ID: MTD

| Group | No. Animals (female) | Test Article | N/P ratio[a] | Dose level (mg/kg) | Injection Volume | Total # injections |
|---|---|---|---|---|---|---|
| MTD-C | 5 | 5% Glucose | — | — | 0.33 mL | 2 |
| MTD-PA | 5 | SNS01 | 6 | 2.2 mg/kg | 0.20 mL | 2 |
| MTD-PB | 5 | SNS01 | 6 | 2.9 mg/kg | 0.27 mL | 2 |
| MTD-PC | 4 | SNS01 | 6 | 3.3 mg/kg | 0.30 mL | 1[b] |
| MTD-PD | 5 | SNS01 | 6 | 3.7 mg/kg | 0.33 mL | 1[b] |

[a] N/P ratio = ratio of positively-charged nitrogens on PEI to the negatively-charged phosphate groups of the nucleic acids
[b] due to toxicity the surviving mice were not given a second injection

STUDY ID: EX6

| Group | No. Animals (female) | Test Article | N/P ratio | Dose level (mg/kg) | Injection Volume | Total # injections |
|---|---|---|---|---|---|---|
| Ex6-G1 | 4 | 5% Glucose | — | — | 0.10 mL | 20 |
| Ex6-G2 | 5 | Vehicle Control[a] | 8 | 1.5 mg/kg | 0.10 mL | 20 |
| Ex6-G3 | 5 | siRNA[b] | 8 | 1.5 mg/kg | 0.10 mL | 20 |
| Ex6-G4 | 6 | DNA[c] | 8 | 1.5 mg/kg | 0.10 mL | 20 |
| Ex6-G5 | 4 | SNS-EF1/UU | 8 | 1.5 mg/kg | 0.10 mL | 20 |
| Ex6-G6 | 6 | Mouse siRNA[d] | 8 | 1.5 mg/kg | 0.10 mL | 20 |

[a] PEI complex containing a non-expressing plasmid (same vector background as pExp5A) and a non-targeting siRNA
[b] PEI complex containing a non-expressing plasmid (same vector background as pExp5A) and the h5A1 siRNA
[c] PEI complex containing pCpG-HA-eIF5A$^{K50R}$ plasmid and a non-targeting siRNA
[d] PEI complex containing a non-expressing plasmid (same vector background as pExp5A) and a mouse-specific eIF5A siRNA (the human eIF5A siRNA is not active in mouse)

8-Day Maximum Tolerated Dose Study (MTD)

The two-dose 8-day study was a dose range-finding study designed to determine the maximum tolerated dose of SNS01. The dose range was 2.2 mg/kg to 3.7 mg/kg and is well above the therapeutic dose range of 0.75 mg/kg to 1.5 mg/kg. At the lowest dose (2.2 mg/kg) of SNS01 no clinical signs of toxicity were observed except for one mouse that exhibited slightly ruffled fur and decreased activity that resolved within one hour. No clinical signs of toxicity were observed following the 2$^{nd}$ injection of 2.2 mg/kg of SNS01. All the mice maintained their weight throughout the study. No macroscopic changes in the organs were observed. The organ weight to body weight ratios were unchanged from the control group except for a modest increase in the ratio of the liver weight:body weight ratio. However, since an increase in this ratio was not observed in any of the higher dose level groups it is unlikely to be related to the test article.

Four out of five mice tolerated 2.9 mg/kg of SNS01 with no clinical signs of toxicity. However, one mouse experienced convulsions and mild respiratory distress within 1 hour of injection and had to be humanely euthanized. No clinical signs of toxicity were observed following the 2$^{nd}$ injection of SNS01 in the remaining mice. The mice maintained their weight throughout the study and no macroscopic changes in the organs or changes in the organ weight to body weight ratios were observed. There was a slight increase in the serum levels of ALT following two doses of 2.9 mg/kg SNS01.

As expected, doses of SNS01 at or above 3.3 mg/kg were not well tolerated and in both groups all mice but one had to be humanely euthanized. In all cases where mice were humanely euthanized due to morbidity the clinical signs appeared within 1 hour of injection and were consistent with other reported studies using high doses of PEI. The surviving mice of the 3.3 mg/kg and 3.7 mg/kg recovered completely within 4 hours after the injection and maintained their weight throughout the study, although they did not receive a 2$^{nd}$ dose. The maximum tolerated dose of SNS01 therefore appears to be between 2.2 mg/kg and 2.9 mg/kg.

9-Week Repeated Dose Study (EX6)

The purpose of the 9-week repeated dose study was to assess the safety of chronic administration of therapeutic doses (1.5 mg/kg) of SNS-EF1/UU, a complex that was used for preclinical studies during development of SNS01. SNS-EF1/UU does not differ significantly from SNS01, the major difference being that the materials are research-grade and that eIF5A$^{K50R}$ expression is driven by the constitutive human EF1 promoter that is active in all cell types. Although SNS01 uses a B-cell-specific promoter to drive eIF5A$^{K50R}$ expression, the use of a constitutive promoter in this safety study allows for the assessment of toxicity resulting from the accumulation of the mutant eIF5A$^{K50R}$ protein in non-B-cell tissues. Another aspect of the 9-week repeated dose study was the inclusion of groups to test the safety of the individual components of SNS-EF1/UU. The DNA group (Ex6-G3) was dosed with a complex containing the eIF5A plasmid and a non-targeting control siRNA while the siRNA group (Ex6-G4) was dosed with a complex containing the human eIF5A (h5A1) siRNA and a non-expressing plasmid. Since the test article SNS-EF1/UU contains a human eIF5A siRNA that will not affect expression of the endogenous mouse eIF5A, another feature of this study was the inclusion of a group (Ex6-G6) that was dosed with PEI complexes containing a non-expressing plasmid and an siRNA that efficiently targets mouse eIF5A. This group allowed assessment of the safety of chronic administration of an active eIF5A siRNA.

All animals survived to the scheduled sacrifice date. No clinical signs of toxicity were observed in any of the groups over the course of the 9-week study and the mice in all groups continued to gain weight during the study period. Red and white blood cell counts were measured three and six weeks after the initiation of treatment and were normal for all dosing groups. Serum liver enzyme levels were measured following sacrifice and were within the normal range for all mice. No changes in the macroscopic appearance of the organs were observed in any of the groups. Histopathological analysis of the major organs was conducted by an independent pathologist (and revealed no toxicity attributable to the test article.

Chronic administration of therapeutic doses of SNS-EF1/UU is well tolerated by mice and no adverse effects were observed. In addition, chronic administration of a mouse-specific eIF5A siRNA revealed no toxic effects, indicating that the administration of PEI complexes containing a human eIF5A siRNA should be safe for humans.

Example 21

Figure 26:
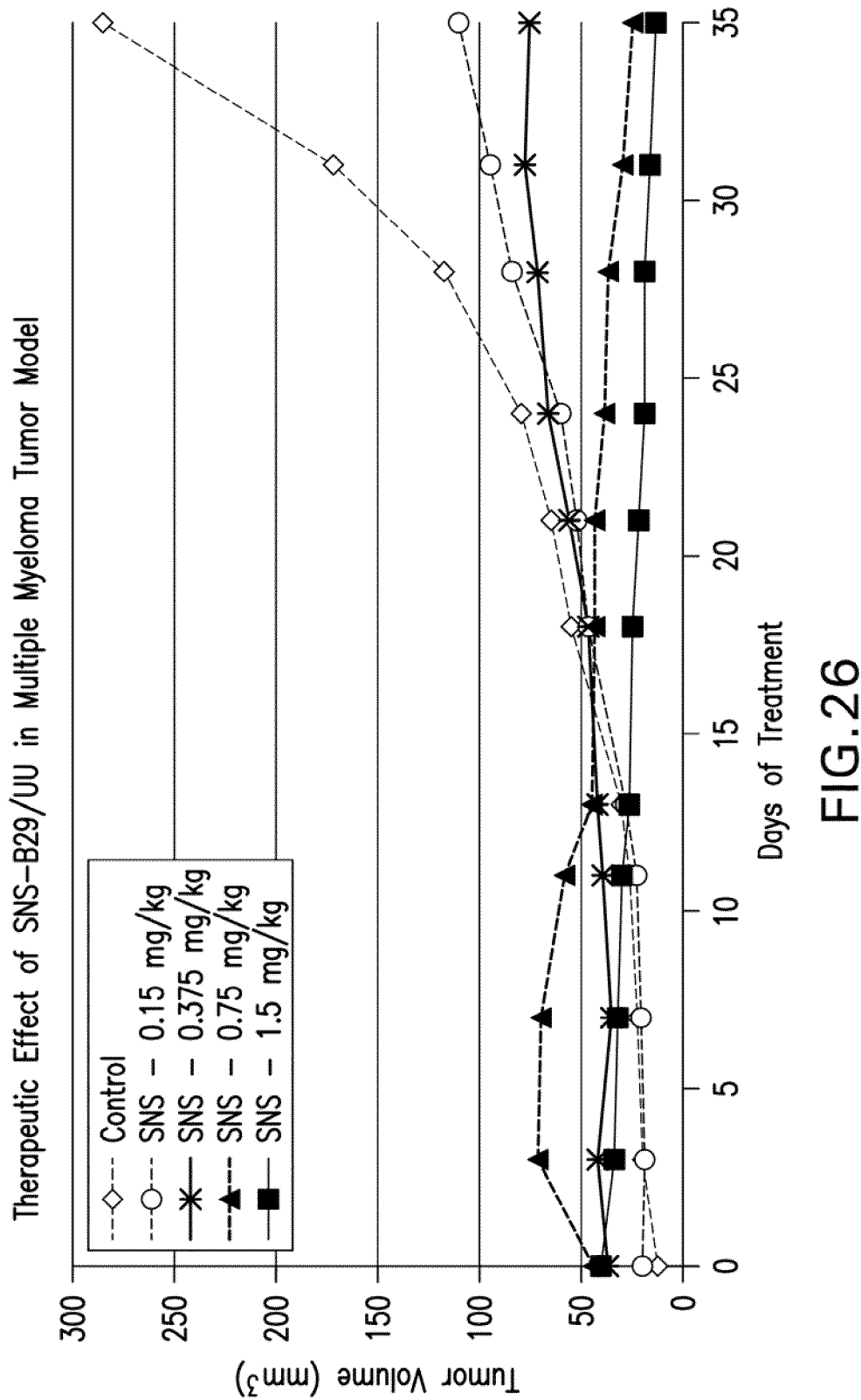
FIG. 26 provides the results of efficacy studies in multiple myeloma. See example 21.
Figure 27:
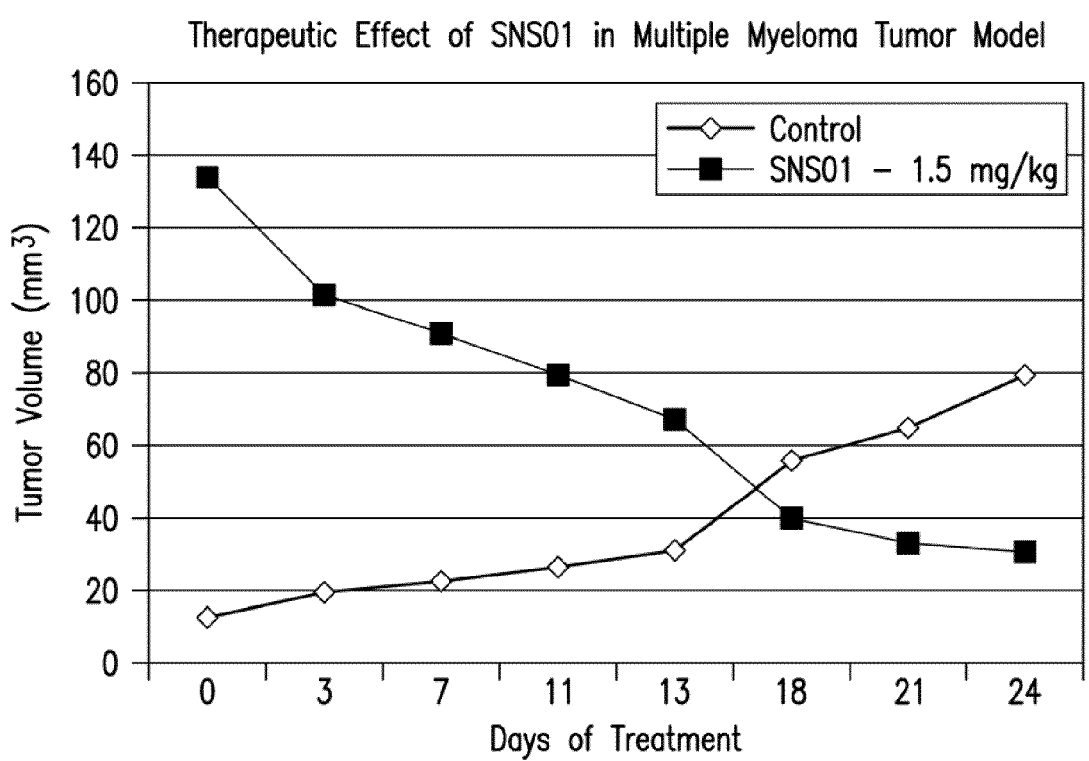
FIG. 27 provides the results of efficacy studies in multiple myeloma. See example 21.

Therapeutic Efficacy Studies with Intra-Venous SNS-B29/UU and SNS01 in Multiple Myeloma Tumour-Bearing Mice SNS01 is as described above. The test article SNS-B29/UU is a preclinical version of SNS01. SNS-B29/UU differs very little from SNS01, the chief difference being that the components are of research-grade rather than GLP-grade. The purpose of the study reported here was to determine the minimum effective dose of SNS-B29/UU and to confirm that the GLP-grade materials that comprise SNS01 perform as well as the research-grade materials that were used for the preclinical studies. The repeated dose tumour study (Study ID:EX9) was a 5-week study in which the ability of increasingly smaller twice-weekly doses of SNS-B29/UU to inhibit subcutaneous tumour growth in mice was assessed in order to determine the optimal therapeutic dose of SNS01. The treated animals were also assessed for signs of toxicity by monitoring clinical signs, body weight and organ weight.

surements and by excising and weighing tumour tissue following sacrifice. SNS-B29/UU doses of 0.75 mg/kg and 1.5 mg/kg resulted in significant tumour shrinkage indicating that the therapeutic range of SNS-B29/UU lies between 0.75 mg/kg and 1.5 mg/kg. Effective inhibition of growth of subcutaneous tumours was also observed at 0.38 mg/kg SNS-B29/UU although no tumour shrinkage was observed. Some inhibition of tumour growth was even observed at doses as low as 0.15 mg/kg SNS-B29/UU indicating a broad therapeutic range. See FIGS. 26 and 27.

The efficacy of SNS01 made using GLP-grade components was compared to SNS-B29/UU and was found have a com-

| Study ID | Animal Model | Injection Schedule | Duration of Treatment | Test Article |
|---|---|---|---|---|
| Ex9 | C.B17 (SCID) (female) mice bearing subcutaneous human multiple myeloma tumours (KAS-6/1) | Twice weekly Intra-venous | 35 Days | SNS-B29/UU |
| | | Twice weekly Intra-venous | 25 Days | SNS01 |

| Test Article | Plasmid DNA | siRNA | Vehicle | Material Grade |
|---|---|---|---|---|
| SNS01[a] | pExp5A[c] (eIF5A$^{K50R}$ expression driven by B29 B-cell-specific promoter) | eIF5A siRNA[d] (dTdT overhang[e]) human-specific eIF5A siRNA | In vivo-jetPEI ™ | GLP-grade materials |
| SNS-B29/UU[b] | pExp5A[c] | h5A1 (UU overhang[e]) human-specific eIF5A siRNA | In vivo-jetPEI ™ | Research-grade materials |

[a]SNS01 contains GLP-grade materials and is being developed for the clinic
[b]SNS-B29/UU is a test article used in preclinical research that led to the development of SNS01
[c]the pExp5A plasmid is RNAi-resistant due to the fact that the plasmid contains only the open reading frame of eIF5A while the eIF5A siRNA (h5A1) targets the 3' UTR of eIF5A
[d]the sequence of the eIF5A siRNA and the h5A1siRNAs are identical except for the presencee of a dTdT overhang rather than a UU overhang on the 3' terminal ends of the siRNA; the dTdT overhang does not affect the target selectivity or efficacy of the siRNA but has been proposed to enhance stability The therapeutic range of SNS-B29/UU was determined in SCID mice bearing subcutaneous human multiple myeloma tumours. Doses of SNS-B29/UU between 0.15 mg/kg and 1.5 mg/kg were tested. The anti-tumoural efficacy of the test article was determined by twice-weekly tumour volume meaparable efficacy in the inhibition of tumour growth. Treatment of tumour-bearing SCID mice with SNS01 and SNS-B29/UU was well tolerated and the mice continued to gain weight throughout the study.

| | Test Article and Vehicle | | | |
|---|---|---|---|---|
| Test Article | Manufacturer of Plasmid DNA component | Manufacturer of siRNA component | Manufacturer of PEI component | Formation of Test Article |
| SNS01 | VGXI Lot # pExp5A.08L007 | Avecia | Polyplus Transfection Inc GLP-Grade | Components were combined with 10% glucose to form nano-complexes; complexes were injected within 2-4 hours |
| SNS-B29/UU | Qiagen EndoFree Plasmid Mega Kit <0.1 EU/μg DNA | ThermoScientific Dharmacon RNAi Technologies | Polyplus Transfection Inc. Research-Grade | Components were combined with 10% glucose to form nano-complexes; complexes were injected within 2-4 hours |

-continued

| Test Article | Manufacturer of Plasmid DNA component | Manufacturer of siRNA component | Manufacturer of PEI component | Formation of Test Article |
|---|---|---|---|---|
| Storage Conditions (Stability) | −20° C. (≥1 year) | −20° (≥1 year) | 4° (≥1 year) | Room Temperature (≥6 hours) |

Test Systems and Study Design

The female C.B. 17/IcrHsd-Prkdc (SCID) mice were obtained from Harlan (Indianapolis, Ind., USA). Subcutaneous tumours were established by injecting $10 \times 10^6$ viable KAS-6/1 (human multiple myeloma) cells into the right flank of 5 to 6 week-old mice. Treatment with SNS-B29/UU began when the tumours reached an approximate size of 20 to 40 $mm^3$ (approximately 4 weeks after tumour cell injection). Treatment with SNS01 began when the tumours reached an approximate size of 130 $mm^3$ (approximately 6 weeks after tumour cell injection). Mice received the test article twice-weekly via tail vein intra-venous injection.

| | | STUDY ID: EX9 | | | | |
|---|---|---|---|---|---|---|
| Group | No. Animals (female) | Test Article | N/P ratio | Dose level (mg/kg) | Injection Volume | Total # injections |
| Ex9-G1 | 3 | Control[a] | 6 | 1.5 mg/kg | 0.1 mL | 11 |
| Ex9-G2 | 4 | SNS-B29/UU | 6 | 1.5 mg/kg | 0.1 mL | 11 |
| Ex9-G3 | 4 | SNS-B29/UU | 6 | 0.75 mg/kg | 0.05 mL | 11 |
| Ex9-G4 | 4 | SNS-B29/UU | 6 | 0.38 mg/kg | 0.025 mL | 11 |
| Ex9-G5 | 3 | SNS-B29/UU | 6 | 0.15 mg/kg | 0.01 mL | 11 |
| Ex9-G9 | 3 | SNS01 | 6 | 1.5 mg/kg | 0.1 mL | 7 |

[a]PEI complex containing a non-expressing plasmid (same vector background as pExp5A) and a non-targeting siRNA Repeated Dose Tumour Study The repeated dose tumour study was designed to determine the minimum effective therapeutic dose of SNS-B29/UU and to confirm that the GLP-grade SNS01 test article retained the tumour inhibition activity demonstrated by the research-grade test article SNS-B29/UU. A secondary objective was to assess any toxic effects of the treatment by monitoring the treated mice for clinical signs, body weight, and organ weight. Test article therapeutic anti-tumoural activity was monitored by twice-weekly tumour volume measurements using digital calipers. Upon sacrifice the tumours were excised and weighed.

All the mice survived to the scheduled sacrifice date. Control mice that were treated with PEI nanocomplexes containing a non-expressing plasmid and a non-targeting siRNA had an average tumour volume of 284 $mm^3$ at the time of sacrifice while mice treated with 1.5 mg/kg SNS-B29/UU had an average tumour volume of only 13 $mm^3$, a 95% (*p=0.026) reduction in tumour growth. However, when it was attempted to excise the tumours from mice that had been treated with 1.5 mg/kg SNS-B29/UU, no evidence of a tumour was found in any of the mice. Decreasing the dose of SNS-B29/UU by half to 0.75 mg/kg still resulted in a 91% (*p=0.03) and 87% (*p=0.04) decrease in tumour volume and weight, respectively, and in one mouse the tumour had completely disappeared. Therefore, the optimum therapeutic dose for twice-weekly injections of SNS-B29/UU appears to be between 0.75 mg/kg and 1.5 mg/kg. Twice-weekly doses of SNS-B29/UU doses as low as 0.15 mg/kg still resulted in a 60% reduction in the final tumour volume indicating that SNS-B29/UU has potent anti-tumoural activity over a wide dose range.

In addition to inhibiting tumour growth, treatment with SNS-B29/UU and SNS01 at 0.75 mg/kg and 1.5 mg/kg resulted in significant reduction in tumour volume indicating that this treatment is capable of inducing tumour regression, likely through the induction of apoptosis in the tumour. The percent change in tumour volume in tumour-bearing mice treated with SNS-B29/UU, at dose levels of 0.75 mg/kg and 1.5 mg/kg, was −244% and −245%, respectively. The tumours of control mice increased in size by more than 2000% during the same time period. Twice-weekly injections of SNS01 also significantly shrunk multiple myeloma tumours. The percent change in tumour volume for mice treated with 1.5 mg/kg SNS01 was −349%, indicating that SNS01 is just as effective as SNS-B29/UU. The use of GLP-grade materials may in fact have increased the biological activity since treatment with SNS01 achieved a 349% decrease in tumour volume following only 25 days of treatment while SNS-B29/UU achieved a 245% reduction in tumour volume following 35 days of treatment. In addition, the tumours treated with SNS01 were quite large (~130 $mm^3$) indicating that treatment with SNS01 is effective against well-established tumours.

The treatment was well tolerated by all mice and no clinical signs of toxicity were observed. The mice in all groups continued to gain weight throughout the study. No changes in the macroscopic appearance of the organs was observed at necropsy and no significant changes in the organ weight to body weight ratios occurred.

Therefore SNS01 (and its preclinical version SNS-B29/UU) is well tolerated by SCID mice and is extremely effective in treating subcutaneous human multiple myeloma tumours when delivered by intra-venous injection twice per week. All doses of SNS-B29/UU that were tested were effective at inhibiting tumour growth but the highest dose of 1.5 mg/kg successfully eliminated tumours in all mice receiving treatment.

Example 22

Biodistribution of Plasmid DNA and siRNA Polyethylenimine (JetPEI) Complexes

Green fluorescent protein ("GFP")GFP-expression constructs were used to determine localization of plasmid DNA delivered by PEI complexes. Two promoters were used to drive GFP expression: EF1: ubiquitous promoter (EF1::GFP) or B29: B-cell specific promoter (B29::GFP). PEI complexes containing 20 micrograms of GFP plasmid DNA and 10 micrograms of a fluorescently-labelled (DY547) h5A1 siRNA were prepared at an N/P ratio of 6. BalB/C mice were injected intra-venously with either 5% glucose or PEI complexes on two consecutive days. Seventy-two hours following the firsts injection the mice were euthanized and their organs were harvested and analyzed for GFP expression and DY547-siRNA by confocal microscopy.

Bone Marrow:
In most cases there was evidence of DY547-siRNA but no GFP expression. Timing of organ harvest may not coincide with peak expression of GFP; and there may be quenching of GFP signal or GFP may not be expressed. However, GFP and DY547 that colocalized to the same bone marrow cells in some instances was observed. Therefore, this provides evidence that PEI nanoparticles can transfect bone marrow cells in a live animal when given by intra-venous injection Lung:
In most cases there was evidence of DY547-siRNA but no GFP expression. Timing of organ harvest may not coincide with peak expression of GFP or there may be quenching of GFP signal or GFP may not be expressed.

Spleen:
Evidence of GFP expression (when driven by EF1 promoter) colocalizing in cells also positive for the presence of DY547-siRNA was seen. Expression of GFP was much lower in spleen cells when driven by the B29 promoter. This shows that PEI nanoparticles appear to transfect cells of the spleen.

Kidney:
No GFP or DY547 was observed indicating nanoparticles may not enter kidney.

Liver:
In most cases there was evidence of DY547-siRNA but no GFP expression. This provides evidence that PEI nanoparticles are transfecting cells of the liver.

Heart:
Colocalization of EF1::GFP and DY547-siRNA in tissue of heart was seen, thus indicating that PEI nanoparticles may be transfecting this organ. No GFP was observed with B29 promoter.

Example 23

Effect of DNA:siRNA Ratio on HA-eIF5A$^{K50}$R Expression

KAS cells were transfected with nanoparticles containing B29-HA-eIF5A$^{K50}$R (plasmid driven by B-cell-specific promoter) and h5A1 siRNA. JET PEI™ nanoparticles containing different ratios of pExp5A and h5A1 siRNA were made and incubated for 4 hours at room temperature prior to addition to KAS cells. Four hours after transfection, the nanoparticle-containing media was replaced with fresh media. Twenty-four hours later the cell lysate was harvested and used for western blot analysis with an antibody against HA. The ratio of DNA:siRNA was varied from the standard ratio of 2:1. The accumulation of HA-eIF5A$^{K50R}$ peaked at ratios of 1:0, 3:1, and 2:1. See FIG. 30.

Example 24

Effect of DNA:siRNA Ratio on Apoptosis Induced by Nanoparticle Transfection

Nanoparticles containing different ratios of pExp5A and h5A1 siRNA were made and incubated for 4 hours at room temperature prior to addition to KAS cells. Four hours after transfection, the nanoparticle-containing media was replaced with fresh media. Forty-eight hours later the cells were harvested, labelled with Annexin V/PI and analyzed by FACS. The induction of apoptosis was highest in cells transfected with nanoparticles with the standard DNA:siRNA ratio of 2:1. See FIG. 31.

Example 25

Administration of PEI Complexes (N/P=6 or 8) Containing eIF5A1K50R Plasmid and eIF5A1 siRNA (siSTABLE or non-siSTABLE) Inhibits Growth of Multiple Myeloma Subcutaneous Tumours and Results in Tumour Shrinkage SCID mice were injected subcutaneously with KAS cells. Treatment was initiated when palpable tumours were observed. Mice were injected intra-venously 2 times per week with either: (G1) PEI complexes containing 20 mg of pCpG-mcs (empty vector) and 10 mg of control siRNA at N/P=8 (medium dose); (G5) PEI complexes containing 20 mg of the RNAi-resistant plasmid pCpG-eIF5A1k50R and 10 mg of siSTABLE h5A1 siRNA at N/P=8 (medium dose, siSTABLE); (G8) PEI complexes containing 20 mg of the RNAi-resistant plasmid pCpG-eIF5A1k50R and 10 mg of h5A1 siRNA at N/P=6 (medium dose, N/P=6). The data shown is the individual tumour volume for the mice in each group. The final injection was given at day 40 after initiation of treatment. See FIG. 32.

Example 26

JET PEI™ Nanoparticles are being Effectively taken up by Tumour Tissue and that Nanoparticles are Delivering Plasmid and siRNA to the same Cell Tumour section 48 hours after injection with nanoparticles containing pExp-GFP (GFP under control of B-cell-specific promoter) and DY547-siRNA (fluorescently-labelled siRNA). Co-localized expression of GFP and DY547 is observed in tumour section following confocal microscopy indicating that the nanoparticles are being effectively taken up by tumour tissue and that nanoparticles are delivering plasmid and siRNA to the same cell. See FIG. 33.

The invention claimed is:

1. A composition comprising a complex of an eIF5A1 siRNA targeted against the 3' end of eIF5A1, and an expression vector comprising a polynucleotide encoding a mutant eIF5A1 that contains a K50R mutation in the eIF5A1 amino acid sequence set forth in SEQ ID NO: 18, wherein the siRNA and the expression vector are complexed to polyethylenimine.

2. The composition of claim 1 wherein the siRNA has the sequence of SEQ ID NO: 31 and the complement thereof (SEQ ID NO: 32).

3. The composition of claim 2 comprising a tissue specific promoter.

4. The composition of claim 2 wherein the expression vector comprises a pCpG plasmid.

5. The composition of claim 1 wherein the eIF5A1 siRNA and the expression vector comprising the mutant eIF5A1 polynucleotide are independently complexed to polyethylenimine.

6. The composition of claim 1 wherein the eIF5A1 siRNA and the expression vector comprising the mutant eIF5AI polynucleotide are together complexed to polyethylenimine.

7. The composition of claim 1 wherein the eIF5A1 siRNA targeted against the 3' end of eIF5A1 and an expression vector comprising a polynucleotide encoding a mutant eIF5A1 present in an amount effective to induce apoptosis in multiple myeloma cells in a human subject suffering from multiple myeloma.

* * * * *

SEQUENCE LISTING

<160> NUMBER OF SEQ ID NOS: 34

<210> SEQ ID NO 1
<211> LENGTH: 21
<212> TYPE: DNA
<213> ORGANISM: Homo sapiens

<400> SEQUENCE: 1

```
aagctggact cctcctacac a                                          21

<210> SEQ ID NO 2
<211> LENGTH: 21
<212> TYPE: DNA
<213> ORGANISM: Homo sapiens

<400> SEQUENCE: 2
aaaggaatga cttccagctg a                                          21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
acacauccuc cucaggucgt t                                          21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
cgaccugagg aggaugugut t                                          21

<210> SEQ ID NO 5
<211> LENGTH: 21
<212> TYPE: RNA
<213> ORGANISM: Homo sapiens

<400> SEQUENCE: 5
gcuggacucc uccuacacau u                                          21

<210> SEQ ID NO 6
<211> LENGTH: 154
<212> TYPE: PRT
<213> ORGANISM: Homo sapiens

<400> SEQUENCE: 6

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
                20                  25                  30

Leu Lys Gly Arg Pro Cys Lys Ile Val Glu Met Ser Thr Ser Lys Thr
            35                  40                  45

Gly Arg His Gly His Ala Lys Val His Leu Val Gly Ile Asp Ile Phe
        50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95
```

```
Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagcaaggga gcacctatg                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gttgcagtga gcggagatg                                                  19

<210> SEQ ID NO 9
<211> LENGTH: 297
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
accaccctgg gccaggctgg gccaagccag gcggcccctg tgttttcccc agtctctggg     60
ctgctggagg gaaccaggtt gttttggcat cagcctctac tgagccggag cccttccttt    120
cctgctgctt tgcatagtgg cactaattcc gtcctcctac ctccaccagg gacctaggca    180
gccgggtaga tggtgggagg aggcttcact tctcccccaa gcagggtctc cacctgcttg    240
aggctgccct gggttggggg aggccttggc tttacctaaa gactttttaa caccctct     297

<210> SEQ ID NO 10
<211> LENGTH: 800
<212> TYPE: DNA
<213> ORGANISM: Homo sapiens

<400> SEQUENCE: 10
gggaacagct gccagctggg agaccaagtg caatcaacct gcacgtgcaa agcctccctc     60
ccaagccagg ctgtgctcca cttcctgttg accctggagg gaatccttcg aggcccctct    120
gctattcctg ctctgaattc cagcaaggga gcacctatgc tgtgggagct gccagtttaa    180
ctggggaatc aagaccagca caggggaact agtgagaaca gtgccaattt tcaccagatt    240
ccctctggaa ttccaggtgg ggcaggtggg taaggccccc acgcctgcag tttcaggtaa    300
atctctccac caccctgggc caggctgggc caagccaggg gcccctgtgt tttcccccag    360
```

```
tctctgggct gctggaggga accaggttgt tttggcatca gcctctactg agccggagcc    420
cttcctttcc tgctgctttg catagtggca ctaattccgt cctcctacct ccaccaggga    480
cctaggcagc cgggtagatg gtgggaggag gcttcacttc tcccccaagc agggtctcca    540
cctgcttgag gctgccctgg gttggggag gccttggctt tacctaaaga cttttaaca    600 cctctgaaca acacagtttc cctgagactt tgaagctctt gttttattta tttatttatt    660
tatttattta cttatttatt tatttgcaga cagagtctca ctctgttgcc cagactggag    720
tgcagtggca ccatctccgc tcactgcaac ctccgtctcc tgagttcaag caattctcct    780
gcctcagcct ccaaagtacc                                                800
```

```
<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaactagtg cgaccgccaa accttagc                                        28

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caaaagcttg acaacgtccg aggctccttg g                                    31

<210> SEQ ID NO 13
<211> LENGTH: 188
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gcgaccgcca aaccttagcg gcccagctga caaaagcctg ccctccccca gggtccccgg     60
agagctggtg cctcccctgg gtcccaattt gcatggcagg aaggggcctg gtgaggaaga    120
ggcggggagg ggacaggctg cagccggtgc agttacacgt tttcctccaa ggagcctcgg    180
acgttgtc                                                             188

<210> SEQ ID NO 14
<211> LENGTH: 1237
<212> TYPE: DNA
<213> ORGANISM: Homo sapiens

<400> SEQUENCE: 14
cctgcagggc ccactagtaa acggagggtt gtgaggagag tgagaggtgg acagagggca     60
ccgacgattt agcatctctt cctctcctgg gggtcgagga tgagagacaa aaaagaagct    120
gccaggaaac ataaaattca gagggctcag ctgcagggct gaggtctgca agcatgctgt    180
gtacacttgt gcatgttgtg ccctgcacaa gggcatctct gaaggggctg cactggaccc    240
aggggcaggg gcgcaaaggt gagttttatat cagttcctga gcactgtggc tccatccagc    300
actctgagga caggcaggat acagctggag gacctgaggg ctcccccaca ccagctcctg    360
```

```
ttccctgccc aagacccct ggacctgcag acaacaattc aacgcactca gagtcccaca    420
gttaagaact ccctgaagaa gcccccagtg gctgcgtggt ggattttcgc aaagctgtct    480
ccacctacat ccaccctgtt tggcagcccc tacatactct ttcacagcat gaggaaggga    540
ggcctctcac caagacctgg actgaatctt ctcccagtgg ctgccacacc tgacctgctc    600
ttgctccaga acctctgtgg ctcccatcct ccacagggtc aacttccaac atggctgcct    660
gcactccagc aagaggctc tgctctgggc ccctccagat gcctgacctg ggtctgtggc    720
tgccctgtcc ttcttcagtg ctcctcttcc cgctgggtga ggaatagttc aggacagagg    780
agctaagttc aggttcattc ataggacagg tgcctatttc gctcacggcc caggaataga    840
gacttgccgg gctcggccct tcggggagtt ggcagacggc agaggggagg ctggctggcc    900
caggggatga ccaccggtgg ggtaagcaca gacagaggg agcacaggct tccccccagaa    960 gactgagagg ccccccagag gcatccacag aggaccccag ctgtgctgcc caagctgggc   1020
gaccgccaaa ccttagcggc ccagctgaca aaagcctgcc ctcccccagg gtccccggag   1080
agctggtgcc tcccctgggt cccaatttgc atggcaggaa ggggcctggt gaggaagagg   1140
cggggagggg acaggctgca gccggtgcag ttacacgttt tcctccaagg agcctcggac   1200
gttgtcacgg gtttggggtc ggggacagag cggtgac                             1237
```

<210> SEQ ID NO 15
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
cgccatggac atgtacccct tacgacgtcc agactacgct gcagatgatt tggacttcga    60
g                                                                   61
```

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cgcgctagcc agttattttg ccatcgcc                                      28
```

<210> SEQ ID NO 17
<211> LENGTH: 497
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
acatgtaccc ttacgacgtc ccagactacg ctgcagatga tttggacttc gagacaggag    60
atgcaggggc ctcagccacc ttcccaatgc agtgctcagc attacgtaag aatggttttg   120
tggtgctcaa gggccggcca tgtaagatcg tcgagatgtc tacttcgaag actggcaggc   180
atggccatgc caaggtccat ctggttggca ttgatatttt tactgggaag aaatatgaag   240
atatctgccc gtcgactcat aacatggatg tccccaacat caaaaggaat gatttccagc   300
```

```
tgattggcat ccaggatggg tacctatccc tgctccagga cagtggggag gtacgagagg    360
accttcgtct gcctgaggga gaccttggca aggagattga gcagaagtat gactgtggag    420
aagagatcct gatcacagtg ctgtccgcca tgacagagga ggcagctgtt gcaatcaagg    480
cgatggcaaa ataactg                                                   497
```

<210> SEQ ID NO 18
<211> LENGTH: 165
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Asp Met Tyr Pro Tyr Asp Val Pro Asp Tyr Ala Ala Asp Asp Leu
1               5                   10                  15

Asp Phe Glu Thr Gly Asp Ala Gly Ala Ser Ala Thr Phe Pro Met Gln
            20                  25                  30

Cys Ser Ala Leu Arg Lys Asn Gly Phe Val Val Leu Lys Gly Arg Pro
        35                  40                  45

Cys Lys Ile Val Glu Met Ser Thr Ser Lys Thr Gly Arg His Gly His
    50                  55                  60

Ala Lys Val His Leu Val Gly Ile Asp Ile Phe Thr Gly Lys Lys Tyr
65                  70                  75                  80

Glu Asp Ile Cys Pro Ser Thr His Asn Met Asp Val Pro Asn Ile Lys
                85                  90                  95

Arg Asn Asp Phe Gln Leu Ile Gly Ile Gln Asp Gly Tyr Leu Ser Leu
            100                 105                 110

Leu Gln Asp Ser Gly Glu Val Arg Glu Asp Leu Arg Leu Pro Glu Gly
        115                 120                 125

Asp Leu Gly Lys Glu Ile Glu Gln Lys Tyr Asp Cys Gly Glu Glu Ile
    130                 135                 140

Leu Ile Thr Val Leu Ser Ala Met Thr Glu Glu Ala Ala Val Ala Ile
145                 150                 155                 160

Lys Ala Met Ala Lys
                165
```

<210> SEQ ID NO 19
<211> LENGTH: 154
<212> TYPE: PRT
<213> ORGANISM: Homo sapiens

<400> SEQUENCE: 19

```
Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65                  70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110
```

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aattctcgag tcatcgataa gcggccgcag acgcgt                              36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aattacgcgt ctgcggccgc ttatcgatga ctcgag                              36

<210> SEQ ID NO 22
<211> LENGTH: 1030
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ggcatgtgaa ctggctgtct tggttttcat ctgtacttca tctgctacct ctgtgacctg    60
aaacatattt ataattccat taagctgtgc atatgataga tttatcatat gtattttcct   120
taaaggattt ttgtaagaac taattgaatt gatacctgta aagtctttat cacactaccc   180
aataaataat aaatctcttt gttcagctct ctgtttctat aaatatgtac aagttttatt   240 gttttttagtg gtagtgattt tattctcttt ctatatatat acacacacat gtgtgcattc   300
ataaatatat acaatttta tgaataaaaa attattagca atcaatattg aaaaccactg    360 attttgttt atgtgagcaa acagcagatt aaaaggaatt ctcgagtcat cgataagcgg    420
ccgcagacgc gtaattcagt caatatgttc accccaaaaa agctgtttgt taacttgcca    480
acctcattct aaaatgtata tagaagccca aagacaata acaaaatat tcttgtagaa     540 caaaatggga agaatgttc cactaaatat caagatttag agcaaagcat gagatgtgtg    600
gggatagaca gtgaggctga taaaatagag tagagctcag aaacagaccc attgatatat    660
gtaagtgacc tatgaaaaaa atatggcatt ttacaatggg aaaatgatga tcttttttctt    720 ttttagaaaa acagggaaat atatttatat gtaaaaaata aagggaacc catatgtcat    780 accatacaca caaaaaaat tccagtgaat tataagtcta aatggagaag gcaaactttt    840
aaatctttta gaaataata tagaagcatg ccatcaagac ttcagtgtag agaaaaattt    900
cttatgactc aaagtcctaa ccacaaagaa aagattgtta attagattgc atgaatatta    960
agacttattt ttaaaattaa aaaaccatta agaaaagtca ggccatagaa tgacagaaaa   1020

```
<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaagcggccg caccaccctg ggccaggctg g                              31

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccacgcgtag aggtgttaaa aagtctttag gtaaag                         36

<210> SEQ ID NO 25
<211> LENGTH: 2282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
```

| | | | |
|---|---|---|---|
| ttaattaaaa ttatctctaa ggcatgtgaa ctggctgtct tggttttcat ctgtacttca | 60 |
| tctgctacct ctgtgacctg aaacatattt ataattccat taagctgtgc atatgataga | 120 |
| tttatcatat gtatttcct taaaggattt ttgtaagaac taattgaatt gatacctgta | 180 |
| aagtctttat cacactaccc aataaataat aaatctcttt gttcagctct ctgtttctat | 240 |
| aaatatgtac aagttttatt gttttagtg gtagtgattt tattctcttt ctatatatat | 300 |
| acacacacat gtgtgcattc ataaatatat acaattttta tgaataaaaa attattagca | 360 |
| atcaatattg aaaaccactg attttgtttt atgtgagcaa acagcagatt aaaaggaatt | 420 |
| ctcgagtcat cgataagcgg ccgcaccacc ctgggccagg ctgggccaag ccaggcggcc | 480 |
| cctgtgtttt ccccagtctc tgggctgctg gagggaacca ggttgttttg gcatcagcct | 540 |
| ctactgagcc ggagcccttc cttcctgct gctttgcata gtggcactaa ttccgtcctc | 600 |
| ctacctccac cagggaccta gcagccggg tagatggtgg gaggaggctt cacttctccc | 660 |
| ccaagcaggg tctccacctg cttgaggctg ccctgggttg ggggaggcct tggctttacc | 720 |
| taaagacttt ttaacaccctc tacgcgtaat tcagtcaata tgttcaccc aaaaaagctg | 780 |
| tttgttaact tgccaaccttc attctaaaat gtatatagaa gcccaaaaga caataacaaa | 840 |
| aatattcttg tagaacaaaa tgggaaagaa tgttccacta aatatcaaga tttagagcaa | 900 |
| agcatgagat gtgtggggat agacagtgag gctgataaaa tagagtagag ctcagaaaca | 960 |
| gacccattga tatatgtaag tgacctatga aaaaatatg gcattttaca atgggaaaat | 1020 |
| gatgatcttt ttcttttta gaaaacagg gaaatatatt tatatgtaaa aataaaagg | 1080 |
| gaacccatat gtcataccat acacacaaaa aaattccagt gaattataag tctaaatgga | 1140 |
| gaaggcaaaa ctttaaatct tttagaaaat aatatagaag catgccatca agacttcagt | 1200 |

-continued

```
gtagagaaaa atttcttatg actcaaagtc ctaaccacaa agaaaagatt gttaattaga      1260
ttgcatgaat attaagactt attttttaaaa ttaaaaaacc attaagaaaa gtcaggccat     1320
agaatgacag aaaatatttg caacacccca gtaaagagaa ttgtaatatg cagattataa     1380
aaagaagtct tacaaatcag taaaaaataa aactagacaa aaatttgaac agatgaaaga     1440
gaaactctaa ataatcatta cacatgagaa actcaatctc agaaatcaga gaactatcat     1500
tgcatataca ctaaattaga gaaatattaa aaggctaagt aacatctgtg gcttaattaa     1560
aacaggtagt tgacaattaa acattggcat agtatatctg catagtataa tacaactcac     1620
tataggaggg ccatcatggc caagttgacc agtgctgtcc cagtgctcac agccagggat     1680
gtggctggag ctgttgagtt ctggactgac aggttggggt tctccagaga ttttgtggag     1740
gatgactttg caggtgtggt cagagatgat gtcaccctgt tcatctcagc agtccaggac     1800
caggtggtgc ctgacaacac cctggcttgg gtgtgggtga gaggactgga tgagctgtat     1860
gctgagtgga gtgaggtggt ctccaccaac ttcaggatgg ccagtggccc tgccatgaca     1920
gagattggag agcagccctg ggggagagag tttgccctga gagacccagc aggcaactgt     1980
gtgcactttg tggcagagga gcaggactga ggataaccta ggaaacctta aaacctttaa     2040
aagccttata tattctttttt tttcttataa aacttaaaac cttagaggct atttaagttg    2100
ctgatttata ttaatttttat tgttcaaaca tgagagctta gtacatgaaa catgagagct    2160
tagtacatta gccatgagag cttagtacat tagccatgag ggtttagttc attaaacatg    2220
agagcttagt acattaaaca tgagagctta gtacatacta tcaacaggtt gaactgctga    2280
tc                                                                   2282
```

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gttatcgata ctagtgcgac cgccaaacc                                      29

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caagcggccg ccataccaca tttgtagagg ttttac                              36

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caccatggca gatgatttgg acttc                                          25

<210> SEQ ID NO 29
<211> LENGTH: 154

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Ala Asp Asp Leu Asp Phe Glu Thr Gly Asp Ala Gly Ala Ser Ala
1               5                   10                  15

Thr Phe Pro Met Gln Cys Ser Ala Leu Arg Lys Asn Gly Phe Val Val
            20                  25                  30

Leu Lys Gly Arg Pro Cys Lys Ile Val Glu Met Ser Thr Ser Lys Thr
        35                  40                  45

Gly Lys His Gly His Ala Lys Val His Leu Val Gly Ile Asp Ile Phe
    50                  55                  60

Thr Gly Lys Lys Tyr Glu Asp Ile Cys Pro Ser Thr His Asn Met Asp
65              70                  75                  80

Val Pro Asn Ile Lys Arg Asn Asp Phe Gln Leu Ile Gly Ile Gln Asp
                85                  90                  95

Gly Tyr Leu Ser Leu Leu Gln Asp Ser Gly Glu Val Arg Glu Asp Leu
            100                 105                 110

Arg Leu Pro Glu Gly Asp Leu Gly Lys Glu Ile Glu Gln Lys Tyr Asp
        115                 120                 125

Cys Gly Glu Glu Ile Leu Ile Thr Val Leu Ser Ala Met Thr Glu Glu
    130                 135                 140

Ala Ala Val Ala Ile Lys Ala Met Ala Lys
145                 150

<210> SEQ ID NO 30
<211> LENGTH: 3370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
ttaattaaaa ttatctctaa ggcatgtgaa ctggctgtct tggttttcat ctgtacttca      60
tctgctacct ctgtgacctg aaacatattt ataattccat taagctgtgc atatgataga    120
tttatcatat gtattttcct taaaggattt ttgtaagaac taattgaatt gatacctgta    180
aagtctttat cacactaccc aataaataat aaatctcttt gttcagctct ctgtttctat    240
aaatatgtac aagttttatt gtttttagtg gtagtgattt tattctcttt ctatatatat    300
acacacacat gtgtgcattc ataaatatat acaattttta tgaataaaaa attattagca    360
atcaatattg aaaccactg attttttgtttt atgtgagcaa acagcagatt aaaaggaatt    420
ctcgagtcat cgatactagt gcgaccgcca aaccttagcg gcccagctga caaaagcctg    480
ccctccccca gggtccccgg agagctggtg cctcccctgg gtcccaattt gcatggcagg    540
aaggggcctg gtgaggaaga ggcggggagg ggacaggctg cagccggtgc agttacacgt    600
tttcctccaa ggagcctcgg acgttgtcaa gcttctgcct tctccctcct gtgagtttgg    660
taagtcactg actgtctatg cctgggaaag ggtgggcagg agatggggca gtgcaggaaa    720
agtggcacta tgaaccctgc agccctagga atgcatctag acaattgtac taaccttctt    780 ctcttttcctc tcctgacagg ttggtgtaca gtagcttcca ccatggcaga tgatttggac    840
ttcgagacag gagatgcagg ggcctcagcc accttcccaa tgcagtgctc agcattacgt    900
aagaatggtt ttgtggtgct caagggccgg ccatgtaaga tcgtcgagat gtctacttcg    960
```

```
aagactggca ggcatggcca tgccaaggtc catctggttg gtattgatat ttttactggg    1020
aagaaatatg aagatatctg cccgtcgact cataacatgg atgtcccaa catcaaaagg     1080 aatgatttcc agctgattgg catccaggat gggtacctat ccctgctcca ggacagtggg    1140
gaggtacgag aggaccttcg tctgcctgag ggagaccttg gcaaggagat tgagcagaag    1200
tatgactgtg gagaagagat cctgatcaca gtgctgtccg ccatgacaga ggaggcagct    1260
gttgcaatca aggcgatggc aaaataactg gctagctggc cagacatgat aagatacatt    1320
gatgagtttg gacaaaccac aactagaatg cagtgaaaaa aatgctttat ttgtgaaatt    1380
tgtgatgcta ttgcttttatt tgtaaccatt ataagctgca ataaacaagt taacaacaac   1440
aattgcattc attttatgtt tcaggttcag ggggaggtgt gggaggtttt ttaaagcaag    1500
taaaacctct acaaatgtgg tatggcggcc gcaccaccct gggccaggct gggccaagcc    1560
aggcggcccc tgtgttttcc ccagtctctg ggctgctgga gggaaccagg ttgttttggc    1620
atcagcctct actgagccgg agcccttcct ttcctgctgc tttgcatagt ggcactaatt    1680
ccgtcctcct acctccacca gggacctagg cagccgggta gatggtggga ggaggcttca   1740
cttctccccc aagcagggtc tccacctgct tgaggctgcc ctgggttggg ggaggccttg    1800
gctttaccta aagactttt aacacctcta cgcgtaattc agtcaatatg ttcaccccaa     1860
aaaagctgtt tgttaacttg ccaacctcat tctaaaatgt atatagaagc ccaaaagaca    1920
ataacaaaaa tattcttgta gaacaaaatg ggaagaatg ttccactaaa tatcaagatt     1980
tagagcaaag catgagatgt gtggggatag acagtgaggc tgataaaata gagtagagct    2040
cagaaacaga cccattgata tatgtaagtg acctatgaaa aaaatatggc attttacaat    2100
gggaaaatga tgatctttt cttttttaga aaaacaggga aatatattta tatgtaaaaa     2160
ataaaaggga acccatatgt cataccatac acacaaaaaa attccagtga attataagtc    2220
taaatggaga aggcaaaact ttaaatcttt tagaaaataa tatagaagca tgccatcaag    2280
acttcagtgt agagaaaaat ttcttatgac tcaaagtcct aaccacaaag aaaagattgt    2340
taattagatt gcatgaatat taagacttat ttttaaaatt aaaaaaccat taagaaaagt    2400
caggccatag aatgacagaa aatatttgca acaccccagt aaagagaatt gtaatatgca    2460
gattataaaa agaagtctta caaatcagta aaaaataaaa ctagacaaaa atttgaacag    2520
atgaaagaga aactctaaat aatcattaca catgagaaac tcaatctcag aaatcagaga    2580
actatcattg catatacact aaattagaga aatattaaaa ggctaagtaa catctgtggc    2640
ttaattaaaa caggtagttg acaattaaac attggcatag tatatctgca tagtataata    2700
caactcacta taggagggcc atcatggcca agttgaccag tgctgtccca gtgctcacag    2760
ccagggatgt ggctggagct gttgagttct ggactgacag gttggggttc tccagagatt    2820
ttgtggagga tgactttgca ggtgtggtca gagatgatgt caccctgttc atctcagcag    2880
tccaggacca ggtggtgcct gacaacaccc tggcttgggt gtgggtgaga ggactggatg    2940
agctgtatgc tgagtggagt gaggtggtct ccaccaactt cagggatgcc agtggccctg    3000
ccatgacaga gattggagag cagccctggg ggagagagtt tgccctgaga gacccagcag    3060
gcaactgtgt gcactttgtg gcagaggagc aggactgagg ataacctagg aaaccttaaa    3120
acctttaaaa gccttatata ttctttttttt tcttataaaa cttaaaacct tagaggctat    3180
ttaagttgct gatttatatt aattttattg ttcaaacatg agagcttagt acatgaaaca    3240
tgagagctta gtacattagc catgagagct tagtacatta gccatgaggg tttagttcat    3300
taaacatgag agcttagtac attaaacatg agagcttagt acatactatc aacaggttga    3360
```

```
actgctgatc                                                           3370

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonculeotide

<400> SEQUENCE: 31
gcuggacucc uccuacacat t                                                 21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
uguguaggag gaguccagct t                                                 21

<210> SEQ ID NO 33
<211> LENGTH: 537
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atagggagac ccaagctgga gaccatgtac ccatacgacg tcccagacta cgctggaagc       60
ttaatggcag atgatttgga cttcgagaca ggagatgcag gggcctcagc caccttccca      120
atgcagtgct cagcattacg taagaatggt tttgtggtgc tcaagggccg gccatgtaag      180
atcgtcgaga tgtctacttc gaagactggc aggcatggcc atgccaaggt ccatctggtt      240
ggtattgata ttttttactgg gaagaaatat gaagatatct gcccgtcgac tcataacatg      300
gatgtcccca acatcaaaag gaatgatttc cagctgattg catccagga tgggtaccta      360 tccctgctcc aggacagtgg ggaggtacga gaggaccttc gtctgcctga gggagacctt      420
ggcaaggaga ttgagcagaa gtatgactgt ggagaagaga tcctgatcac agtgctgtcc      480
gccatgacag aggaggcagc tgttgcaatc aaggccatgg caaaataact ggaattc        537

<210> SEQ ID NO 34
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Tyr Pro Tyr Asp Val Pro Asp Tyr Ala Gly Ser Leu Met Ala Asp
1               5                   10                  15

Asp Leu Asp Phe Glu Thr Gly Asp Ala Gly Ala Ser Ala Thr Phe Pro
            20                  25                  30
```

```
Met Gln Cys Ser Ala Leu Arg Lys Asn Gly Phe Val Val Leu Lys Gly
            35                  40                  45
Arg Pro Cys Lys Ile Val Glu Met Ser Thr Ser Lys Thr Gly Arg His
     50                  55                  60
Gly His Ala Lys Val His Leu Val Gly Ile Asp Ile Phe Thr Gly Lys
 65                  70                  75                  80
Lys Tyr Glu Asp Ile Cys Pro Ser Thr His Asn Met Asp Val Pro Asn
                 85                  90                  95
Ile Lys Arg Asn Asp Phe Gln Leu Ile Gly Ile Gln Asp Gly Tyr Leu
             100                 105                 110
Ser Leu Leu Gln Asp Ser Gly Glu Val Arg Glu Asp Leu Arg Leu Pro
         115                 120                 125
Glu Gly Asp Leu Gly Lys Glu Ile Glu Gln Lys Tyr Asp Cys Gly Glu
     130                 135                 140
Glu Ile Leu Ile Thr Val Leu Ser Ala Met Thr Glu Glu Ala Ala Val
145                 150                 155                 160
Ala Ile Lys Ala Met Ala Lys
                 165
```